(12) United States Patent
Friesen et al.

(10) Patent No.: US 7,897,175 B2
(45) Date of Patent: Mar. 1, 2011

(54) DOSAGE FORMS COMPRISING A CETP INHIBITORS AND AN HMG-COA REDUCTASE INHIBITOR

(75) Inventors: Dwayne T. Friesen, Bend, OR (US); David K. Lyon, Bend, OR (US); Douglas A. Lorenz, Bend, OR (US); Bruno C. Hancock, North Stonington, CT (US); Timothy J. McDermott, Salem, CT (US); Ravi M. Shanker, Groton, CT (US)

(73) Assignee: Bend Research, Inc., Bend, OR (US)

( * ) Notice: Subject to any disclaimer, the term of this patent is extended or adjusted under 35 U.S.C. 154(b) by 1372 days.

(21) Appl. No.: 10/739,567

(22) Filed: Dec. 18, 2003

(65) Prior Publication Data

US 2004/0197398 A1 Oct. 7, 2004

Related U.S. Application Data

(60) Provisional application No. 60/435,345, filed on Dec. 20, 2002.

(51) Int. Cl.
*A61K 9/14* (2006.01)
*A61K 9/20* (2006.01)
*A61K 9/48* (2006.01)

(52) U.S. Cl. .................. 424/484; 464/451; 464/464; 464/489

(58) Field of Classification Search .................. None
See application file for complete search history.

(56) References Cited

U.S. PATENT DOCUMENTS

| | | | |
|---|---|---|---|
| 5,180,589 A | 1/1993 | Joshi et al. | |
| 5,932,587 A | 8/1999 | Schmeck et al. | 514/278 |
| 5,935,939 A | 8/1999 | Kararli et al. | 514/54 |
| 6,004,582 A * | 12/1999 | Faour et al. | 424/473 |
| 6,126,971 A | 10/2000 | Mills et al. | 424/484 |
| 6,197,786 B1 | 3/2001 | DeNinno et al. | 514/313 |
| 6,235,311 B1 | 5/2001 | Ullah et al. | |
| 6,310,075 B1 | 10/2001 | DeNinno et al. | 514/313 |
| 6,548,555 B1 * | 4/2003 | Curatolo et al. | 514/772.4 |
| 6,620,821 B2 * | 9/2003 | Robl | 514/290 |
| 7,115,279 B2 | 10/2006 | Curatolo et al. | |
| 2002/0077348 A1 | 6/2002 | Dean et al. | |
| 2004/0132771 A1 | 7/2004 | Babcock et al. | |
| 2004/0185102 A1 | 9/2004 | Friesen et al. | |

FOREIGN PATENT DOCUMENTS

| | | |
|---|---|---|
| EP | 1027888 A2 * | 8/2000 |
| WO | WO 9638153 A1 * | 12/1996 |
| WO | WO 00/35425 A1 | 6/2000 |
| WO | WO 0038722 | 7/2000 |
| WO | WO0038722 A1 * | 7/2000 |
| WO | WO 01/93860 A1 | 12/2001 |
| WO | WO 02/13797 A2 | 2/2002 |
| WO | WO 0211710 * | 2/2002 |
| WO | WO 0213797 | 2/2002 |
| WO | WO 02100394 | 12/2002 |

OTHER PUBLICATIONS

*Remington: The Science and Practice of Pharmacy*, 19th Edition, (1995).
Serajuddin, A. T. M., et al., Selection of Solid Dosage Form Composition through Drug-Excipient Compatibility Testing, *Journal of Pharmaceutical Sciences*, vol. 88, No. 7, pp. 696-704, (Jul. 1999).
Bauer, K. H., et al., Lehrbuch der Pharmazeutischen Technologie, *Wissenschaftliche Verlaosoesellschaft MBH*, pp. 131-326 (1999).
Gennaro, A.R., Remington: The Science and Practice of Pharmacy 20th ed., Chapter 45, pp. 858-861, Lippincott Williams and Wilkins, Baltimore, Maryland, 2000.
Lachman, L., et al., The Theory and Practice of Industrial Pharmacy, 3rd ed., pp. 330-331, Lea & Febiger, Philadelphia, Pennsylvania, 1986.
Cole, G, Pharmaceutical Coating Technology, Chapter 1, p. 2, Taylor and Francis, Bristol, Pennsylvania, 1995.
Medicines Compendium 2002, "Zocor," pp. 2202-2204, Datapharm Communications Ltd., 2002.
Full Prescribing Information: Zocor (simvastatin), pp. 10-11.
Lieberman, H.A., et al., Pharmaceutical Dosage Forms, 2nd ed,—Tablets, vol. 1, pp. 90-91, lnforma Healthcare, New York, New York, 1989.
Bauer,K., et al, Lehrbuch der Pharmazeutischen Technologie, Chapter 23, Wissenschaftliche Verlagsgesellschaft mgh, Stuttgarg, 1999.
Lieberman, H.A., et al., Pharmaceutical Dosage Forms, 2nd ed, Tablets, vol. 1, pp. 131-132 and pp. 179-181, Informa Healthcare, New York, New York, 1989.
Hatanaka, T., "Clinical Pharmacokinetics of Pravastatin—Mechanisms of Pharmacokinetic Events," Clin. Pharmacokinet., vol. 39, No. 6, pp. 397-412, 2000.

* cited by examiner

*Primary Examiner*—S. Tran
(74) *Attorney, Agent, or Firm*—Chernoff, Vilhauer, McClung & Stenzel

(57) ABSTRACT

A dosage form comprises (1) a solid amorphous dispersion comprising a cholesterol ester transfer protein inhibitor and an acidic concentration-enhancing polymer and (2) an HMG-CoA reductase inhibitor. The solid amorphous dispersion and the HMG-CoA reductase inhibitor are combined in the dosage form so that the solid amorphous dispersion and the HMG-CoA reductase inhibitor are substantially separate from one another in the dosage form.

13 Claims, 4 Drawing Sheets

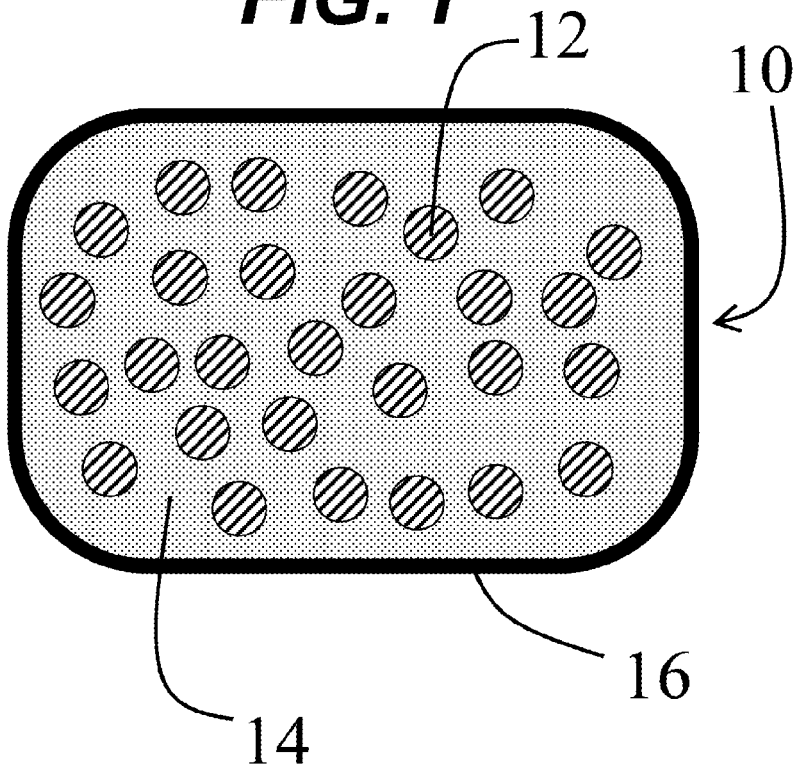
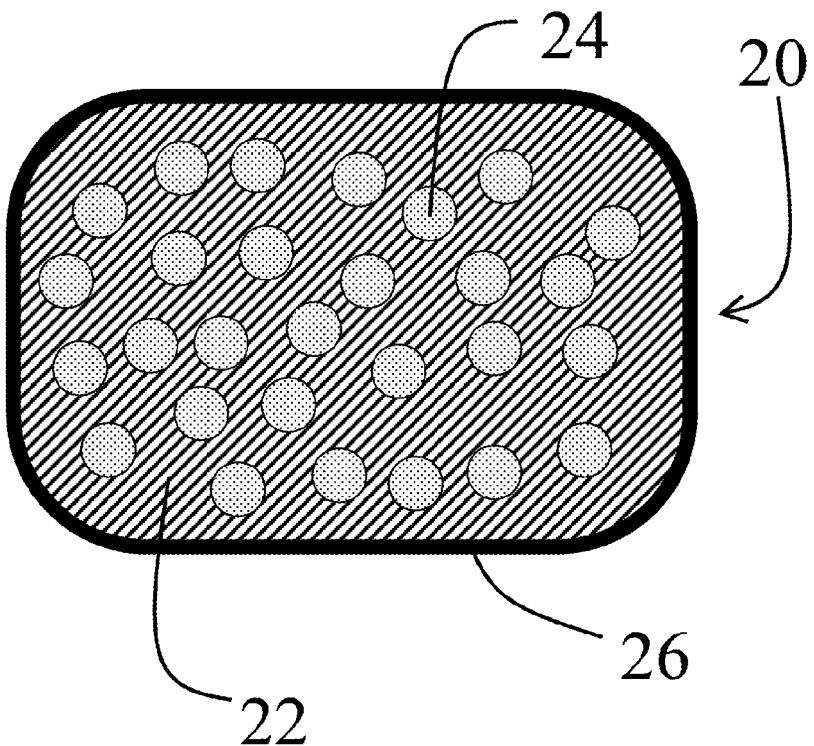

DOSAGE FORMS COMPRISING A CETP INHIBITORS AND AN HMG-COA REDUCTASE INHIBITOR

CROSS-REFERENCE TO RELATED APPLICATION

This application claims the benefit of priority of provisional Patent Application Ser. No. 60/435,345 filed Dec. 20, 2002, which is incorporated herein by reference in its entirety for all purposes.

BACKGROUND

The present invention relates to a dosage form comprising: (1) a solid amorphous dispersion comprising a cholesteryl ester transfer protein (CETP) inhibitor and an acidic concentration-enhancing polymer; and (2) an acid-sensitive HMG-CoA reductase inhibitor.

It is well known that inhibitors of 3-hydroxy-3-methylglutaryl-coenzyme A reductase (HMG-CoA reductase), an important enzyme catalyzing the intracellular synthesis of cholesterol, will bring about reduced levels of blood cholesterol, especially in terms of the low density lipoprotein form of cholesterol. Therefore, HMG-CoA reductase enzyme inhibitors are considered potentially useful as hypocholesterolemic or hypolipidemic agents.

CETP inhibitors are another class of compounds that are capable of modulating levels of blood cholesterol such as, by raising high density lipoprotein (HDL) cholesterol and lowering LDL cholesterol. CETP inhibitors have extremely low aqueous solubility. Accordingly, CETP inhibitors must be formulated so as to be capable of providing good bioavailability. One method for increasing the bioavailability of a CETP inhibitor is to form a solid amorphous dispersion of the drug and a concentration-enhancing polymer. See, e.g., WO02/11710 A2. For many CETP inhibitors, an acidic concentration-enhancing polymer provides the highest level of enhancement.

It is well known that a combination therapy of a CETP inhibitor and an HMG-CoA reductase inhibitor may be used to treat elevated LDL cholesterol and low HDL cholesterol levels. For example, WO02/13797 A2 relates to pharmaceutical combinations of cholesteryl ester transfer protein inhibitors and atorvastatin. The application discloses that the compounds may be generally administered separately or together, with a pharmaceutically acceptable carrier, vehicle or diluent. The compounds may be administered individually or together in any conventional oral, parenteral or transdermal dosage form. For oral administration, the composition may take the form of solutions, suspensions, tablets, pills, capsules, powders and the like.

DeNinno et al., U.S. Pat. No. 6,310,075 B1, relates to CETP inhibitors, pharmaceutical compositions containing such inhibitors and the use of such inhibitors. DeNinno et al. disclose a pharmaceutical combination composition comprising a CETP inhibitor and an HMG-CoA reductase inhibitor. DeNinno disclose that the compounds of the invention may be administered in the form of a pharmaceutical composition comprising at least one of the compounds, together with a pharmaceutically acceptable vehicle, diluent, or carrier. For oral administration a pharmaceutical composition can take the form of solutions, suspensions, tablets, pills, capsules, powders and the like. Similarly, DeNinno et al., U.S. Pat. No. 6,197,786 B1, disclose pharmaceutical combinations comprising CETP inhibitors and HMG-CoA reductase inhibitors.

WO 00/38722 discloses combinations of CETP inhibitors and HMG-CoA reductase inhibitors for cardiovascular indications. The pharmaceutical compositions include those suitable for oral, rectal, topical, buccal, and parenteral administration. The application discloses solid dosage forms for oral administration including capsules, tablets, pills, powders, gel caps and granules.

Schmeck et al., U.S. Pat. No. 5,932,587, disclose another class of CETP inhibitors. Schmeck et al. disclose that the CETP inhibitors may be used in combination with certain HMG-CoA reductase inhibitors such as statins, including atorvastatin.

However, while it is desired to combine the CETP inhibitor and an HMG-CoA reductase inhibitor into a single dosage form, combining a CETP inhibitor and an HMG-CoA reductase inhibitor into a single dosage form presents a number of potential problems. Some HMG-CoA reductase inhibitor compounds are unstable in that they are susceptible to heat, moisture, low pH environment, and light. Some HMG-CoA reductase inhibitors, such as atorvastatin, pravastatin, florastatin, rosuvastatin, and cerivastatin are in the form of hydroxy acids that will degrade to a lactone in an acidic environment. Other HMG-CoA-reductase inhibitors, such as lovastatin and simvastatin, contain substituents that readily degrade in an acidic environment. When packaged in the form of tablets, powders, granules, or within capsules, the HMG-CoA reductase inhibitor may be further destabilized by contact with the molecular moieties of other components of the dosage form. Since pharmaceutical dosage form components such as binders, diluents, antiadherents, surfactants and the like may adversely interact with the active ingredient compound, a stabilizing means may be required for effective pharmaceutical dosages. For example, U.S. Pat. No. 6,126,971 discloses the addition of a stabilizing agent such as calcium carbonate to stabilize the HMG-CoA reductase inhibitor atorvastatin calcium. Nevertheless, the means for stabilizing the HMG-CoA reductase inhibitor must also allow solubilization of the CETP inhibitor.

Accordingly, what is desired is a dosage form containing a CETP inhibitor and an HMG-CoA reductase inhibitor that stabilizes the HMG-CoA reductase inhibitor and that provides good bioavailability for the CETP inhibitor.

SUMMARY OF THE INVENTION

The present invention overcomes the drawbacks of the prior art by providing a unitary dosage form comprising (1) a solid amorphous dispersion comprising a CETP inhibitor and an acidic concentration-enhancing polymer and (2) an HMG-CoA reductase inhibitor. The solid amorphous dispersion and HMG-CoA reductase inhibitor are combined in the dosage form so that the solid amorphous dispersion and the HMG-CoA reductase inhibitor are substantially separate from one another in the dosage form.

By "unitary dosage form" is meant a single dosage form containing both the CETP inhibitor and HMG-CoA reductase inhibitor so that, following administration of the unitary dosage form to a use environment, both the CETP inhibitor and HMG-CoA reductase inhibitor are delivered to the use environment. The term "unitary dosage form" includes a single tablet, caplet, pill, capsule, powder, and a kit comprising one or more tablets, caplets, pills, capsules, sachets, powders, or solutions intended to be taken together.

By "substantially separate from one another" is meant that a sufficient amount of the HMG-CoA reductase inhibitor is physically separated from the solid amorphous dispersion so that the acidic concentration-enhancing polymer does not cause an unacceptable level of chemical degradation of the HMG-CoA reductase inhibitor. The HMG-CoA reductase inhibitor thus has improved chemical stability relative to a blended mixture of (1) particles consisting essentially of the solid amorphous dispersion of the CETP inhibitor and acidic concentration-enhancing polymer alone, and (2) particles consisting essentially of the HMG-CoA reductase inhibitor alone. This improved chemical stability of the HMG-CoA reductase inhibitor is believed to be related primarily to reducing the fraction of HMG-CoA reductase inhibitor molecules that are in contact with the solid amorphous dispersion of CETP inhibitor/acidic concentration-enhancing polymer. As will be described below, there are many ways in which to formulate a unitary dosage form in which the solid amorphous dispersion and the HMG-CoA reductase inhibitor are substantially separate from one anther; that is, the unitary dosage form limits the fraction of HMG-CoA reductase inhibitor molecules that are in contact with the solid amorphous dispersion of the CETP inhibitor and acidic concentration-enhancing polymer.

For some approaches, the separation is macroscopic in nature; that is, the HMG-CoA reductase inhibitor and the solid amorphous dispersion may be, for example, in separate layers of the dosage form so that only those HMG-CoA reductase inhibitor molecules present at the interface of the two layers may be in contact with the solid amorphous dispersion. Further separation between the HMG-CoA reductase inhibitor and the solid amorphous dispersion may be obtained by providing a third layer that separates the two compositions. Alternatively, the unitary dosage form may be in the form of a kit wherein the HMG-CoA reductase inhibitor and solid amorphous dispersion are within separate compartments in the dosage form.

For other approaches, the separation is microscopic in nature; that is, the separation may be due to only one or more intervening molecules. For example, the unitary dosage form may comprise the solid amorphous dispersion and a plurality of relatively large particles or granules comprising the HMG-CoA reductase inhibitor. The HMG-CoA reductase inhibitor molecules located in the interior of the particles or granules are separated from the solid amorphous dispersion by the molecules on the surface of the particles or granules. Alternatively, the solid amorphous dispersion may be in the form of relatively large particles or granules, with molecules of the acidic concentration-enhancing polymer in the solid amorphous dispersion on the interior of the particles or granules being separated from the HMG-CoA reductase inhibitor by the molecules on the surface of the particles or granules. Alternatively, particles or granules of the HMG-CoA reductase inhibitor, particles or granules of the solid amorphous dispersion, or both may be coated with a protective coating, thus separating the HMG-CoA reductase inhibitor and the solid amorphous dispersion. In any case, the HMG-CoA reductase inhibitor and the solid amorphous dispersion are substantially separated from one another so that the acidic concentration-enhancing polymer does not cause an unacceptable level of chemical degradation of the HMG-CoA reductase inhibitor.

Reference to a "use environment" can either mean in vivo fluids, such as the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS) or a Model Fasted Duodenal (MFD) solution. An appropriate PBS solution is an aqueous solution comprising 20 mM-sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine.

"Administration" to a use environment means, where the in vivo use environment is the GI tract, delivery by ingestion or swallowing or other such means to deliver the drugs. One skilled in the art will understand that "administration" to other in vivo use environments means contacting the use environment with the composition of the invention using methods known in the art. See for example, *Remington: The Science and Practice of Pharmacy*, $20^{th}$ Edition (2000). Where the use environment is in vitro, "administration" refers to placement or delivery of the dosage form to the in vitro test medium. Where release of drug into the stomach is not desired but release of the drug in the duodenum or small intestine is desired, the use environment may also be the duodenum or small intestine. In such cases, "introduction" to a use environment is that point in time when the dosage form leaves the stomach and enters the duodenum.

The inventors have found that the bioavailability of CETP inhibitors may be substantially improved by forming a solid amorphous dispersion of the CETP inhibitor and an acidic concentration-enhancing polymer. The administration of the CETP inhibitor in the form of a solid amorphous dispersion containing a concentration-enhancing polymer substantially increases the concentration of dissolved CETP inhibitor in the use environment relative to administration of the CETP inhibitor in crystalline form. In particular, the use of certain acidic concentration-enhancing polymers has yielded substantial improvements in bioavailability.

However, when an HMG-CoA reductase inhibitor is mixed directly with a solid amorphous dispersion of the CETP inhibitor and acidic concentration-enhancing polymer and then granulated in a tableting formulation, the inventors observe chemical degradation of the HMG-CoA reductase inhibitor that is greater than that observed for the HMG-CoA reductase inhibitor alone. The inventors solved the chemical degradation problem by substantially physically separating the solid amorphous dispersion from the HMG-CoA reductase inhibitor while keeping the dispersion and the HMG-CoA reductase inhibitor in a unitary dosage form. The inventors believe that the chemical degradation was caused by the acidic concentration-enhancing polymer or indirectly by migration of the acid to the surface of the HMG-CoA reductase inhibitor. Surprisingly, the inventors found that the chemical stability of the HMG-CoA reductase inhibitor in the unitary dosage form could be improved by granulating the CETP inhibitor solid amorphous dispersion separately from the HMG-CoA reductase inhibitor. Without wishing to be bound by a particular theory, the inventors believe that when the granules comprising the solid amorphous dispersion and granulation excipients are blended with the HMG-CoA reductase inhibitor and then compressed into a tablet, the solid amorphous dispersion is substantially separated from the HMG-CoA reductase inhibitor, thus stabilizing the HMG-CoA reductase inhibitor. Alternatively, other methods may be used to separate the solid amorphous dispersion from the HMG-CoA reductase inhibitor. In addition, the basic nature of the HMG-CoA reductase inhibitor itself, when, for example, it is a basic salt form, or the presence of one or more basic excipients may be used to shield the HMG-CoA reductase inhibitor from the acidic environment created by the solid amorphous dispersion.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIGS. 1-8 are schematic drawings of cross sections of exemplary embodiments of dosage forms of the present invention.

DETAILED DESCRIPTION OF THE PRESENT INVENTION

Figure 3:
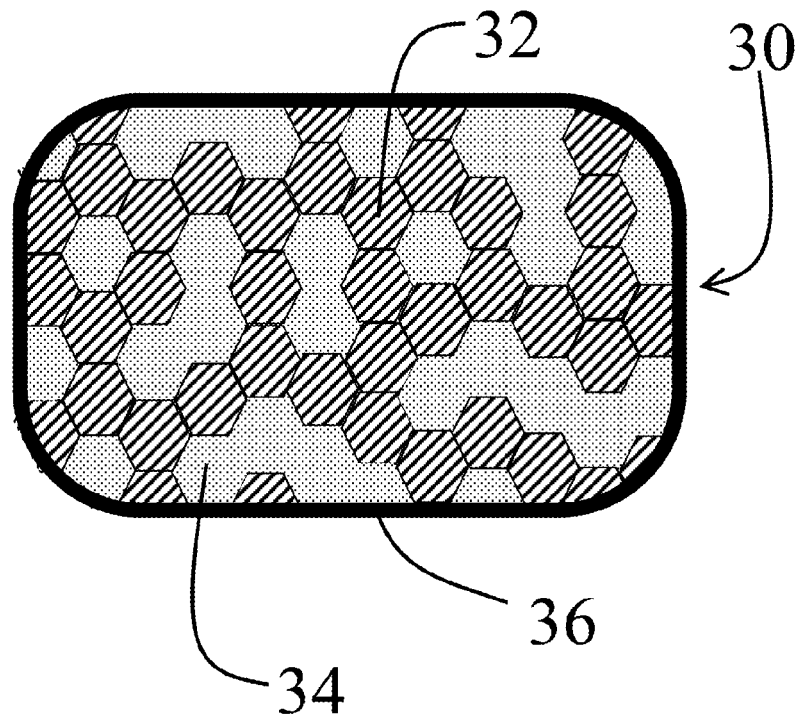

The present invention combines a CETP inhibitor and an HMG-CoA reductase inhibitor in a unitary dosage form. The CETP inhibitor is in the form of a solid amorphous dispersion comprising an acidic concentration-enhancing polymer. The solid amorphous dispersion is combined with the HMG-CoA reductase inhibitor so that the solid amorphous dispersion and the HMG-CoA reductase inhibitor are substantially separate from one another in the dosage form. Unitary dosage forms, solid amorphous dispersions, drugs, excipients, and methods for forming the dosage forms are discussed in more detail below.

Unitary Dosage Forms in which the CETP Inhibitor and HMG-CoA Reductase Inhibitor are Substantially Separate The unitary dosage forms of the present invention comprise (1) a CETP inhibitor composition comprising a solid amorphous dispersion comprising a CETP inhibitor and an acidic concentration-enhancing polymer, and (2) an HMG-CoA reductase inhibitor composition comprising the HMG-CoA reductase inhibitor. The two compositions are combined such that the solid amorphous dispersion and the HMG-CoA reductase inhibitor are substantially separate from one another in the dosage form. The solid amorphous dispersion and the HMG-CoA reductase inhibitor should be substantially physically separated, so that the acidic concentration-enhancing polymer does not cause unacceptable levels of chemical degradation of the HMG-CoA reductase inhibitor. The resulting unitary dosage form has improved chemical stability when compared to a control dosage form where the solid amorphous dispersion and the HMG-CoA reductase inhibitor are not substantially separate from one another.

The HMG-CoA reductase inhibitor and the acidic concentration-enhancing dispersion polymer are substantially physically separated in the dosage form. This means that the fraction of HMG-CoA reductase inhibitor molecules in contact with the acidic concentration-enhancing polymer in the solid amorphous dispersion is sufficiently small so that the acidic environment generated by the acidic concentration-enhancing polymer does not lead to unacceptable levels of chemical degradation of the HMG-CoA reductase inhibitor. Separation of the HMG-CoA reductase inhibitor and the acidic concentration-enhancing polymer results in improved chemical stability of the HMG-CoA reductase inhibitor in the dosage form.

Several different methods may be used to separate the solid amorphous dispersion and HMG-CoA reductase inhibitor. In one method, the solid amorphous dispersion is granulated with optional granulation excipients into a CETP inhibitor granulation and then mixed with an HMG-CoA reductase inhibitor composition. When the acidic concentration-enhancing polymer is present in a granule, the amount of acidic concentration-enhancing polymer on the surface of the granule, which can potentially be in contact with the HMG-CoA reductase inhibitor composition, is low due to the decrease in the surface to volume ratio resulting from the use of a large granule compared with a smaller solid amorphous dispersion particle. In addition, the optional granulation excipients reduce the amount of acidic concentration-enhancing polymer on the outside surface of the granule. As a result, when the granules are mixed with an HMG-CoA reductase inhibitor composition, the HMG-CoA reductase inhibitor and the acidic concentration-enhancing polymer are substantially separate, resulting in improved chemical stability of the HMG-CoA reductase inhibitor.

Thus, in one aspect, a unitary dosage form is provided in which the solid amorphous dispersion of the CETP inhibitor and acidic concentration-enhancing polymer is granulated and then mixed with the HMG-CoA reductase inhibitor, shown schematically as dosage form 10 in FIG. 1. Granules 12 comprising the solid amorphous dispersion of the CETP inhibitor and acidic concentration-enhancing polymer and optional granulation excipients are interspersed within the HMG-CoA reductase inhibitor composition 14. The solid amorphous dispersion within the granules are substantially separate from the HMG-CoA reductase inhibitor. Dosage form 10 may optionally be coated with a conventional coating 16.

Alternatively, the HMG-CoA reductase inhibitor may be granulated with optional granulation excipients and mixed with a CETP inhibitor composition. Thus, in another aspect, a unitary dosage form is provided in which the HMG-CoA reductase inhibitor is granulated and then mixed with the solid amorphous dispersion of the CETP inhibitor and acidic concentration-enhancing polymer, shown schematically as dosage form 20 in FIG. 2. Granules 24 comprising the HMG-CoA reductase inhibitor and optional granulation excipients are interspersed within the CETP inhibitor composition 22. The HMG-CoA reductase inhibitor particles in the granules are substantially separate from the solid amorphous dispersion in the CETP inhibitor composition. Dosage form 20 may optionally be coated with a conventional coating 26.

In another method, the solid amorphous dispersion may be granulated with optional granulation excipients into a CETP inhibitor granulation and the HMG-CoA reductase inhibitor may be granulated with optional granulation excipients into an HMG-CoA reductase inhibitor granulation and the two granulations blended together. Thus, in another aspect, a unitary dosage form comprises a first granulation comprising the solid amorphous dispersion of the CETP inhibitor and the acidic concentration-enhancing polymer mixed with a second granulation comprising the HMG-CoA reductase inhibitor, shown schematically as dosage form 30 in FIG. 3. Here, the CETP inhibitor granulation 32 is mixed with the HMG-CoA reductase inhibitor granulation 34. Surprisingly, the inventors have found that the stability of the HMG-CoA reductase inhibitor may be maintained by mixing the two granulations together. In contrast, granulating the solid amorphous dispersion, HMG-CoA reductase inhibitor, and other excipients all together yields a composition in which the HMG-CoA reductase inhibitor chemically degrades. Dosage form 30 may optionally be coated with a conventional coating 36.

As yet another method, the CETP inhibitor composition comprises a solid amorphous dispersion coated with a material that is not acidic. This composition is mixed with an HMG-CoA reductase inhibitor composition, so as to prevent contact of the solid amorphous dispersion with the HMG-CoA reductase inhibitor. Alternatively, the HMG-CoA reductase inhibitor composition may be coated with a material that is not acidic and then mixed with the CETP inhibitor composition, so as to prevent contact of the solid amorphous dispersion with the HMG-CoA reductase inhibitor. In either case, the coating is sufficiently thick to ensure the HMG-CoA reductase inhibitor and the solid amorphous dispersion are substantially separate, resulting in improved chemical stability.

Figure 4:
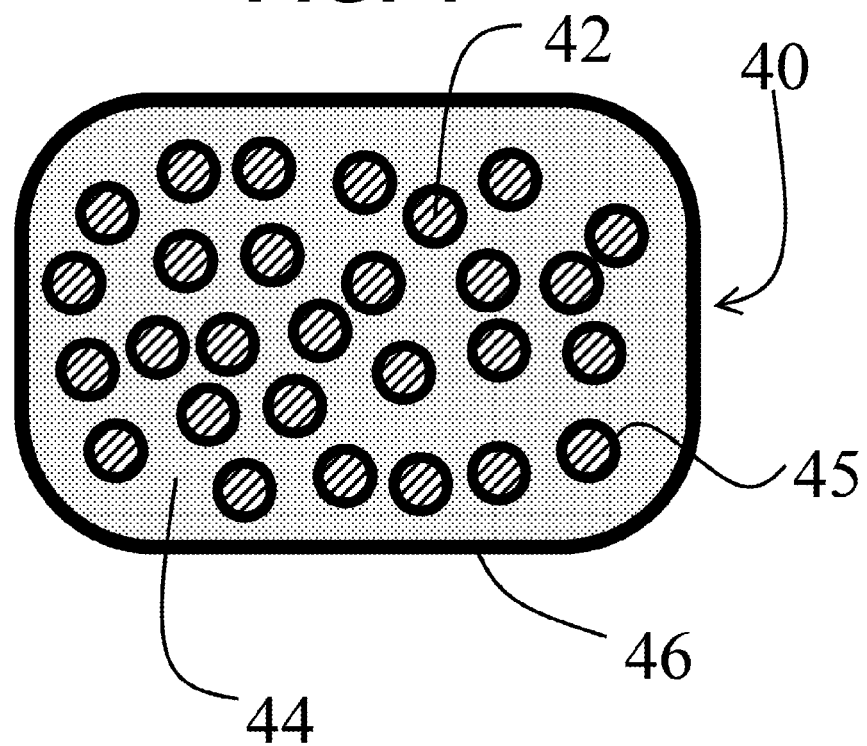

Thus, in one aspect, a unitary dosage form is provided in which the CETP inhibitor composition comprises a solid amorphous dispersion coated with a coating and blended with the HMG-CoA reductase inhibitor, shown schematically as dosage form 40 in FIG. 4. The solid amorphous dispersion 42 is coated with a coating 45. In one embodiment, the solid amorphous dispersion is coated with a protective coating that is not acidic. The coating substantially separates the solid amorphous dispersion from the HMG-CoA reductase inhibitor. The coating may be any conventional coating that does not contain acidic groups, or other material that would adversely interact with either the solid amorphous dispersion or the HMG-CoA reductase inhibitor. The coated solid amorphous dispersion is then mixed with the HMG-CoA reductase inhibitor composition 44. Dosage form 40 may optionally be coated with a conventional coating 46.

In another aspect, a unitary dosage form is provided in which the HMG-CoA reductase inhibitor composition comprises an HMG-CoA reductase inhibitor coated with a non-acidic coating. The HMG-CoA reductase inhibitor composition is then blended with the solid amorphous dispersion, shown schematically as dosage form 50 in FIG. 5. The HMG-CoA reductase inhibitor 54 is coated with a coating 55. The coating substantially separates the solid amorphous dispersion from the HMG-CoA reductase inhibitor. The coating may be any conventional coating that does not contain acidic groups, or other material that would adversely interact with either the solid amorphous dispersion or the HMG-CoA reductase inhibitor. The coated HMG-CoA reductase inhibitor is then mixed with the solid amorphous dispersion 52. Dosage form 50 may optionally be coated with a conventional coating 56.

Figure 6:
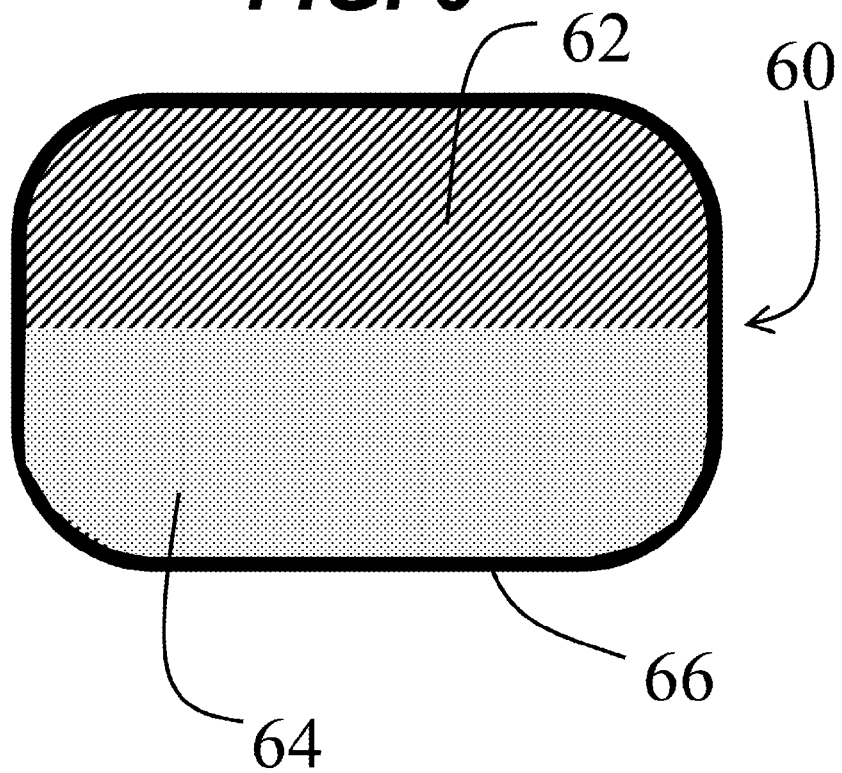

As yet another method, the CETP inhibitor composition and the HMG-CoA reductase inhibitor composition may be formed into separate regions or volumes of the dosage form, such as separate layers. Thus, in one aspect, a unitary dosage form is provided in which the CETP inhibitor composition and the HMG-CoA reductase inhibitor composition are in separate layers or volumes within the dosage form. In one embodiment, the dosage form is a bi-layer tablet, shown schematically as dosage form 60 in FIG. 6. The dosage form 60 has a first layer 62 consisting of the CETP inhibitor composition, and a second layer 64 consisting of the HMG-CoA reductase inhibitor composition. The dosage form 60 may optionally be coated with a conventional coating 66. The layers 62 and 64 may be formed by any conventional method, as described below. By separating the CETP inhibitor composition and the HMG-CoA reductase inhibitor composition into two separate layers, the solid amorphous dispersion and HMG-CoA reductase inhibitor are substantially separate from one another. This results in acceptably low rates of degradation of the HMG-CoA reductase inhibitor.

Figure 7:
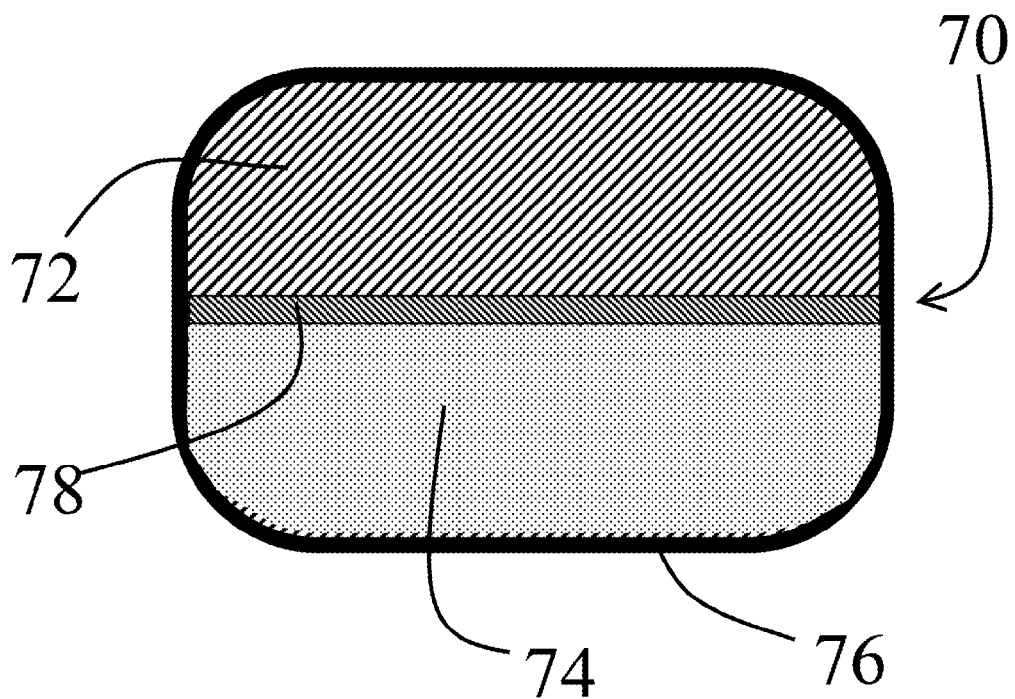

Another embodiment of a unitary dosage form is a trilayer dosage form having three layers. FIG. 7 shows schematically a trilayer dosage form 70 having layers 72, 74 and 78. One or more of layers 72, 74 and 78 may be the CETP inhibitor composition, and one or more of layers 72, 74, and 78 may be the HMG-CoA reductase inhibitor composition. Trilayer dosage forms may be formed by any conventional method, as described below. Again, by separating the CETP inhibitor composition and the HMG-CoA reductase inhibitor composition into separate layers, the solid amorphous dispersion and HMG-CoA reductase inhibitor are substantially separate from one another, resulting in acceptably low rates of degradation of the HMG-CoA reductase inhibitor. Dosage form 70 may optionally be coated with a conventional coating 76.

In a specific embodiment of the trilayer dosage form 70, layer 78 comprises a non-acidic barrier layer, separating the CETP inhibitor composition 72 from the HMG-CoA reductase inhibitor composition 74. The barrier layer ensures the solid amorphous dispersion and HMG-CoA reductase inhibitor are substantially separate from one another, resulting in acceptably low rates of degradation of the HMG-CoA reductase inhibitor.

In another embodiment (not shown), the unitary dosage form has more than three layers. At least one layer is the CETP inhibitor composition, and at least one layer is the HMG-CoA reductase inhibitor composition. Optionally, at least one of the layers is a non-acidic barrier layer. The layers are arranged so that the solid amorphous dispersion and HMG-CoA reductase inhibitor are substantially separate from one another.

Figure 8:
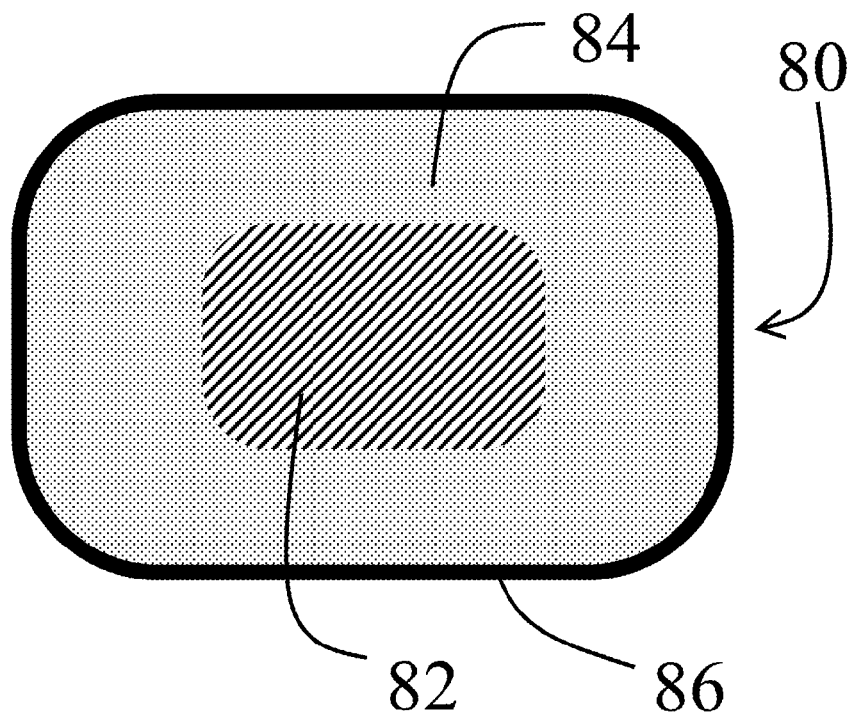

Yet another embodiment of a unitary dosage form is a concentric core dosage form having a central core and an outer layer surrounding the core. FIG. 8 shows schematically a dosage form 80 having a central core 82 and a layer 84 surrounding the core 82. The CETP inhibitor composition may be in the central core 82 with the HMG-CoA reductase inhibitor composition in the surrounding layer 84, or the HMG-CoA reductase inhibitor composition may be in the central core 82 with the CETP inhibitor composition in the surrounding layer 84. By separating the CETP inhibitor composition and the HMG-CoA reductase inhibitor composition into separate volumes, the solid amorphous dispersion and HMG-CoA reductase inhibitor are substantially separate from one another, resulting in acceptably low rates of degradation of the HMG-CoA reductase inhibitor. The central core may optionally be coated with a non-acidic protective coating to ensure the solid amorphous dispersion and HMG-CoA reductase inhibitor are substantially separate from one another. Dosage form 80 may optionally be coated with a conventional coating 86.

The unitary dosage form may be in the form of a tablet, caplet, pill, capsule, powder or other dosage form known in the art. In one embodiment, the CETP inhibitor composition and HMG-CoA reductase inhibitor composition are blended together and then compressed to form a tablet, caplet, pill, or other dosage forms formed by compression forces known in the art. Examples of suitable tablets are shown in FIGS. 1-8.

Yet another embodiment of the unitary dosage form is a capsule. The CETP inhibitor composition and the HMG-CoA reductase inhibitor composition are mixed and placed into a suitable capsule, such as a hard gelatin capsule or a soft gelatin capsule, well known in the art (see, for example, *Remington's Pharmaceutical Sciences*, (18th ed. 1990)). The compositions are formed such that the solid amorphous dispersion and the HMG-CoA reductase inhibitor are substantially separate in the dosage form. In one embodiment, the CETP inhibitor composition is first granulated and then mixed with the HMG-CoA reductase inhibitor composition and the mixture placed into a capsule. In another embodiment, the HMG-CoA reductase inhibitor composition is first granulated and then mixed with the CETP inhibitor composition and the mixture placed into a capsule. In yet another embodiment, the CETP inhibitor composition is granulated and mixed with a granulation of the HMG-CoA reductase inhibitor composition. In still another embodiment, the CETP inhibitor composition comprises a solid amorphous dispersion that has been coated with a protective coating. The coated solid amorphous dispersion is then mixed with the HMG-CoA reductase inhibitor composition and the mixture placed into a capsule. In yet another embodiment, the HMG-CoA reductase inhibitor composition comprises coated HMG-CoA reductase inhibitor particles. The coated particles are mixed with the CETP inhibitor composition and the mixture placed into a capsule. In yet another embodiment, the HMG-CoA reductase inhibitor composition comprises a compressed tablet comprising the HMG-CoA reductase inhibitor and optional excipients. The HMG-CoA reductase inhibitor tablet is placed into a capsule with a CETP inhibitor composition. In yet another embodiment, the CETP inhibitor composition comprises a compressed tablet comprising the solid amorphous dispersion and optional excipients. The CETP inhibitor tablet is placed into a capsule with an HMG-CoA reductase inhibitor composition.

Yet another embodiment of the unitary dosage form is a powder, often referred to in the art as a sachet or oral powder for constitution (OPC). The CETP inhibitor composition and the HMG-CoA reductase inhibitor composition are mixed and placed into a suitable container, such as a pouch, bottle, box, bag, or other container known in the art. The compositions are formed such that the solid amorphous dispersion and the HMG-CoA reductase inhibitor are substantially separate in the dosage form, as described above. The powder dosage form can then be taken dry or mixed with a liquid to form a paste, suspension or slurry prior to dosing.

Yet another embodiment of the unitary dosage form is a kit comprising two separate compositions: (1) one containing the solid amorphous dispersion comprising a CETP inhibitor and an acidic concentration-enhancing polymer, and (2) one containing the HMG-CoA reductase inhibitor. The kit is designed such that the HMG-CoA reductase inhibitor and the solid amorphous dispersion are substantially separate. The kit includes means for containing the separate compositions such as a divided bottle or a divided foil packet; however, the separate compositions may also be contained within a single, undivided container. Typically the kit includes directions for the administration of the separate components.

Chemical Stability

Dosage forms in which the solid amorphous dispersion and HMG-CoA reductase inhibitor are substantially separate from one another exhibit acceptably low rates of degradation of the HMG-CoA reductase inhibitor in the dosage form. The compositions and dosage forms of the present invention provide improved chemical stability of the HMG-CoA reductase inhibitor relative to a control composition consisting of an equivalent quantity of the solid amorphous dispersion and HMG-CoA reductase inhibitor wherein the solid amorphous dispersion and the HMG-CoA reductase inhibitor is not substantially separate, as described in detail below.

In general, degradation of the HMG-CoA reductase inhibitor may be measured using any conventional method for measuring the potency or purity of drug in a pharmaceutical composition. For example, the amount of active HMG-CoA reductase inhibitor present in a composition may be initially measured using high-performance liquid chromatography (HPLC) or other analytical techniques well known in the art. Alternatively, the amount of HMG-CoA reductase inhibitor initially present may be calculated from the amount of drug present in the composition. The potency of the composition is then measured after storage at controlled temperature and humidity conditions for an appropriate period of time. A decrease in potency indicates that a chemical reaction has occurred, leading to a decrease in the amount of active drug present in the corm position, and is an indication of poor chemical stability.

An alternative method used to evaluate chemical stability is to analyze the rate of increase in the amount of drug degradant(s) in the composition, which would indicate reaction of the HMG-CoA reductase inhibitor. An HPLC or other analytical technique may be used to determine the concentration of drug degradant(s) in a composition. The amount of the degradant(s) is measured before and after storage under controlled storage conditions. The amount of increase in the drug degradant(s) may be used to determine the amount of decrease in "percent drug purity," defined as 100 times the total amount of drug present divided by the amount of drug initially present. Thus, percent drug purity may be calculated as follows:

$$\text{percent drug purity} = 100 \times \left( \frac{\text{total drug present}}{\text{drug initially present}} \right)$$

When the drug purity is calculated from the total amount of impurities, percent drug purity may be calculated by assuming that the drug initially present, given in wt %, is equal to 100 wt % minus the wt % of total initial impurities, and that total drug present is equal to 100 wt % minus the wt % of total impurities after storage, that is, at some later time. This method of calculating percent drug purity is by the formula:

$$\text{percent drug purity} = 100 \times \left[ 1 - \left( \frac{\text{total impurities}}{\text{drug initially present}} \right) \right]$$

The rate at which drug degradation occurs is generally dependent on the storage conditions. The HMG-CoA reductase inhibitor, when formulated in a composition of the present invention, should be stable at ambient temperature and humidity conditions (e.g., 20% to 60% relative humidity (RH)) for long periods of time, such as months or years. However, to expedite testing, the storage conditions may employ elevated temperature and/or humidity to simulate longer storage times at ambient conditions. The storage time may vary from a few days to weeks or months, depending on the reactivity of the drug and the storage conditions.

A "degree of degradation" of drug following storage may be determined by subtracting the final percent drug purity (determined either by measuring the decrease in drug present or the increase in drug impurities present) from the initial percent drug purity. For example, a sample of composition initially containing 100 mg HMG-CoA reductase inhibitor and having no measurable impurities would have an initial percent drug purity of 100 wt %. If, after storage, the amount of HMG-CoA reductase inhibitor in the sample decreases to 95 mg, the final percent drug purity would be 95 wt % and the degree of degradation would be 100 wt % less 95 wt %, or 5 wt %. Alternatively, if 100 mg of HMG-CoA reductase inhibitor were found to initially have 1 mg of impurities present, it would have an initial percent drug purity of 99 wt %. If, after storage, the total impurities present had increased to 6 wt %, the final percent drug purity would be 94 wt % and the degree of degradation would be 99 wt % less 94 wt %, or 5 wt %.

Alternatively, degree of degradation can be determined by subtracting the amount of one or more specific drug degradants initially present from the amount of that specific degradant present after storage. Such a measure is useful where there are several drug degradants, of which only one or a few are of concern. For example, if an HMG-CoA reductase inhibitor initially contained a specific degradant at a concentration of 1 wt % and after storage the concentration of that degradant was 6 wt %, the degree of degradation would be 6 wt % less 1 wt %, or 5 wt %.

A relative degree of improvement in chemical stability of the HMG-CoA reductase inhibitor in a test composition may be determined by taking the ratio of the degree of degradation of the HMG-CoA reductase inhibitor in a control composition and the degree of degradation of the HMG-CoA reductase inhibitor in a test composition under the same storage conditions for the same storage time period. The test composition is simply the composition of the solid amorphous dispersion of the CETP inhibitor and acidic concentration-enhancing polymer, the HMG-CoA reductase inhibitor, and optional additional excipients, in which the unitary dosage form is prepared so that the solid amorphous dispersion and the HMG-CoA reductase inhibitor are substantially separate from one another. The control composition is simply the same amount of the solid amorphous dispersion of the CETP inhibitor and acidic concentration-enhancing polymer, the HMG-CoA reductase inhibitor, and optional additional excipients, in which the solid amorphous dispersion, HMG-CoA reductase inhibitor and optional additional excipients are blended together in a single step and then compressed to form a slug. The slug may-be milled to a smaller granule to ease testing of the control composition. For example, where the degree of degradation of the HMG-CoA reductase inhibitor in a test composition is 1 wt %, and the degree of degradation of the HMG-CoA reductase inhibitor in a control composition is 5 wt %, the relative degree of improvement is 5 wt %/1 wt % equals 5.0. For compositions and dosage forms in which the HMG-CoA reductase inhibitor and solid amorphous dispersion are substantially separate from one another, the relative degree of improvement is at least 1.1. Preferably, the relative degree of improvement is at least 1.25, more preferably at least 2.0, and even more preferably at least 3.0, more preferably at least 5.0. In fact, some compositions of the present invention may achieve a relative degree of improvement greater than 20.

The particular storage conditions and time of storage may be chosen as convenient depending on the degree of acid-sensitivity of the HMG-CoA reductase inhibitor, the particular acidic concentration-enhancing polymer used in the solid amorphous dispersion, and the ratio of HMG-CoA reductase inhibitor to polymer in the composition. Where the HMG-CoA reductase inhibitor is particularly acid-sensitive, or where the composition has a low ratio of HMG-CoA reductase inhibitor to polymer, then shorter storage time periods may be used. Where the rate of degradation is linear, the relative degree of improvement will be independent of the storage time. However, where the rate of degradation is non-linear under controlled storage conditions, the stability test used to compare the test composition with the control composition is preferably chosen such that the degree of degradation is sufficiently large that it may be accurately measured. Typically, the time period is chosen so as to observe a degree of degradation in the control composition of at least 0.1 wt % to 0.2 wt %. However, the time period is not so long that the ratio of HMG-CoA reductase inhibitor to polymer changes substantially. Typically, the time period is such that the observed degree of degradation for the test composition is less than 50 wt % and preferably less than 20 wt %. When rate of degradation in the control composition is relatively slow, the test is preferably conducted over a long enough period of time under controlled storage conditions to allow a meaningful comparison of the stability of the test composition with the control composition.

A stability test which may be used to test whether a composition or dosage form meets the chemical stability criteria described above is storage of the test dispersion and the control dispersion for six months at 40° C. and 75% relative humidity (RH) or for 3 months at 50°C and 75% RH. A relative degree of improvement may become apparent within a shorter time, such as three to five days, and shorter storage times may be used for some very acid-sensitive HMG-CoA reductase inhibitors. When comparing dispersions under storage conditions that approximate ambient conditions, e.g., 30° C. and 60% RH, the storage period may need to be several months or up to two years.

In addition, it is preferred that the compositions comprising an HMG-CoA reductase inhibitor and a solid amorphous dispersion result in chemical stability such that the HMG-CoA reductase inhibitor has a degree of degradation of less than about 5 wt %, more preferably less than about 2 wt %, even more preferably less than about 0.5 wt %, and most preferably less than about 0.1 wt % when stored at 40° C. and 75% RH for six months, or less than about 5 wt %, more preferably less than about 2 wt %, even more preferably less than about 0.5 wt %, and more preferably less than about 0.1 wt %, when stored at 30° C. and 60% RH for one year. Nevertheless, the compositions of the present invention may have a degree of degradation that is much greater than the preferred values, so long as the solid amorphous dispersion achieves the degree of improvement relative to a control composition as described above.

Cholesteryl Ester Transfer Protein Inhibitors

The CETP inhibitor may be any compound capable of inhibiting the cholesteryl ester transfer protein. Solid amorphous dispersions are particularly useful for CETP inhibitors that have sufficiently low aqueous solubility, low bioavailability or slow rate of absorption such that it is desirable to increase their concentration in an aqueous environment of use. The CETP inhibitor is typically "sparingly water-soluble," which means that the CETP inhibitor has a minimum aqueous solubility of less than about 1 to 2 mg/mL at any physiologically relevant pH (e.g., pH 1-8) and at about 22° C. Many CETP inhibitors are "substantially water-insoluble," which means that the CETP inhibitor has a minimum aqueous solubility of less than about 0.01 mg/mL (or 10 μg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 10 μg/mL, and even more preferred for CETP inhibitors with solubilities less than about 1 μg/mL. Many CETP inhibitors have even lower solubilities (some even less than 0.1 μg/mL), and require dramatic concentration enhancement to be sufficiently bioavailable upon oral dosing for effective plasma concentrations to be reached at practical doses.

In general, the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios greater than 1000 mL, and more preferred for dose-to-solubility ratios greater than about 5000 ml. The dose-to-solubility ratio may be determined by dividing the dose (in mg) by the aqueous solubility (in mg/ml).

Oral delivery of many CETP inhibitors is particularly difficult because their aqueous solubility is usually extremely low, typically being less than 2 µg/ml, often being less than 0.1 µg/ml. Such low-solubilities are a direct consequence of the particular structural characteristics of species that bind to CETP and thus act as CETP inhibitors. This low solubility is primarily due to the hydrophobic nature of CETP inhibitors. Log P, defined as the base 10 logarithm of the ratio of the drug solubility in octanol to the drug solubility in water, is a widely accepted measure of hydrophobicity. Log P may be measured experimentally or calculated using methods known in the art. Calculated Log P values are often referred to by the calculation method, such as Alog P, Clog P, and Mlog P. In general, Log P values for CETP inhibitors are greater than 4 and are often greater than 5. Thus, the hydrophobic and insoluble nature of CETP inhibitors as a class pose a particular challenge for oral delivery. Achieving therapeutic drug levels in the blood by oral dosing of practical quantities of drug generally requires a large enhancement in drug concentrations in the gastrointestinal fluid and a resulting large enhancement in bioavailability. Such enhancements in drug concentration in gastrointestinal fluid typically need to be at least about 10-fold and often at least about 50-fold or even at least about 200-fold to achieve desired blood levels. Surprisingly, the solid amorphous dispersions of the present invention have proven to have the required large enhancements in drug concentration and bioavailability.

In contrast to conventional wisdom, the relative degree of enhancement in aqueous concentration and bioavailability provided by the solid amorphous dispersions generally improves for CETP inhibitors as solubility decreases and hydrophobicity increases. In fact, the inventors have recognized a subclass of these CETP inhibitors that are essentially aqueous insoluble, highly hydrophobic, and are characterized by a set of physical properties. This subclass exhibits dramatic enhancements in aqueous concentration and bioavailability when formulated using a solid amorphous dispersion.

The first property of this subclass of essentially insoluble, hydrophobic CETP inhibitors is extremely low aqueous solubility. By extremely low aqueous solubility is meant that the minimum aqueous solubility at physiologically relevant pH (pH of 1 to 8) is less than about 10 µg/ml and preferably less than about 1 µg/ml.

A second property is a very high dose-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic CETP inhibitors is a very high dose (in mg) to solubility (in mg/ml) ratio (ml). By "very high dose-to-solubility ratio" is meant that the dose-to-solubility ratio has a value of at least 1000 ml, and preferably at least 5,000 ml, and more preferably at least 10,000 ml.

A third property of this subclass of essentially insoluble, hydrophobic CETP inhibitors is that they are extremely hydrophobic. By extremely hydrophobic is meant that the Log P value of the drug, has a value of at least 4.0, preferably a value of at least 5.0, and more preferably a value of at least 5.5.

A fourth property of this subclass of essentially insoluble CETP inhibitors is that they have a low melting point. Generally, drugs of this subclass will have a melting point of about 150° C. or less, and preferably about 140° C. or less.

Primarily, as a consequence of some or all of these four properties, CETP inhibitors of this subclass typically have very low absolute bioavailabilities. Specifically, the absolute bioavailability of drugs in this subclass when dosed orally in their undispersed state is less than about 10% and more often less than about 5%.

For this subclass of CETP inhibitors, the CETP inhibitor, when dispersed in the solid amorphous dispersion, should be at least substantially amorphous, and more preferably is almost completely amorphous, as described below. In addition, the solid amorphous dispersion should be substantially homogeneous. As discussed below, such dispersions may be made by mechanical processes, such as milling and extrusion; melt processes, such as fusion, melt-extrusion, and melt-congealing; and solvent processes, such as non-solvent precipitation, spray coating, and spray-drying. When prepared in this fashion, this class of essentially insoluble, hydrophobic CETP inhibitors often exhibits dramatic enhancements in aqueous concentration in the use environment and in bioavailability when dosed orally. While the degree of enhancement will depend on the particular concentration-enhancing polymer, when preferred concentration-enhancing polymers are used (as discussed below), such compositions may provide a maximum drug concentration (MDC) in an aqueous use environment that is at least about 50-fold, and preferably at least about 200-fold, the equilibrium concentration of a control composition comprising an equivalent quantity of the essentially insoluble, hydrophobic CETP inhibitor but free from the concentration-enhancing polymer. Likewise, the compositions also display in an aqueous use environment an area under the concentration versus time curve (AUC), for any period of at least 90 minutes between the time of introduction into the use environment and about 270 minutes following introduction into the use environment that is at least about 25-fold, and preferably at least about 100-fold, that of the control composition comprising an equivalent quantity of drug but free from the concentration-enhancing polymer.

In the following, by "pharmaceutically acceptable forms" thereof is meant any pharmaceutically acceptable derivative or variation, including stereoisomers, stereoisomer mixtures, enantiomers, solvates, hydrates, isomorphs, polymorphs, salt forms and prodrugs.

One class of CETP inhibitors that finds utility with the present invention consists of oxy substituted 4-carboxyamino-2-methyl-1,2,3,4-tetrahydroquinolines having the Formula I

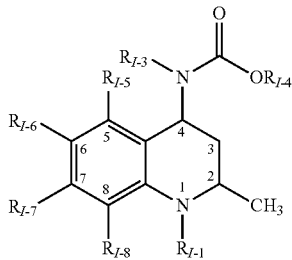

Formula I and pharmaceutically acceptable forms thereof;

wherein $R_{I-1}$ is hydrogen, $Y_I$, $W_I$—$X_I$, $W_I$—$Y_I$;

wherein $W_I$ is a carbonyl, thiocarbonyl, sulfinyl or sulfonyl;

$X_I$ is —O—$Y_I$, —S—$Y_I$, —N(H)—Y, or —N—$(Y_I)_2$;

wherein $Y_I$ for each occurrence is independently $Z_I$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_I$;

wherein $Z_I$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_I$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxyl, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxyl, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{I-3}$ is hydrogen or $Q_I$;

wherein $Q_I$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_I$;

wherein $V_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_I$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carbamoyl, mono-N— or di-N,N—$(C_1-C_6)$ alkylcarbamoyl, carboxyl, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxyl, $(C_1-C_6)$alkyloxycarbonyl, mono-N— or di-N,N—$(C_1-C_6)$alkylamino, said $(C_1-C_6)$alkyl or $(C_2-C_6)$alkenyl substituents are also optionally substituted with from one to nine fluorines;

$R_{I-4}$ is $Q_{I-1}$ or $V_{I-1}$ wherein $Q_{I-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{I-1}$;

wherein $V_{I-1}$ is a partially saturated, fully saturated or fully unsaturated three to six membered ring optionally having one to two heteroatoms selected independently from oxygen, sulfur and nitrogen;

wherein said $V_{I-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{I-3}$ must contain $V_I$ or $R_{I-4}$ must contain $V_{I-1}$; and $R_{I-5}$, $R_{I-6}$, $R_{I-7}$ and $R_{I-8}$ are each independently hydrogen, hydroxy or oxy wherein said oxy is substituted with $T_I$ or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_I$;

wherein $T_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_I$ substituent is optionally mono-, di- or tri-substituted independently with halo, $(C_1$-$C_6)$alkyl, $(C_2$-$C_6)$alkenyl, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N or di-N,N—$(C_1$-$C_6)$alkylamino wherein said $(C_1$-$C_6)$alkyl substituent is optionally mono-, di- or tri-substituted independently with hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N— or di-N,N—$(C_1$-$C_6)$alkylamino, said $(C_1$-$C_6)$alkyl substituent is also optionally substituted with from one to nine fluorines.

Compounds of Formula I are disclosed in commonly assigned U.S. Pat. No. 6,140,342, the complete disclosure of which is herein incorporated by reference.

In a preferred embodiment, the CETP inhibitor is selected from one of the following compounds of Formula I:

[2R,4S]4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S]4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S]4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6-methoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-7-methoxy-2-methyl-3,4-dihydro-2H-quinoline-1-carboxylic acid ethyl ester,

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;

[2R,4S]4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid propyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;

[2R,4S]4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester,

[2R,4S] (3,5-bis-trifluoromethyl-benzyl)-(1-butyryl-6,7-dimethoxy-2-methyl-1,2,3,4-tetrahydro-quinolin-4-yl)-carbamic acid methyl ester;

[2R,4S] (3,5-bis-trifluoromethyl-benzyl)-(1-butyl-6,7-dimethoxy-2-methyl-1,2,3,4-tetrahydro-quinolin-4-yl)-carbamic acid methyl ester;

[2R,4S] (3,5-bis-trifluoromethyl-benzyl)-[1-(2-ethyl-butyl)-6,7-dimethoxy-2-methyl-1,2,3,4-tetrahydro-quinolin-4-yl]-carbamic acid methyl ester, hydrochloride Another class of CETP inhibitors that finds utility with the present invention consists of 4-carboxyamino-2-methyl-1,2,3,4,-tetrahydroquinolines, having the Formula II

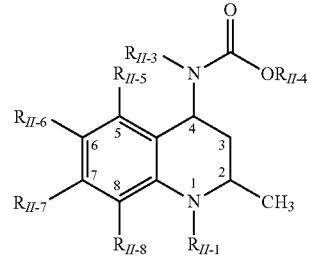

Formula II and pharmaceutically acceptable forms thereof;

wherein $R_{II-1}$, is hydrogen, $Y_{II}$, $W_{II}$—$X_{II}$, $W_{II}$—$Y_{II}$;

wherein $W_{II}$ is a carbonyl, thiocarbonyl, sulfinyl or sulfonyl;

$X_{II}$ is —O—$Y_{II}$, —S—$Y_{II}$, —N(H)—$Y_{II}$, or —N—$(Y_{II})_2$;

wherein $Y_{II}$ for each occurrence is independently $Z_{II}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{II}$;

$Z_{II}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{II}$ substituent is optionally mono-, di- or tri-substituted independently with halo, $(C_2$-$C_6)$alkenyl, $(C_1$-$C_6)$alkyl, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N— or di-N,N—$(C_1$-$C_6)$alkylamino wherein said $(C_1$-$C_6)$alkyl substituent is optionally mono-, di- or tri-substituted independently with halo, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N— or di-N,N—$(C_1$-$C_6)$alkylamino, said $(C_1$-$C_6)$alkyl is also optionally substituted with from one to nine fluorines;

$R_{II-3}$ is hydrogen or $Q_{II}$;

wherein $Q_{II}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II}$;

wherein $V_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{II}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_2-C_6)$alkenyl substituents are optionally substituted with from one to nine fluorines;

$R_{II-4}$ is $Q_{II-1}$ or $V_{II-1}$ wherein $Q_{II-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II-1}$;

wherein $V_{II-1}$ is a partially saturated, fully saturated or fully unsaturated three to six membered ring optionally having one to two heteroatoms selected independently from oxygen, sulfur and nitrogen;

wherein said $V_{II-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_{1-6})$alkyl substituent is optionally mono-substituted with oxo, said $(C_1-C_6)$alkyl substituent is optionally substituted with from one to nine fluorines;

wherein either $R_{II-3}$ must contain $V_{II}$ or $R_{II-4}$ must contain $V_{II}$; and $R_{II-5}$, $R_{II-6}$, $R_{II-7}$ and $R_{II-8}$ are each independently hydrogen, a bond, nitro or halo wherein said bond is substituted with $T_{II}$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{II}$;

wherein $T_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{II}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; provided that at least one of substituents $R_{II-5}$, $R_{II-6}$, $R_{II-7}$ and $R_{II-8}$ is not hydrogen and is not linked to the quinoline moiety through oxy.

Compounds of Formula II are disclosed in commonly assigned U.S. Pat. No. 6,147,090, the complete disclosure of which is herein incorporated by reference.

In a preferred embodiment, the CETP inhibitor is selected from one of the following compounds of Formula II:

[2R,4S]4-[(3,5-Bis-trifluoromethyl-benzyl)-methoxycarbonyl-amino]-2-methyl-7-trifluoromethyl-3,4-dihydro-2H-quinoline-1-carboxylic acid ethyl ester;

[2R,4S]4-[(3,5-Bis-trifluoromethyl-benzyl)-methoxycarbonyl-amino]-7-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2,6,7-trimethyl-3,4-dihydro-2H-quinoline-1-carboxylic acid ethyl ester [2R,4S]4-[(3,5-Bis-trifluoromethyl-benzyl)-methoxycarbonyl-amino]-6,7-diethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-ethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2-methyl-6-trifluoromethyl-3,4-dihydro-2H-quinoline-1-carboxylic acid ethyl ester.

[2R,4S]4-[(3,5-bis-trifluoromethyl-benzyl)-methoxycarbonyl-amino]-2-methyl-6-trifluoromethyl-3,4-dihydro-2H-quinoline-1-carboxylic acid isopropyl ester.

Another class of CETP inhibitors that finds utility with the present invention consists of annulated 4-carboxyamino-2-methyl-1,2,3,4,-tetrahydroquinolines, having the Formula IIII

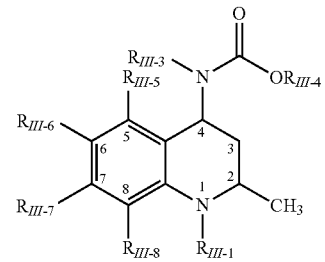

Formula III and pharmaceutically acceptable forms thereof;

wherein $R_{III-1}$ is hydrogen, $Y_{III}$, $W_{III}$—$X_{III}$, $W_{III}$—$Y_{III}$;

wherein $W_{III}$ is a carbonyl, thiocarbonyl, sulfinyl or sulfonyl;

$X_{III}$ is —O—$Y_{III}$, —S—$Y_{III}$, —N(H)—$Y_{III}$ or —N—$(Y_{III})_2$;

$Y_{III}$ for each occurrence is independently $Z_{III}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{III}$;

wherein $Z_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{III}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl optionally substituted with from one to nine fluorines;

$R_{III-3}$ is hydrogen or $Q_{III}$;

wherein $Q_{III}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III}$;

wherein $V_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{III}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_2-C_6)$alkenyl are optionally substituted with from one to nine fluorines;

$R_{III-4}$ is $Q_{III-1}$ or $V_{III-1}$;

wherein $Q_{III-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III-1}$;

wherein $V_{III-1}$, is a partially saturated, fully saturated or fully unsaturated three to six membered ring optionally having one to two heteroatoms selected independently from oxygen, sulfur and nitrogen;

wherein said $V_{III-1}$, substituent is optionally mono-, di-, tri-, or tetra-substituted independently with halo, $(C_1-C_6)$ alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent optionally having from one to nine fluorines;

wherein either $R_{III-3}$ must contain $V_{III}$ or $R_{III-4}$ must contain $V_{III-1}$; and $R_{III-5}$ and $R_{III-6}$, or $R_{III-6}$ and $R_{III-7}$, and/or $R_{III-7}$ and $R_{III-8}$ are taken together and form at least one four to eight membered ring that is partially saturated or fully unsaturated optionally having one to three heteroatoms independently selected from nitrogen, sulfur and oxygen;

wherein said ring or rings formed by $R_{III-5}$ and $R_{III-6}$, or $R_{III-6}$ and $R_{III-7}$, and/or $R_{III-7}$ and $R_{III-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$ alkoxy, $(C_1-C_4)$alkylthio, amino, nitro, cyano, oxo, carboxy, $(C_1-C_6)$alkyloxycarbonyl, mono-N— or di-N,N—$(C_1-C_6)$ alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N— $(C_1-C_6)$alkylamino, said $(C_1-C_6)$alkyl substituent optionally having from one to nine fluorines;

provided that the $R_{III-5}$, $R_{III-6}$, $R_{III-7}$ and/or $R_{III-8}$, as the case may be, that do not form at least one ring are each independently hydrogen, halo, $(C_1-C_6)$alkoxy or $(C_1-C_6)$ alkyl, said $(C_1-C_6)$alkyl optionally having from one to nine fluorines.

Compounds of Formula III are disclosed in commonly assigned pending U.S. Pat. No. 6,147,089, the complete disclosure of which is herein incorporated by reference.

In a preferred embodiment, the CETP inhibitor is selected from one of the following compounds of Formula III:

[2R, 4S]4-[(3,5-bis-trifluoromethyl-benzyl)-methoxycarbonyl-amino]-2-methyl-2,3,4,6,7,8-hexahydro-cyclopenta [g]quinoline-1-carboxylic acid ethyl ester;

[6R, 8S]8-[(3,5-bis-trifluoromethyl-benzyl)-methoxycarbonyl-amino]-6-methyl-3,6,7,8-tetrahydro-1H-2-thia-5-azacyclopenta[b]naphthalene-5-carboxylic acid ethylester;

[6R, 8S]8-[(3,5-bis-trifluoromethyl-benzyl)-methoxycarbonyl-amino]-6-methyl-3,6,7,8-tetrahydro-2H-furo[2,3-g] quinoline-5-carboxylic acid ethyl ester;

[2R,4S]4-[(3,5-bis-trifluoromethyl-benzyl)-methoxycarbonyl-amino]-2-methyl-3,4,6,8-tetrahydro-2H-furo[3,4-g] quinoline-1-carboxylic acid ethyl ester;

[2R,4S]4-[(3,5-bis-trifluoromethyl-benzyl)-methoxycarbonyl-amino]-2-methyl-3,4,6,7,8,9-hexahydro-2H-benzo[g] quinoline-1-carboxylic acid propyl ester;

[7R,9S]9-[(3,5-bis-trifluoromethyl-benzyl)-methoxycarbonyl-amino]-7-methyl-1,2,3,7,8,9-hexahydro-6-aza-cyclopenta[a]naphthalene-6-carboxylic acid ethyl ester; and
[6S,8R]6-[(3,5-bis-trifluoromethyl-benzyl)-methoxycarbonyl-amino]-8-methyl-1,2,3,6,7,8-hexahydro-9-aza-cyclopenta[a]naphthalene-9-carboxylic acid ethyl ester.

Another class of CETP inhibitors that finds utility with the present invention consists of 4-carboxyamino-2-substituted-1,2,3,4,-tetrahydroquinolines, having the Formula IV

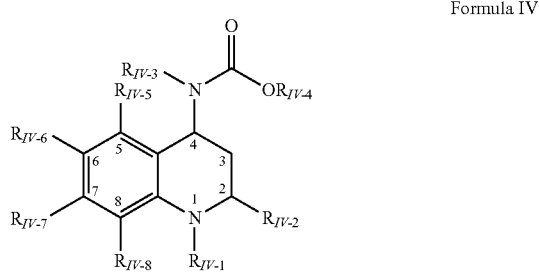

Formula IV and pharmaceutically acceptable forms thereof;

wherein $R_{IV-1}$ is hydrogen, $Y_{IV}$, $W_{IV}-X_{IV}$ or $W_{IV}-Y_{IV}$;

wherein $W_{IV}$ is a carbonyl, thiocarbonyl, sulfinyl or sulfonyl;

$X_{IV}$ is $-O-Y_{IV}$, $-S-Y_{IV}$, $-N(H)-Y_{IV}$ or $-N-(Y_{IV})_2$;

wherein $Y_{IV}$ for each occurrence is independently $Z_{IV}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{IV}$;

wherein $Z_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{IV}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{IV-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{IV-2}$ is a partially saturated, fully saturated or fully unsaturated three to seven membered ring optionally having one to two heteroatoms selected independently from oxygen, sulfur and nitrogen, wherein said $R_{IV-2}$ ring is optionally attached through $(C_1-C_4)$alkyl;

wherein said $R_{IV-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, oxo or $(C_1-C_6)$alkyloxycarbonyl;

with the proviso that $R_{IV-2}$ is not methyl;

$R_{IV-13}$ is hydrogen or $Q_{IV}$;

wherein $Q_{IV}$ is a fully saturated, partially unsaturated or fully unsaturated one to six membered straight or branched carbon chain wherein the carbons other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV}$;

wherein $V_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{IV}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$ alkenyl substituents are also optionally substituted with from one to nine fluorines;

$R_{IV-4}$ is $Q_{IV-1}$ or $V_{IV-1}$;

wherein $Q_{IV-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV-1}$;

wherein V$_{IV-1}$ is a partially saturated, fully saturated or fully unsaturated three to six membered ring optionally having one to two heteroatoms selected independently from oxygen, sulfur and nitrogen;

wherein said V$_{IV-1}$ substituent is optionally mono-, di-, tri-, or tetra-substituted independently with halo, (C$_1$-C$_6$)alkyl, (C$_1$-C$_6$)alkoxy, amino, nitro, cyano, (C$_1$-C$_6$)alkyloxycarbonyl, mono-N— or di-N,N—(C$_1$-C$_6$)alkylamino wherein said (C$_1$-C$_6$)alkyl substituent is optionally mono-substituted with oxo, said (C$_1$-C$_6$)alkyl substituent is also optionally substituted with from one to nine fluorines;

wherein either R$_{IV-3}$ must contain V$_{IV}$ or R$_{IV-4}$ must contain V$_{IV-1}$;

R$_{IV-5}$, R$_{IV-6}$, R$_{IV-7}$ and R$_{IV-8}$ are each independently hydrogen, a bond, nitro or halo wherein said bond is substituted with T$_{IV}$ or a partially saturated, fully saturated or fully unsaturated (C$_1$-C$_{12}$) straight or branched carbon chain wherein carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with T$_{IV}$;

wherein T$_{IV}$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said T$_{IV}$ substituent is optionally mono-, di- or tri-substituted independently with halo, (C$_1$-C$_6$)alkyl, (C$_2$-C$_6$)alkenyl, hydroxy, (C$_1$-C$_6$)alkoxy, (C$_1$-C$_4$)alkylthio, amino, nitro, cyano, oxo, carboxy, (C$_1$-C$_6$)alkyloxycarbonyl, mono-N— or di-N,N—(C$_1$-C$_6$)alkylamino wherein said (C$_1$-C$_6$)alkyl substituent is optionally mono-, di- or tri-substituted independently with hydroxy, (C$_1$-C$_6$)alkoxy, (C$_1$-C$_4$)alkylthio, amino, nitro, cyano, oxo, carboxy, (C$_1$-C$_6$)alkyloxycarbonyl, mono-N— or di-N,N—(C$_1$-C$_6$)alkylamino, said (C$_1$-C$_6$)alkyl substituent is also optionally substituted with from one to nine fluorines; and wherein R$_{IV-5}$ and R$_{IV-6}$, or R$_{IV-6}$ and R$_{IV-7}$, and/or R$_{IV-7}$ and R$_{IV-8}$ may also be taken together and can form at least one four to eight membered ring that is partially saturated or fully unsaturated optionally having one to three heteroatoms independently selected from nitrogen, sulfur and oxygen;

wherein said ring or rings formed by R$_{IV-5}$ and R$_{IV-6}$, or R$_{IV-6}$ and R$_{IV-7}$, and/or R$_{IV-7}$ and R$_{IV-8}$ are optionally mono-, di- or tri-substituted independently with halo, (C$_1$-C$_6$)alkyl, (C$_1$-C$_4$)alkylsulfonyl, (C$_2$-C$_6$)alkenyl, hydroxy, (C$_1$-C$_6$)alkoxy, (C$_1$-C$_4$)alkylthio, amino, nitro, cyano, oxo, carboxy, (C$_1$-C$_6$)alkyloxycarbonyl, mono-N— or di-N,N—(C$_1$-C$_6$) alkylamino wherein said (C$_1$-C$_6$)alkyl substituent is optionally mono-, di- or tri-substituted independently with hydroxy, (C$_1$-C$_6$)alkoxy, (C$_1$-C$_4$)alkylthio, amino, nitro, cyano, oxo, carboxy, (C$_1$-C$_6$)alkyloxycarbonyl, mono-N— or di-N,N— (C$_1$-C$_6$)alkylamino, said (C$_1$-C$_6$)alkyl substituent is also optionally substituted with from one to nine fluorines; with the proviso that when R$_{IV-2}$ is carboxyl or (C$_1$-C$_4$) alkylcarboxyl, then R$_{IV-1}$ is not hydrogen.

Compounds of Formula IV are disclosed in commonly assigned U.S. Pat. No. 6,197,786, the complete disclosure of which is herein incorporated by reference.

In a preferred embodiment, the CETP inhibitor is selected from one of the following compounds of Formula IV:

[2S,4S]4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S]2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2R,4R]4-[(3,5-bis-trifluoromethyl-benzyl)-methoxycarbonyl-amino]-2-cyclopropyl-6-trifluoromethyl-3,4-dihydro-2H-quinaline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester,

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester.

Another class of CETP inhibitors that finds utility with the present invention consists of 4-amino substituted-2-substituted-1,2,3,4,-tetrahydroquinolines, having the Formula V

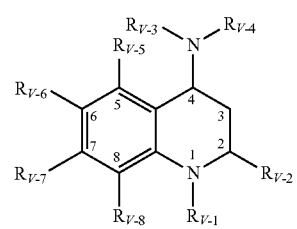

Formula V and pharmaceutically acceptable forms thereof;

wherein R$_{V-1}$, is Y$_V$, W$_V$—X$_V$ or W$_V$—Y$_V$;

wherein W$_V$ is a carbonyl, thiocarbonyl, sulfinyl or sulfonyl;

X$_V$ is —O—Y$_V$, —S—Y$_V$, —N(H)—Y$_V$ or —N—(Y$_V$)$_2$;

wherein Y$_V$ for each occurrence is independently Z$_V$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_V$;

wherein $Z_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_V$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{V-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{V-2}$ is a partially saturated, fully saturated or fully unsaturated three to seven membered ring optionally having one to two heteroatoms selected independently from oxygen, sulfur and nitrogen, wherein said $R_{V-2}$ ring is optionally attached through $(C_1-C_4)$alkyl;

wherein said $R_{V-2}$ ring is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, oxo or $(C_1-C_6)$alkyloxycarbonyl;

$R_{V-3}$ is hydrogen or $Q_V$;

wherein $Q_V$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_V$;

wherein $V_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$ alkenyl substituents are also optionally substituted with from one to nine fluorines;

$R_{V-4}$ is cyano, formyl, $W_{V-1}Q_{V-1}$, $W_{V-1}V_{V-1}$, $(C_1-C_4)$alkyleneV$_{V-1}$ or $V_{V-2}$;

wherein $W_{V-1}$ is carbonyl, thiocarbonyl, SO or $SO_2$, wherein $Q_{V-1}$ a fully saturated, partially unsaturated or fully unsaturated one to six membered straight or branched carbon chain wherein the carbons may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{V-1}$;

wherein $V_{V-1}$ is a partially saturated, fully saturated or fully unsaturated three to six membered ring optionally having one to two heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{V-1}$ substituent is optionally mono-, di-, tri-, or tetra-substituted independently with halo, $(C_1-C_6)$alkyl, $(C_1-C_6)$alkoxy, hydroxy, oxo, amino, nitro, cyano, $(C_1-C_6)$ alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein $V_{V-2}$ is a partially saturated, fully saturated or fully unsaturated five to seven membered ring containing one to four heteroatoms selected independently from oxygen, sulfur and nitrogen;

wherein said $V_{V-2}$ substituent is optionally mono-, di- or tri-substituted independently with halo, $(C_1-C_2)$alkyl, $(C_1-C_2)$alkoxy, hydroxy, or oxo wherein said $(C_1-C_2)$alkyl optionally has from one to five fluorines; and wherein $R_{V-4}$ does not include oxycarbonyl linked directly to the $C_4$ nitrogen;

wherein either $R_{V-3}$ must contain $V_V$ or $R_{V-4}$ must contain $V_{V-1}$;

$R_{V-5}$, $R_{V-6}$, $R_{V-7}$ and $R_{V-8}$ are independently hydrogen, a bond, nitro or halo wherein said bond is substituted with $T_V$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen, wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_V$;

wherein $T_V$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_V$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines;

wherein $R_{V-5}$ and $R_{V-6}$, or $R_{V-6}$ and $R_{V-7}$, and/or $R_{V-7}$ and $R_{V-8}$ may also be taken together and can form at least one ring that is a partially saturated or fully unsaturated four to eight membered ring optionally having one to three heteroatoms independently selected from nitrogen, sulfur and oxygen;

wherein said rings formed by $R_{V-5}$ and $R_{V-6}$, or $R_{V-6}$ and $R_{V-7}$, and/or $R_{V-7}$ and $R_{V-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines.

Compounds of Formula V are disclosed in commonly assigned U.S. Pat. No. 6,140,343, the complete disclosure of which is herein incorporated by reference.

In a preferred embodiment, the CETP inhibitor is selected from one of the following compounds of Formula V:

[2S,4S]4-[(3,5-bis-trifluoromethyl-benzyl)-formyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid tert-butyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-methyl-6-trifluoromethyl-3,4-dihydro-2H-quinoline-1-carboxylic acid ethyl ester;

[2S,4S]4-[1-(3,5-bis-trifluoromethyl-benzyl)-ureido]-2-cyclopropyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid ethyl ester;

[2S,4S]4-[acetyl-(3,5-bis-trifluoromethyl-benzyl)-amino]-2-methoxymethyl-6-trifluoromethyl-3,4-dihydro-2H-quinoline-1-carboxylic acid isopropyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-formyl-amino]-2-ethyl-6-trifluoromethyl-3,4-dihydro-2H-quinoline-1-carboxylic acid isopropyl ester;

[2R,4S]4-[(3,5-bis-trifluoromethyl-benzyl)-formyl-amino]-2-methyl-6-trifluoromethyl-3,4-dihydro-2H-quinoline-1-carboxylic acid ethyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid isopropyl ester;

[2R,4S]4-[(3,5-bis-trifluoromethyl-benzyl)-formyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-formyl-amino]-2-methyl-6-trifluoromethyl-3,4-dihydro-2H-quinoline-1-carboxylic acid isopropyl ester; and

[2R,4S]4-[acetyl-(3,5-bis-trifluoromethyl-benzyl)-amino]-2-methyl-6-trifluoromethyl-3,4-dihydro-2H-quinoline-1-carboxylic acid isopropyl ester.

Another class of CETP inhibitors that finds utility with the present invention consists of cycloalkano-pyridines having the Formula VI

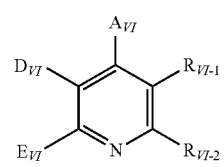

Formula VI and pharmaceutically acceptable forms thereof;

in which $A_{VI}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$NR_{VI-3}R_{VI-4}$, wherein $R_{VI-3}$ and $R_{VI-4}$ are identical or different and denote a hydrogen, phenyl or a straight-chain or branched alkyl containing up to 6 carbon atoms, $D_{VI}$ denotes an aryl containing 6 to 10 carbon atoms, which is optionally substituted with a phenyl, nitro, halogen, trifluoromethyl or trifluoromethoxy, or a radical according to the formula $R_{VI-5}$-$L_{VI}$—,

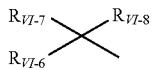

or $R_{VI-9}$-$T_{VI}$—$V_{VI}$—$X_{VI}$, wherein $R_{VI-5}$, $R_{VI-6}$ and $R_{VI-9}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5to 7-membered heterocycle containing up to 3 heteoatoms from the series of S, N and/or 0, and/or in the form of a group according to the formula —$OR_{VI-10}$, —$SR_{VI-11}$, —$SO_2R_{VI-12}$ or —$NR_{VI-13}R_{VI-14}$, wherein $R_{VI-10}$, $R_{VI-11}$ and $R_{VI-12}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{VI-13}$ and $R_{VI-14}$ are identical or different and have the meaning of $R_{VI-3}$ and $R_{VI-4}$ given above, or $R_{VI-5}$ and/or $R_{VI-6}$ denote a radical according to the formula

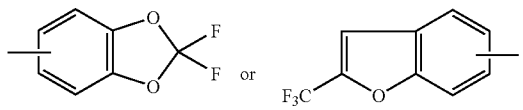

$R_{VI-7}$ denotes a hydrogen or halogen, and $R_{VI-8}$ denotes a hydrogen, halogen, azido, trifluoromethyl, hydroxyl, trifluoromethoxy, a straight-chain or branched alkoxy or alkyl containing up to 6 carbon atoms each, or a radical according to the formula

—$NR_{VI-15}R_{VI-16}$ wherein $R_{VI-15}$ and $R_{VI-16}$ are identical or different and have the meaning of $R_{VI-3}$ and $R_{VI-4}$ given above, or $R_{VI-7}$ and $R_{VI-8}$ together form a radical according to the formula =O or =$NR_{VI-17}$, wherein $R_{IV-17}$ denotes a hydrogen or a straight-chain or branched alkyl, alkoxy or acyl containing up to 6 carbon atoms each, $L_{VI}$ denotes a straight-chain or branched alkylene or alkenylene chain containing up to 8 carbon atoms each, which are optionally substituted with up to two hydroxyl groups, $T_{VI}$ and $X_{VI}$ are identical or different and denote a straight-chain or branched alkylene chain containing up to 8 carbon atoms, or $T_{VI}$ or $X_{VI}$ denotes a bond, $V_{VI}$ denotes an oxygen or sulfur atom or an —$NR_{VI-18}$ group, wherein $R_{VI-18}$ denotes a hydrogen or a straight-chain or branched alkyl containing up to 6 carbon atoms or a phenyl, $E_{VI}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl, $R_{VI-1}$ and $R_{VI-2}$ together form a straight-chain or branched alkylene chain containing up to 7 carbon atoms, which must be substituted with a carbonyl group and/or a radical according to the formula

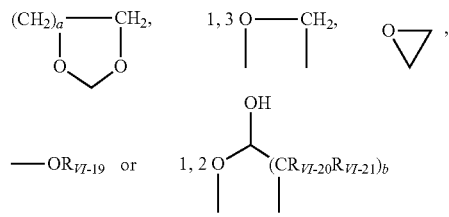

wherein a and b are identical or different and denote a number equaling 1, 2 or 3, $R_{VI-19}$ denotes a hydrogen atom, a cycloalkyl containing 3 to 7 carbon atoms, a straight-chain or branched silylalkyl containing up to 8 carbon atoms, or a straight-chain or branched alkyl containing up to 8 carbon atoms, which is optionally substituted with a hydroxyl, a straight-chain or a branched alkoxy containing up to 6 carbon atoms or a phenyl, which may in turn be substituted with a halogen, nitro, trifluoromethyl, trifluoromethoxy or phenyl or tetrazole-substituted phenyl, and an alkyl that is optionally substituted with a group according to the formula —$OR_{VI-22}$, wherein $R_{VI-22}$ denotes a straight-chain or branched acyl containing up to 4 carbon atoms or benzyl, or $R_{VI-19}$ denotes a straight-chain or branched acyl containing up to 20 carbon atoms or benzoyl, which is optionally substituted with a halogen, trifluoromethyl, nitro or trifluoromethoxy, or a straight-chain or branched fluoroacyl containing up to 8 carbon atoms, $R_{VI-20}$ and $R_{VI-21}$ are identical or different and denote a hydrogen, phenyl or a straight-chain or branched alkyl containing up to 6 carbon atoms, or $R_{VI-20}$ and $R_{VI-21}$ together form a 3- to 6-membered carbocyclic ring, and a the carbocyclic rings formed are optionally substituted, optionally also geminally, with up to six identical or different substituents in the form of trifluoromethyl, hydroxyl, nitrile, halogen, carboxyl, nitro, azido, cyano, cycloalkyl or cycloalkyloxy containing 3 to 7 carbon atoms each, a straight-chain or branched alkoxycarbonyl, alkoxy or alkylthio containing up to 6 carbon atoms each, or a straight-chain or branched alkyl containing up to 6 carbon atoms, which is in turn substituted with up to two identical or different substituents in the form of a hydroxyl, benzyloxy, trifluoromethyl, benzoyl, a straight-chain or branched alkoxy, oxyacyl or carboxyl containing up to 4 carbon atoms each and/or a phenyl, which may in turn be substituted with a halogen, trifluoromethyl or trifluoromethoxy, and/or the carbocyclic rings formed are optionally substituted, also geminally, with up to five identical or different substituents in the form of a phenyl, benzoyl, thiophenyl or sulfonylbenzyl, which in turn are optionally substituted with a halogen, trifluoromethyl, trifluoromethoxy or nitro, and/or optionally in the form of a radical according to the formula

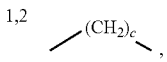

—SO$_2$—C$_6$H$_5$, —(CO)$_d$NR$_{VI-23}$R$_{VI-24}$ or =O, wherein
c is a number equaling 1, 2, 3 or 4,
d is a number equaling 0 or 1,
R$_{VI-23}$ and R$_{VI-24}$ are identical or different and denote a hydrogen, cycloalkyl containing 3 to 6 carbon atoms, a straight-chain or branched alkyl containing up to 6 carbon atoms, benzyl or phenyl, which is optionally substituted with up to two identical or different substituents in the form of halogen, trifluoromethyl, cyano, phenyl or nitro, and/or the carbocyclic rings formed are optionally substituted with a spiro-linked radical according to the formula

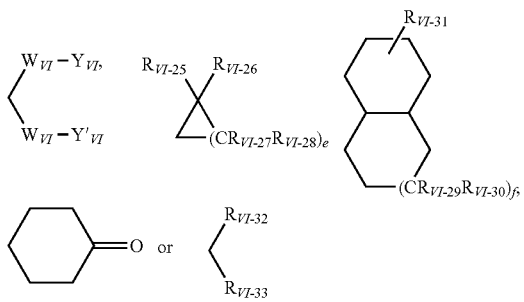

wherein
W$_{VI}$ denotes either an oxygen atom or a sulfur atom,
Y$_{VI}$ and Y'$_{VI}$ together form a 2- to 6-membered straight-chain or branched alkylene chain,
e is a number equaling 1, 2, 3, 4, 5, 6 or 7,
f is a number equaling 1 or 2,
R$_{VI-25}$, R$_{VI-26}$, R$_{VI-27}$, R$_{VI-28}$, R$_{VI-29}$, R$_{VI-30}$ and R$_{VI-31}$ are identical or different and denote a hydrogen, trifluoromethyl, phenyl, halogen or a straight-chain or branched alkyl or alkoxy containing up to 6 carbon atoms each, or
R$_{VI-25}$ and R$_{VI-26}$ or R$_{VI-27}$ and R$_{VI-28}$ each together denote a straight-chain or branched alkyl chain containing up to 6 carbon atoms or
R$_{VI-25}$ and R$_{VI-26}$ or R$_{VI-27}$ and R$_{VI-28}$ each together form a radical according to the formula

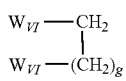

wherein
W$_{VI}$ has the meaning given above,
g is a number equaling 1, 2, 3, 4, 5, 6 or 7,
R$_{VI-32}$ and R$_{VI-33}$ together form a 3- to 7-membered heterocycle, which contains an oxygen or sulfur atom or a group according to the formula SO, SO$_2$ or —NR$_{VI-34}$, wherein
R$_{VI-34}$ denotes a hydrogen atom, a phenyl, benzyl, or a straight-chain or branched alkyl containing up to 4 carbon atoms, and salts and N oxides thereof, with the exception of 5(6H)-quinoiones, 3-benzoyl-7,8-dihydro-2,7,7-trimethyl-4-phenyl.

Compounds of Formula VI are disclosed in European Patent Application No. EP 818448 A1, the complete disclosure of which is herein incorporated by reference.

In a preferred embodiment, the CETP inhibitor is selected from one of the following compounds of Formula VI:

2-cyclopentyl-4-(4-fluorophenyl)-7,7-dimethyl-3-(4-trifluoromethylbenzoyl)-4,6,7,8-tetrahydro-1H-quinolin-5-one;

2-cyclopentyl-4-(4-fluorophenyl)-7,7-dimethyl-3-(4-trifluoromethylbenzoyl)-7,8-dihydro-6H-quinolin-5-one;

[2-cyclopentyl-4-(4-fluorophenyl)-5-hydroxy-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol;

5-(t-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline;

2-cyclopentyl-4-(4-fluorophenyl)-3-[fluoro-(4-trifluoromethylphenyl)-methyl]-7,7-dimethyl-5,6,7,8-tetrahydroquinolin-5-ol.

Another class of CETP inhibitors that finds utility with the present invention consists of substituted-pyridines having the Formula VII

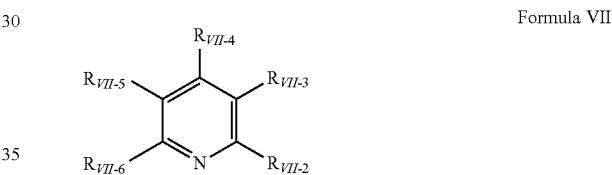

Formula VII and pharmaceutically acceptable forms thereof, wherein
R$_{VII-2}$ and R$_{VII-6}$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of R$_{VII-2}$ and R$_{VII-6}$ is fluorinated alkyl, chlorofluorinated alkyl or alkoxyalkyl;

R$_{VII-3}$ is selected from the group consisting of hydroxy, amido, arylcarbonyl, heteroarylcarbonyl, hydroxymethyl —CHO, —CO$_2$R$_{VII-7}$, wherein R$_{VII-7}$ is selected from the group consisting of hydrogen, alkyl and cyanoalkyl; and $$-\overset{R_{VII-15a}}{\underset{H}{C}}-R_{VII-16a}$$

wherein R$_{VII-15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and R$_{VII-16}$, is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

R$_{VII-4}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, hetereoarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclythioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, —CO(O)N($R_{VII-8a}R_{VII-8b}$), wherein $R_{VII-8a}$ and $R_{VII-8b}$ are independently selected from the group consisting of alkyl, alkenyl, alkynyl, aryl, heteroaryl and heterocyclyl, —SO$_2$R$_{VII-9}$, wherein R$_{VII-9}$ is selected from the group consisting of hydroxy, alkyl, alkenyl, alkynyl, aryl, heteroaryl and heterocyclyl, —OP(O)(OR$_{VII-10a}$) (OR$_{VII-10b}$), wherein R$_{VII-10a}$ and R$_{VII-10b}$ are independently selected from the group consisting of hydrogen, hydroxy, alkyl, alkenyl, alkynyl, aryl, heteroaryl and heterocyclyl, and —OP(S)(OR$_{VII-11}$a) (OR$_{VII-11b}$), wherein R$_{VII-11a}$ and R$_{VII-11b}$ are independently selected from the group consisting of alkyl, alkenyl, alkynyl, aryl, heteroaryl and heterocyclyl;

$R_{VII-5}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxyalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —CO$_2$R$_{VII-14}$, wherein R$_{VII-14}$ is selected from the group consisting of alkyl, alkenyl, alkynyl, aryl, heteroaryl and heterocyclyl;

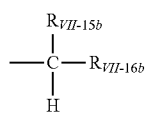

wherein $R_{VII-15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and $R_{VII-16b}$ is selected form the group consisting of alkyl, alkenyl, alkynyl, aryl, heteroaryl, heterocyclyl, arylalkoxy, and trialkylsilyloxy;

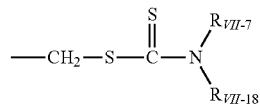

wherein $R_{VII-17}$ and $R_{VII-18}$ are independently selected from the group consisting of alkyl, cycloalkyl, alkenyl, alkynyl, aryl, heteroaryl and heterocyclyl;

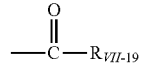

wherein $R_{VII-19}$ is selected from the group consisting of alkyl, cycloalkyl, alkenyl, alkynyl, aryl, heteroaryl, heterocyclyl, —SR$_{VII-20}$, —OR$_{VII-21}$, and —R$_{VII-22}$CO$_2$R$_{VII-23}$, wherein $R_{VII-20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, $R_{VII-21}$ is selected from the group consisting of alkyl, alkenyl, alkynyl, aryl, heteroaryl, and heterocyclyl, $R_{VII-22}$ is selected from the group consisting of alkylene or arylene, and $R_{VII-23}$ is selected from the group consisting of alkyl, alkenyl, alkynyl, aryl, heteroaryl, and heterocyclyl;

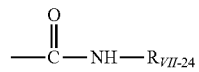

wherein $R_{VII-24}$ is selected from the group consisting of hydrogen, alkyl, cycloalkyl, alkenyl, alkynyl, aryl, heteroaryl, heterocyclyl, aralkyl, aralkenyl, and aralkynyl;

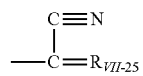

wherein $R_{VII-25}$ is heterocyclylidenyl;

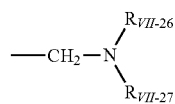

wherein $R_{VII-26}$ and $R_{VII-27}$ are independently selected from the group consisting of hydrogen, alkyl, cycloalkyl, alkenyl, alkynyl, aryl, heteroaryl, and heterocyclyl;

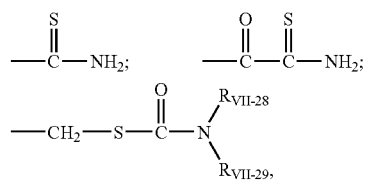

wherein $R_{VII\text{-}28}$ and $R_{VII\text{-}29}$ are independently selected from the group consisting of hydrogen, alkyl, cycloalkyl, alkenyl, alkynyl, aryl, heteroaryl, and heterocyclyl;

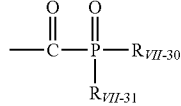

wherein $R_{VII\text{-}30}$ and $R_{VII\text{-}31}$ are independently alkoxy, alkenoxy, alkynoxy, aryloxy, heteroaryloxy, and heterocyclyloxy; and

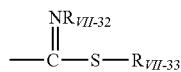

wherein $R_{VII\text{-}32}$ and $R_{VII\text{-}33}$ are independently selected from the group consisting of hydrogen, alkyl, cycloalkyl, alkenyl, alkynyl, aryl, heteroaryl, and heterocyclyl;

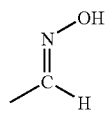

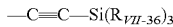

wherein $R_{VII\text{-}36}$ is selected from the group consisting of alkyl, alkenyl, aryl, heteroaryl and heterocyclyl;

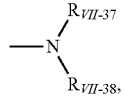

wherein $R_{VII\text{-}37}$ and $R_{VII\text{-}38}$ are independently selected from the group consisting of hydrogen, alkyl, cycloalkyl, alkenyl, alkynyl, aryl, heteroaryl, and heterocyclyl;

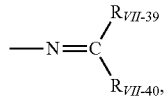

wherein $R_{VII\text{-}39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{VII\text{-}40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

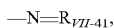

wherein $R_{VII\text{-}41}$ is heterocyclylidenyl;

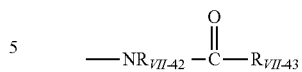

wherein $R_{VII\text{-}42}$ is selected from the group consisting of hydrogen, alkyl, alkenyl, alkynyl, aryl, heteroaryl, and heterocyclyl, and $R_{VII\text{-}43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

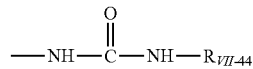

wherein $R_{VII\text{-}44}$ is selected from the group consisting of hydrogen, alkyl, cycloalkyl, alkenyl, alkynyl, aryl, heteroaryl and heterocyclyl;

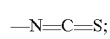

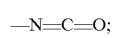

wherein $R_{VII\text{-}45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl,

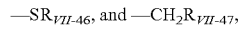

wherein $R_{VII\text{-}46}$ is selected from the group consisting of alkyl, alkenyl, alkynyl, aryl, heteroaryl and heterocyclyl, and $R_{VII\text{-}47}$ is selected from the group consisting of hydrogen, alkyl, alkenyl, alkynyl, aryl, heteroaryl and heterocyclyl; and

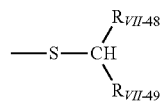

wherein $R_{VII\text{-}48}$ is selected from the group consisting of hydrogen, alkyl, cycloalkyl, alkenyl, alkynyl, aryl, heteroaryl and heterocyclyl, and $R_{VII\text{-}49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

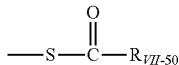

wherein $R_{VII-50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

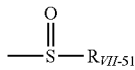

wherein $R_{VII-51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and

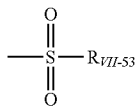

wherein $R_{VII-53}$ is selected from the group consisting of alkyl, alkenyl, alkynyl, aryl, heteroaryl and heterocyclyl;

provided that when $R_{VII-5}$ is selected from the group consisting of heterocyclylalkyl and heterocyclylalkenyl, the heterocyclyl radical of the corresponding heterocyclylalkyl or heterocyclylalkenyl is other than δ-lactone; and provided that when $R_{VII-4}$ is aryl, heteroaryl or heterocyclyl, and one of $R_{VII-2}$ and $R_{VII-6}$ is trifluoromethyl, then the other of $R_{VII-2}$ and $R_{VII-6}$ is difluoromethyl.

Compounds of Formula VII are disclosed in WO 9941237-A1, the complete disclosure of which is incorporated by reference.

In a preferred embodiment, the CETP inhibitor is selected from the following compounds of Formula VII:
dimethyl 5,5'-dithiobis[2-difluoromethyl-4-(2-methylpropyl)-6-(trifluoromethyl)-3-pyridine-carboxylate].

Another class of CETP inhibitors that finds utility with the present invention consists of substituted pyridines and biphenyls having the Formula VIII

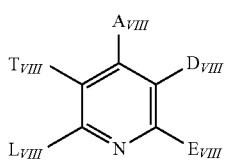

Formula VIII and pharmaceutically acceptable forms thereof, in which $A_{VIII}$ stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-1}R_{VIII-2}$, wherein $R_{VIII-1}$ and $R_{VIII-2}$ are identical or different and denote hydrogen, phenyl, or straight-chain or branched alkyl with up to 6 carbon atoms, $D_{VIII}$ stands for straight-chain or branched alkyl with up to 8 carbon atoms, which is substituted by hydroxy, $E_{VIII}$ and $L_{VIII}$ are either identical or different and stand for straight-chain or branched alkyl with up to 8 carbon atoms, which is optionally substituted by cycloalkyl with 3 to 8 carbon atoms, or stands for cycloalkyl with 3 to 8 carbon atoms, or $E_{VIII}$ has the above-mentioned meaning and $L_{VIII}$ in this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-3}R_{VIII-4}$, wherein $R_{VIII-3}$ and $R_{VIII-4}$ are identical or different and have the meaning given above for $R_{VIII-1}$ and $R_{VIII-2}$, or $E_{VIII}$ stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-5}R_{VIII-6}$, wherein $R_{VIII-5}$ and $R_{VIII-6}$ are identical or different and have the meaning given above for $R_{VIII-1}$ and $R_{VIII-2}$, and $L_{VIII}$ in this case stands for straight-chain or branched alkoxy with up to 8 carbon atoms or for cycloalkyloxy with 3 to 8 carbon atoms, $T_{VIII}$ stands for a radical of the formula

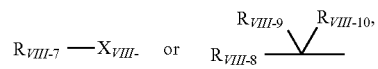

wherein $R_{VIII-7}$ and $R_{VIII-8}$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heteroatoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula —$NR_{VIII-11}R_{VIII-12}$, wherein $R_{VIII-11}$ and $R_{VIII-12}$ are identical or different and have the meaning given above for $R_{VIII-1}$ and $R_{VIII-2}$, $X_{VIII}$ denotes a straight or branched alkyl chain or alkenyl chain with 2 to 10 carbon atoms each, which are optionally substituted up to 2 times by hydroxy, $R_{VIII-9}$ denotes hydrogen, and $R_{VIII-10}$ denotes hydrogen, halogen, azido, trifluoromethyl, hydroxy, mercapto, trifluoromethoxy, straight-chain or branched alkoxy with up to 5 carbon atoms, or a radical of the formula —$NR_{VIII-13}R_{VIII-14}$, wherein $R_{VIII-13}$ and $R_{VIII-14}$ are identical or different and have the meaning given above for $R_{VIII-1}$ and $R_{VIII-2}$, or $R_{VIII-9}$ and $R_{VIII-10}$ form a carbonyl group together with the carbon atom.

Compounds of Formula VIII are disclosed in WO 9804528, the complete disclosure of which is incorporated by reference.

Another class of CETP inhibitors that finds utility with the present invention consists of substituted 1,2,4-triazoles having the Formula IX

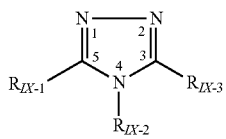

Formula IX and pharmaceutically acceptable forms thereof;

wherein $R_{IX-1}$ is selected from higher alkyl, higher alkenyl, higher alkynyl, aryl, aralkyl, aryloxyalkyl, alkoxyalkyl, alkylthioalkyl, arylthioalkyl, and cycloalkylalkyl;

wherein $R_{IX-2}$ is selected from aryl, heteroaryl, cycloalkyl, and cycloalkenyl, wherein $R_{IX-2}$ is optionally substituted at a substitutable position with one or more radicals independently selected from alkyl, haloalkyl, alkylthio, alkylsulfinyl, alkylsulfonyl, alkoxy, halo, aryloxy, aralkyloxy, aryl, aralkyl, aminosulfonyl, amino, monoalkylamino and dialkylamino; and wherein $R_{IX-3}$ is selected from hydrido, —SH and halo; provided $R_{IX-2}$ cannot be phenyl or 4-methylphenyl when $R_{IX-1}$ is higher alkyl and when $R_{IX-3}$ is —SH.

Compounds of Formula IX are disclosed in WO 9914204, the complete disclosure of which is incorporated by reference.

In a preferred embodiment, the CETP inhibitor is selected from the following compounds of Formula IX:

2,4-dihydro-4-(3-methoxyphenyl)-5-tridecyl-3H-1,2,4-triazole-3-thione;
2,4-dihydro-4-(2-fluorophenyl)-5-tridecyl-3H-1,2,4-triazole-3-thione;
2,4-dihydro-4-(2-methylphenyl)-5-tridecyl-3H-1,2,4-triazole-3-thione;
2,4-dihydro-4-(3-chlorophenyl)-5-tridecyl-3H-1,2,4-triazole-3-thione;
2,4-dihydro-4-(2-methoxyphenyl)-5-tridecyl-3H-1,2,4-triazole-3-thione;
2,4-dihydro-4-(3-methylphenyl)-5-tridecyl-3H-1,2,4-triazole-3-thione;
4-cyclohexyl-2,4-dihydro-5-tridecyl-3H-1,2,4-triazole-3-thione;
2,4-dihydro-4-(3-pyridyl)-5-tridecyl-3H-1,2,4-triazole-3-thione;
2,4-dihydro-4-(2-ethoxyphenyl)-5-tridecyl-3H-1,2,4-triazole-3-thione;
2,4-dihydro-4-(2,6-dimethylphenyl)-5-tridecyl-3H-1,2,4-triazole-3-thione;
2,4-dihydro-4-(4-phenoxyphenyl)-5-tridecyl-3H-1,2,4-triazole-3-thione;
4-(1,3-benzodioxol-5-yl)-2,4-dihydro-5-tridecyl-3H-1,2,4-triazole-3-thione;
4-(2-chlorophenyl)-2,4-dihydro-5-tridecyl-3H-1,2,4-triazole-3-thione;
2,4-dihydro-4-(4-methoxyphenyl)-5-tridecyl-3H-1,2,4-triazole-3-thione;
2,4-dihydro-5-tridecyl-4-(3-trifluoromethylphenyl)-3H-1,2,4-triazole-3-thione;
2,4-dihydro-5-tridecyl-4-(3-fluorophenyl)-3H-1,2,4-triazole-3-thione;
4-(3-chloro-4-methylphenyl)-2,4-dihydro-5-tridecyl-3H-1,2,4-triazole-3-thione;
2,4-dihydro-4-(2-methylthiophenyl)-5-tridecyl-3H-1,2,4-triazole-3-thione;
4-(4-benzyloxyphenyl)-2,4-dihydro-5-tridecyl-3H-1,2,4-triazole-3-thione;
2,4-dihydro-4-(2-naphthyl)-5-tridecyl-3H-1,2,4-triazole-3-thione;
2,4-dihydro-5-tridecyl-4-(4-trifluoromethylphenyl)-3H-1,2,4-triazole-3-thione;
2,4-dihydro-4-(1-naphthyl)-5-tridecyl-3H-1,2,4-triazole-3-thione;
2,4-dihydro-4-(3-methylthiophenyl)-5-tridecyl-3H-1,2,4-triazole-3-thione;
2,4-dihydro-4-(4-methylthiophenyl)-5-tridecyl-3H-1,2,4-triazole-3-thione;
2,4-dihydro-4-(3,4-dimethoxyphenyl)-5-tridecyl-3H-1,2,4-triazole-3-thione;
2,4-dihydro-4-(2,5-dimethoxyphenyl)-5-tridecyl-3H-1,2,4-triazole-3-thione;
2,4-dihydro-4-(2-methoxy-5-chlorophenyl)-5-tridecyl-3H-1,2,4-triazole-3-thione;
4-(4-aminosulfonylphenyl)-2,4-dihydro-5-tridecyl-3H-1,2,4-triazole-3-thione;
2,4-dihydro-5-dodecyl-4-(3-methoxyphenyl)-3H-1,2,4-triazole-3-thione;
2,4-dihydro-4-(3-methoxyphenyl)-5-tetradecyl-3H-1,2,4-triazole-3-thione;
2,4-dihydro-4-(3-methoxyphenyl)-5-undecyl-3H-1,2,4-triazole-3-thione; and
2,4-dihydro-(4-methoxyphenyl)-5-pentadecyl-3H-1,2,4-triazole-3-thione.

Another class of CETP inhibitors that finds utility with the present invention consists of hetero-tetrahydroquinolines having the Formula X

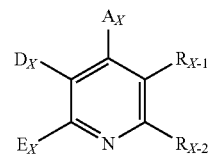

Formula X

N-oxides of said compounds, and pharmaceutically acceptable forms thereof; in which $A_X$ represents cycloalkyl with 3 to 8 carbon atoms or a 5- to 7-membered, saturated, partially saturated or unsaturated, optionally benzo-condensed heterocyclic ring containing up to 3 heteroatoms from the series comprising S, N and/or O, that in case of a saturated heterocyclic ring is bonded to a nitrogen function, optionally bridged over it, and in which the aromatic systems mentioned above are optionally substituted up to 5-times in an identical or different substituents in the form of halogen, nitro, hydroxy, trifluoromethyl, trifluoromethoxy or by a straight-chain or branched alkyl, acyl, hydroxyalkyl or alkoxy each having up to 7 carbon atoms or by a group of the formula —$NR_{X-3}R_{X-4}$, in which $R_{X-3}$ and $R_{X-4}$ are identical or different and denote hydrogen, phenyl or straight-chain or branched alkyl having up to 6 carbon atoms, or $A_X$ represents a radical of the formula

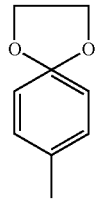

$D_X$ represents an aryl having 6 to 10 carbon atoms, that is optionally substituted by phenyl, nitro, halogen, trifluormethyl or trifluormethoxy, or it represents a radical of the formula

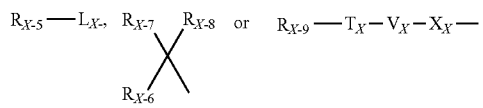

in which $R_{X-5}$, $R_{X-6}$ and $R_{X-9}$ independently of one another denote cycloalkyl having 3 to 6 carbon atoms, or an aryl having 6 to 10 carbon atoms or a 5- to 7-membered aromatic, optionally benzo-condensed saturated or unsaturated, mono-, bi-, or tricyclic heterocyclic ring from the series consisting of S, N and/or O, in which the rings are substituted, optionally, in case of the nitrogen containing aromatic rings via the N function, with up to 5 identical or different substituents in the form of halogen, trifluoromethyl, nitro, hydroxy, cyano, carbonyl, trifluoromethoxy, straight straight-chain or branched acyl, alkyl, alkylthio, alkylalkoxy, alkoxy, or alkoxycarbonyl each having up to 6 carbon atoms, by aryl or trifluoromethyl-substituted aryl each having 6 to 10 carbon atoms or by an, optionally benzo-condensed, aromatic 5- to 7-membered heterocyclic ring having up to 3 heteroatoms from the series consisting of S, N, and/or 0, and/or substituted by a group of the formula —$OR_{X-10}$, —$SR_{X-11}$, $SO_2R_{X-12}$ or —$NR_{X-13}R_{X-14}$, in which $R_{X-10}$, $R_{X-11}$ and $R_{X-12}$ independently from each other denote aryl having 6 to 10 carbon atoms, which is in turn substituted with up to 2 identical or different substituents in the form of phenyl, halogen or a straight-chain or branched alkyl having up to 6 carbon atoms, $R_{X-13}$ and $R_{X-14}$ are identical or different and have the meaning of $R_{X-3}$ and $R_{X-4}$ indicated above, or $R_{X-5}$ and/or $R_{X-6}$ denote a radical of the formula

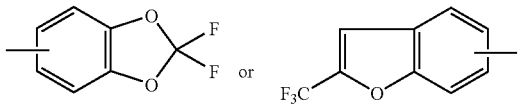

$R_{X-7}$ denotes hydrogen or halogen, and $R_{X-8}$ denotes hydrogen, halogen, azido, trifluoromethyl, hydroxy, trifluoromethoxy, straight-chain or branched alkoxy or alkyl having up to 6 carbon atoms or a radical of the formula —$NR_{X-15}R_{X-16}$, in which $R_{X-15}$ and $R_{X-16}$ are identical or different and have the meaning of $R_{X-3}$ and $R_{X-4}$ indicated above, or $R_{X-7}$ and $R_{X-8}$ together form a radical of the formula =O or =$NR_{X-17}$, in which $R_{X-17}$ denotes hydrogen or straight chain or branched alkyl, alkoxy or acyl having up to 6 carbon atoms, $L_X$ denotes a straight chain or branched alkylene or alkenylene chain having up to 8 carbon atoms, that are optionally substituted with up to 2 hydroxy groups, $T_x$ and $X_x$ are identical or different and denote a straight chain or branched alkylene chain with up to 8 carbon atoms or $T_x$ or $X_x$ denotes a bond, $V_x$ represents an oxygen or sulfur atom or an —$NR_{X-18}$- group, in which $R_{X-18}$ denotes hydrogen or straight chain or branched alkyl with up to 6 carbon atoms or phenyl, $E_x$ represents cycloalkyl with 3 to 8 carbon atoms, or straight chain or branched alkyl with up to 8 carbon atoms, that is optionally substituted by cycloalkyl with 3 to 8 carbon atoms or hydroxy, or represents a phenyl, that is optionally substituted by halogen or trifluoromethyl, $R_{X-1}$ and $R_{X-2}$ together form a straight-chain or branched alkylene chain with up to 7 carbon atoms, that must be substituted by carbonyl group and/or by a radical with the formula

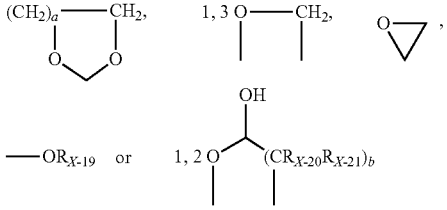

in which a and b are identical or different and denote a number equaling 1,2, or 3, $R_{X-19}$ denotes hydrogen, cycloalkyl with 3 up to 7 carbon atoms, straight chain or branched silylalkyl with up to 8 carbon atoms or straight chain or branched alkyl with up to 8 carbon atoms, that are optionally substituted by hydroxyl, straight chain or branched alkoxy with up to 6 carbon atoms or by phenyl, which in turn might be substituted by halogen, nitro, trifluormethyl, trifluoromethoxy or by phenyl or by tetrazole-substituted phenyl, and alkyl, optionally be substituted by a group with the formula —$OR_{X-22}$, in which R$_{X-22}$ denotes a straight chain or branched acyl with up to 4 carbon atoms or benzyl, or R$_{X-19}$ denotes straight chain or branched acyl with up to 20 carbon atoms or benzoyl, that is optionally substituted by halogen, trifluoromethyl, nitro or trifluoromethoxy, or it denotes straight chain or branched fluoroacyl with up to 8 carbon atoms and 9 fluorine atoms, R$_{X-20}$ and R$_{X-21}$ are identical or different and denote hydrogen, phenyl or straight chain or branched alkyl with up to 6 carbon atoms, or R$_{X-20}$ and R$_{X-21}$ together form a 3- to 6-membered carbocyclic ring, and the carbocyclic rings formed are optionally substituted, optionally also geminally, with up to six identical or different substituents in the form of triflouromethyl, hydroxy, nitrile, halogen, carboxyl, nitro, azido, cyano, cycloalkyl or cycloalkyloxy with 3 to 7 carbon atoms each, by straight chain or branched alkoxycarbonyl, alkoxy or alkylthio with up to 6 carbon atoms each or by straight chain or branched alkyl with up to 6 carbon atoms, which in turn is substituted with up to 2 identically or differently by hydroxyl, benzyloxy, trifluoromethyl, benzoyl, straight chain or branched alkoxy, oxyacyl or carbonyl with up to 4 carbon atoms each and/or phenyl, which may in turn be substituted with a halogen, trifuoromethyl or trifluoromethoxy, and/or the formed carbocyclic rings are optionally substituted, also geminally, with up to 5 identical or different substituents in the form of phenyl, benzoyl, thiophenyl or sulfonylbenzyl, which in turn are optionally substituted by halogen, trifluoromethyl, trifluoromethoxy or nitro, and/or optionally are substituted by a radical with the formula

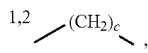

$-SO_2-C_6H_5$, $-(CO)_d NR_{X-23} R_{X-24}$ or $=O$, in which c denotes a number equaling 1, 2, 3, or 4, d denotes a number equaling 0 or 1, R$_{X-23}$ and R$_{X-24}$ are identical or different and denote hydrogen, cycloalkyl with 3 to 6 carbon atoms, straight chain or branched alkyl with up to 6 carbon atoms, benzyl or phenyl, that is optionally substituted with up to 2 identically or differently by halogen, trifluoromethyl, cyano, phenyl or nitro, and/or the formed carbocyclic rings are substituted optionally by a spiro-linked radical with the formula

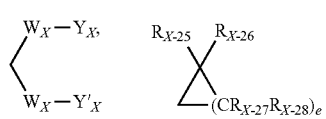
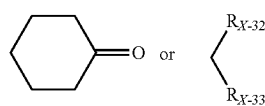

in which

W$_x$ denotes either an oxygen or a sulfur atom

Y$_x$ and Y'$_x$ together form a 2 to 6 membered straight chain or branched alkylene chain, e denotes a number equaling 1, 2, 3, 4, 5, 6, or 7, f denotes a number equaling 1 or 2, R$_{X-25}$, R$_{X-26}$, R$_{X-27}$, R$_{X-28}$, R$_{X-29}$, R$_{X-30}$ and R$_{X-31}$ are identical or different and denote hydrogen, trifluoromethyl, phenyl, halogen or straight chain or branched alkyl or alkoxy with up to 6 carbon atoms each, or R$_{X-25}$ and R$_{X-26}$ or R$_{X-27}$ and R$_{X-28}$ respectively form together a straight chain or branched alkyl chain with up to 6 carbon atoms, or R$_{X-25}$ and R$_{X-26}$ or R$_{X-27}$ and R$_{X-28}$ each together form a radical with the formula

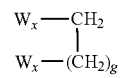

in which

W$_X$ has the meaning given above, g denotes a number equaling 1, 2, 3, 4, 5, 6, or 7, R$_{X-32}$ and R$_{X-33}$ form together a 3- to 7-membered heterocycle, which contains an oxygen or sulfur atom or a group with the formula SO, SO$_2$ or $\pi$-NR$_{X-34}$, in which R$_{X-34}$ denotes hydrogen, phenyl, benzyl or straight or branched alkyl with up to 4 carbon atoms.

Compounds of Formula X are disclosed in WO 9914215, the complete disclosure of which is incorporated by reference.

In a preferred embodiment, the CETP inhibitor is selected from the following compounds of Formula X:

2-cyclopentyl-5-hydroxy-7,7-dimethyl-4-(3-thienyl)-3-(4-trifluoromethylbenxoyl)-5,6,7,8-tetrahydroquinoline;

2-cyclopentyl-3-[fluoro-(4-trifluoromethylphenyl)methyl]-5-hydroxy-7,7-dimethyl-4-(3-thienyl)-5,6,7,8-tetrahydroquinoline; and 2-cyclopentyl-5-hydroxy-7,7-dimethyl-4-(3-thienyl)-3-(trifluoromethylbenxyl)-5,6,7,8-tetrahydroquinoline.

Another class of CETP inhibitors that finds utility with the present invention consists of substituted tetrahydro naphthalines and analogous compounds having the Formula XI

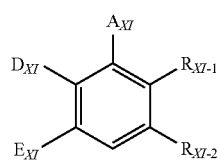

and pharmaceutically acceptable forms thereof, in which

A$_{XI}$ stands for cycloalkyl with 3 to 8 carbon atoms, or stands for aryl with 6 to 10 carbon atoms, or stands for a 5- to 7-membered, saturated, partially unsaturated or unsaturated, possibly benzocondensated, heterocycle with up to 4 heteroatoms from the series S, N and/or O, where aryl and/or the heterocyclic ring systems mentioned above are substituted up to 5-fold, identical or different, by cyano, halogen, nitro, carboxyl, hydroxy, trifluoromethyl, trifluoro-methoxy, or by straight-chain or branched alkyl, acyl, hydroxyalkyl, alkylthio, alkoxycarbonyl, oxyalkoxycarbonyl or alkoxy each with up to 7 carbon atoms, or by a group of the formula $$-NR_{XI-3}R_{XI-4},$$

in which $R_{XI-3}$ and $R_{XI-4}$ are identical or different and denote hydrogen, phenyl, or straight-chain or branched alkyl with up to 6 carbon atoms $D_{XI}$ stands for a radical of the formula $$R_{XI-5}-L_{XI}-, \quad \underset{R_{XI-6}}{\overset{R_{XI-7}}{\times}}\overset{R_{XI-8}}{, \text{ or }} R_{XI-9}-T_{XI}-V_{XI}-X_{XI}-$$

in which $R_{XI-5}$, $R_{XI-6}$ and $R_{XI-9}$, independent of each other, denote cycloalkyl with 3 to 6 carbon atoms, or denote aryl with 6 to 10 carbon atoms, or denote a 5- to 7-membered, possibly benzocondensated, saturated or unsaturated, mono-, bi- or tricyclic heterocycle with up to 4 heteroatoms of the series S, N and/or O, where the cycles are possibly substituted-in the case of the nitrogen-containing rings also via the N-function-up to 5-fold, identical or different, by halogen, trifluoromethyl, nitro, hydroxy, cyano, carboxyl, trifluoromethoxy, straight-chain or branched acyl, alkyl, alkylthio, alkylalkoxy, alkoxy or alkoxycarbonyl with up to 6 carbon atoms each by aryl or trifluoromethyl substituted aryl with 6 to 10 carbon atoms each, or by a possibly benzocondensated aromatic 5- to 7-membered heterocycle with up to 3 heteroatoms of the series S, N and/or O, and/or are substituted by a group of the formula $$-OR_{XI-10}, -SR_{XI-11}, -SO_2R_{XI-12} \text{ or } -NR_{XI-13}R_{XI-14},$$

in which $R_{XI-10}$, $R_{XI-11}$ and $R_{XI-12}$, independent of each other, denote aryl with 6 to 10 carbon atoms, which itself is substituted up to 2-fold, identical or different, by phenyl, halogen or by straight-chain or branched alkyl with up to 6 carbon atoms, $R_{XI-13}$ and $R_{XI-14}$ are identical or different and have the meaning given above for $R_{XI-3}$ and $R_{XI-4}$, or $R_{XI-5}$ and/or $R_{XI-6}$ denote a radical of the formula <chemical structures>

$R_{XI-7}$ denotes hydrogen, halogen or methyl, and $R_{XI-8}$ denotes hydrogen, halogen, azido, trifluoromethyl, hydroxy, trifluoromethoxy, straight-chain or branched alkoxy or alkyl with up to 6 carbon atoms each, or a radical of the formula $-NR_{XI-15}R_{XI-16}$, in which $R_{XI-15}$ and $R_{XI-16}$ are identical or different and have the meaning given above for $R_{XI-3}$ and $R_{XI-4}$, or $R_{XI-7}$ and $R_{XI-6}$ together form a radical of the formula $=O$ or $=NR_{XI-17}$, in which $R_{XI-17}$ denotes hydrogen or straight-chain or branched alkyl, alkoxy or acyl with up to 6 carbon atoms each, $L_{XI}$ denotes a straight-chain or branched alkylene- or alkenylene chain with up to 8 carbon atoms each, which is possibly substituted up to 2-fold by hydroxy, $T_{XI}$ and $X_{XI}$ are identical or different and denote a straight-chain or branched alkylene chain with up to 8 carbon atoms, or $T_{XI}$ and $X_{XI}$ denotes a bond, $V_{XI}$ stands for an oxygen- or sulfur atom or for an $-NR_{XI-18}$ group, in which $R_{XI-18}$ denotes hydrogen or straight-chain or branched alkyl with up to 6 carbon atoms, or phenyl, $E_{XI}$ stands for cycloalkyl with 3 to 8 carbon atoms, or stands for straight-chain or branched alkyl with up to 8 carbon atoms, which is possibly substituted by cycloalkyl with 3 to 8 carbon atoms or hydroxy, or stands for phenyl, which is possibly substituted by halogen or trifluoromethyl, $R_{XI-1}$ and $R_{XI-2}$ together form a straight-chain or branched alkylene chain with up to 7 carbon atoms, which must be substituted by a carbonyl group and/or by a radical of the formula $$(CH_2)_a\overset{\displaystyle CH_2}{\underset{\displaystyle O}{|}}, \quad 1,3 \; O\overset{\displaystyle CH_2}{\underset{\displaystyle |}{|}}, \quad O\overset{\triangledown}{,}$$

$$-OR_{XI-19} \quad \text{or} \quad 1,2 \; O\overset{OH}{\underset{\displaystyle |}{\overset{\displaystyle |}{}}}(CR_{XI-20}R_{XI-21})_b$$

in which a and b are identical or different and denote a number 1, 2 or 3

$R_{XI-19}$ denotes hydrogen, cycloalkyl with 3 to 7 carbon atoms, straight-chain or branched silylalkyl with up to 8 carbon atoms, or straight-chain or branched alkyl with up to 8 carbon atoms, which is possibly substituted by hydroxy, straight-chain or branched alkoxy with up to 6 carbon atoms, or by phenyl, which itself can be substituted by halogen, nitro, trifluoromethyl, trifluoromethoxy or by phenyl substituted by phenyl or tetrazol, and alkyl is possibly substituted by a group of the formula $-OR_{XI-22}$, in which $R_{XI-22}$ denotes straight-chain or branched acyl with up to 4 carbon atoms, or benzyl, or $R_{XI-19}$ denotes straight-chain or branched acyl with up to 20 carbon atoms or benzoyl, which is possibly substituted by halogen, trifluoromethyl, nitro or trifluoromethoxy, or denotes straight-chain or branched fluoroacyl with up to 8 carbon atoms and 9 fluorine atoms, $R_{XI-20}$ and $R_{XI-21}$ are identical or different, denoting hydrogen, phenyl or straight-chain or branched alkyl with up to 6 carbon atoms, or $R_{XI-20}$ and $R_{XI-21}$ together form a 3- to 6-membered carbocycle, and, possibly also geminally, the alkylene chain formed by $R_{XI-1}$ and $R_{XI-2}$, is possibly substituted up to 6-fold, identical or different, by trifluoromethyl, hydroxy, nitrile, halogen, carboxyl, nitro, azido, cyano, cycloalkyl or cycloalkyloxy with 3 to 7 carbon atoms each, by straight-chain or branched alkoxycarbonyl, alkoxy or alkoxythio with up to 6 carbon atoms each, or by straight-chain or branched alkyl with up to 6 carbon atoms, which itself is substituted up to 2-fold, identical or different, by hydroxyl, benzyloxy, trifluoromethyl, benzoyl, straight-chain or branched alkoxy, oxyacyl or carboxyl with up to 4 carbon atoms each, and/or phenyl—which itself can be substituted by halogen, trifluoromethyl or trifluoromethoxy, and/or the alkylene chain formed by $R_{XI-1}$ and $R_{XI-2}$ is substituted, also geminally, possibly up to 5-fold, identical or different, by phenyl, benzoyl, thiophenyl or sulfobenzyl—which themselves are possibly substituted by halogen, trifluoromethyl, trifluoromethoxy or nitro, and/or the alkylene chain formed by $R_{XI-1}$ and $R_{XI-2}$ is possibly substituted by a radical of the formula

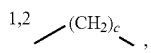

$-SO_2-C_6H_5, -(CO)_dNR_{XI-23}R_{XI-24}$ or $=O$, in which c denotes a number 1, 2, 3 or 4, d denotes a number 0 or 1, $R_{XI-23}$ and $R_{XI-24}$ are identical or different and denote hydrogen, cycloalkyl with 3 to 6 carbon atoms, straight-chain or branched alkyl with up to 6 carbon atoms, benzyl or phenyl, which is possibly substituted up to 2-fold identical or different, by halogen, trifluoromethyl, cyano, phenyl or nitro, and/or the alkylene chain formed by $R_{XI-1}$ and $R_{XI-2}$ is possibly substituted by a spiro-jointed radical of the formula

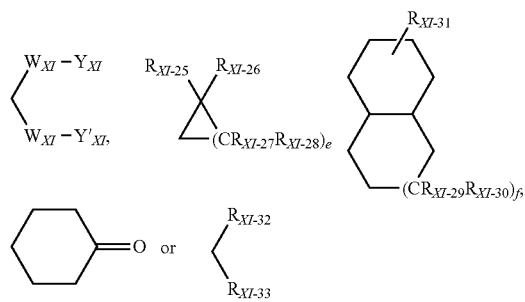

in which $W_{XI}$ denotes either an oxygen or a sulfur atom, $Y_{XI}$ and $Y'_{XI}$ together form a 2- to 6-membered straight-chain or branched alkylene chain, e is a number 1, 2, 3, 4, 5, 6 or 7, f denotes a number 1 or 2, $R_{XI-25}, R_{XI-26}, R_{XI-27}, R_{XI-28}, R_{XI-29}, R_{XI-30}$ and $R_{XI-31}$ are identical or different and denote hydrogen, trifluoromethyl, phenyl, halogen, or straight-chain or branched alkyl or alkoxy with up to 6 carbon atoms each, or $R_{XI-25}$ and $R_{XI-26}$ or $R_{XI-27}$ and $R_{XI-28}$ together form a straight-chain or branched alkyl chain with up to 6 carbon atoms, or $R_{XI-25}$ and $R_{XI-26}$ or $R_{XI-27}$ and $R_{XI-28}$ together form a radical of the formula

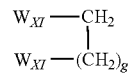

in which $W_{XI}$ has the meaning given above, g is a number 1, 2, 3, 4, 5, 6 or 7, $R_{XI-32}$ and $R_{XI-33}$ together form a 3- to 7-membered heterocycle that contains an oxygen- or sulfur atom or a group of the formula SO, $SO_2$ or $-NR_{XI-34}$, in which $R_{XI-34}$ denotes hydrogen, phenyl, benzyl, or straight-chain or branched alkyl with up to 4 carbon atoms.

Compounds of Formula XI are disclosed in WO 9914174, the complete disclosure of which is incorporated by reference.

Another class of CETP inhibitors that finds utility with the present invention consists of 2-aryl-substituted pyridines having the Formula XII

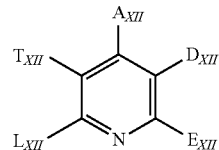

Formula XII and pharmaceutically acceptable forms thereof, in which $A_{XII}$ and $E_{XII}$ are identical or different and stand for aryl with 6 to 10 carbon atoms which is possibly substituted, up to 5-fold identical or different, by halogen, hydroxy, trifluoromethyl, trifluoromethoxy, nitro or by straight-chain or branched alkyl, acyl, hydroxy alkyl or alkoxy with up to 7 carbon atoms each, or by a group of the formula $-NR_{XII-1}R_{XII-2}$, where $R_{XII-1}$ and $R_{XII-2}$ are identical or different and are meant to be hydrogen, phenyl or straight-chain or branched alkyl with up to 6 carbon atoms, $D_{XII}$ stands for straight-chain or branched alkyl with up to 8 carbon atoms, which is substituted by hydroxy, $L_{XII}$ stands for cycloalkyl with 3 to 8 carbon atoms or for straight-chain or branched alkyl with up to 8 carbon atoms, which is possibly substituted by cycloalkyl with 3 to 8 carbon atoms, or by hydroxy, $T_{XII}$ stands for a radical of the formula $R_{XII-3}-X_{XII}-$ or

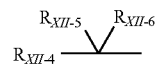

where $R_{XII-3}$ and $R_{XII-4}$ are identical or different and are meant to be cycloalkyl with 3 to 8 carbon atoms, or aryl with 6 to 10 carbon atoms, or a 5- to 7-membered aromatic, possibly benzocondensated heterocycle with up to 3 heteroatoms from the series S, N and/or O, which are possibly substituted up to 3-fold identical or different, by trifluoromethyl, trifluoromethoxy, halogen, hydroxy, carboxyl, nitro, by straight-chain or branched alkyl, acyl, alkoxy or alkoxycarbonyl with up to 6 carbon atoms each or by phenyl, phenoxy or phenylthio which in turn can be substituted by halogen trifluoromethyl or trifluoromethoxy, and/or where the cycles are possibly substituted by a group of the formula —$NR_{XII-7}R_{XII-8}$, where $R_{XII-7}$ and $R_{XII-8}$ are identical or different and have the meaning of $R_{XII-1}$ and $R_{XII-2}$ given above, $X_{XII}$ is a straight-chain or branched alkyl or alkenyl with 2 to 10 carbon atoms each, possibly substituted up to 2-fold by hydroxy or halogen, $R_{XII-5}$ stands for hydrogen, and $R_{XII-6}$ means to be hydrogen, halogen, mercapto, azido, trifluoromethyl, hydroxy, trifluoromethoxy, straight-chain or branched alkoxy with up to 5 carbon atoms, or a radical of the formula —$NR_{XII-9}R_{XII-10}$, where $R_{XII-9}$ and $R_{XII-10}$ are identical or different and have the meaning of $R_{XII-1}$ and $R_{XII-2}$ given above, or $R_{XII-5}$ and $R_{XII-6}$, together with the carbon atom, form a carbonyl group.

Compounds of Formula XII are disclosed in EP 796846-A1, the complete disclosure of which is incorporated by reference.

In a preferred embodiment, the CETP inhibitor is selected from the following compounds of Formula XII:

4,6-bis-(p-fluorophenyl)-2-isopropyl-3-[(p-trifluoromethylphenyl)-(fluoro)-methyl]-5-(1-hydroxyethyl)pyridine;
2,4-bis-(4-fluorophenyl)-6-isopropyl-5-[4-(trifluoromethylphenyl)-fluoromethyl]-3-hydroxymethyl)pyridine; and
2,4-bis-(4-fluorophenyl)-6-isopropyl-5-[2-(3-trifluoromethylphenyl)vinyl]-3-hydroxymethyl)pyridine.

Another class of CETP inhibitors that finds utility with the present invention consists of compounds having the Formula XIII

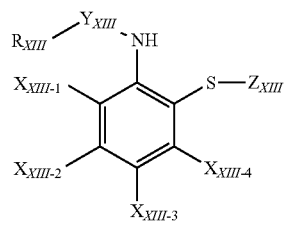

Formula XIII and pharmaceutically acceptable forms thereof, in which $R_{XII}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted, $X_{XIII-1}$, $X_{XIII-2}$, $X_{XIII-3}$, $X_{XIII-4}$ may be the same or different and are a hydrogen atom; halogen atom; $C_{1-4}$ lower alkyl; halogenated $C_{1-4}$ lower alkyl; $C_{1-4}$ lower alkoxy; cyano group; nitro group; acyl; or aryl, respectively;

$Y_{XIII}$ is —CO—; or —$SO_2$—; and $Z_{XIII}$ is a hydrogen atom; or mercapto protective group.

Compounds of Formula XII are disclosed in WO 98/35937, the complete disclosure of which is incorporated by reference.

In a preferred embodiment, the CETP inhibitor is selected from the following compounds of Formula XIII:

N,N'-(dithiodi-2,1-phenylene)bis[2,2-dimethyl-propanamide];
N,N'-(dithiodi-2,1-phenylene)bis[1-methyl-cyclohexanecarboxamide];
N,N'-(dithiodi-2,1-phenylene)bis[1-(3-methylbutyl)-cyclopentanecarboxamide];
N,N'-(dithiodi-2,1-phenylene)bis[1-(3-methylbutyl)-cyclohexanecarboxamide];
N,N'-(dithiodi-2,1-phenylene)bis[1-(2-ethylbutyl)-cyclohexanecarboxamide];
N,N'-(dithiodi-2,1-phenylene)bis-tricyclo[3.3.1.1$^{3,7}$]decane-1-carboxamide;
propanethioic acid, 2-methyl-,S-[2[[[1-(2-ethylbutyl)cyclohexyl]carbonyl]amino]phenyl]ester;
propanethioic acid, 2,2-dimethyl-, S-[2-[[[1-(2-ethylbutyl)cyclohexyl]carbonyl]amino]phenyl]ester; and
ethanethioic acid, S-[2-[[[1-(2-ethylbutyl)cyclohexyl]carbonyl]amino]phenyl]ester.

Another class of CETP inhibitors that finds utility with the present invention consists of polycyclic aryl and heteroaryl tertiary-heteroalkylamines having the Formula XIV

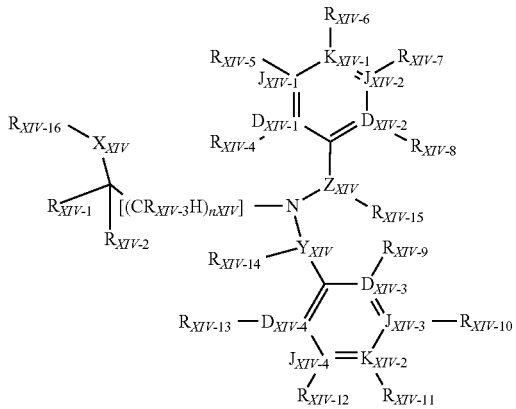

Formula XIV and pharmaceutically acceptable forms thereof, wherein:

$n_{XIV}$ is an integer selected from 0 through 5;

$R_{XIV-1}$ is selected from the group consisting of haloalkyl, haloalkenyl, haloalkoxyalkyl, and haloalkenyloxyalkyl;

$X_{XIV}$ is selected from the group consisting of O, H, F, S, S(O),NH, N(OH), N(alkyl), and N(alkoxy);

$R_{XIV-16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, dialkoxyphosphonoalkyl, trialkylsilyl, and a spacer selected from the group consisting of a covalent single bond and a linear spacer moiety having from 1 through 4 contiguous atoms linked to the point of bonding of an aromatic substituent selected from the group consisting of $R_{XIV-4}$, $R_{XIV-8}$, $R_{XIV-9}$, and $R_{XIV-13}$ to form a heterocyclyl ring having from 5 through 10 contiguous members with the provisos that said spacer moiety is other than a covalent single bond when $R_{XIV-2}$ is alkyl and there is no $R_{XIV-16}$ wherein X is H or F;

$D_{XIV-1}$, $D_{XIV-2}$ $J_{XIV-1}$, $J_{XIV-2}$ and $K_{XIV-1}$ are independently selected from the group consisting of C, N, O, S and a covalent bond with the provisos that no more than one of $D_{XIV-1}$, $D_{XIV-2}$, $J_{XIV-1}$ $J_{XIV-2}$ and $K_{XIV-1}$ is a covalent bond, no more than one of $D_{XIV-1}$, $D_{XIV-2}$, $J_{XIV-1}$, $J_{XIV-2}$ and $K_{XIV-1}$ is O, no more than one of $D_{XIV-1}$ $D_{XIV-2}$, $J_{XIV-1}$, $J_{XIV-2}$ and $K_{XIV-1}$ is S, one of $D_{XIV-1}$, $D_{XIV-2}$, $J_{XIV-1}$, $J_{XIV-2}$ and $K_{XIV-1}$ must be a covalent bond when two of $D_{XIV-1}$, $J_{XIV-1}$, $J_{XIV-2}$ and $K_{XIV-1}$ are O and S, and no more than four of $D_{XIV-1}$, $D_{XIV-2}$, $J_{XIV-1}$, $J_{XIV-2}$ and $K_{XIV-1}$ are N;

$D_{XIV-3}$, $D_{XIV-4}$, $J_{XIV-3}$, $J_{XIV-}4$ and $K_{XIV-2}$ are independently selected from the group consisting of C, N, O, S and a covalent bond with the provisos that no more than one of $D_{XIV-3}$, $D_{XIV-4}$, $J_{XIV-3}$, $J_{XIV-4}$ and $K_{XIV-2}$ is a covalent bond, no more than one of $D_{XIV-3}$, $D_{XIV-4}$, $J_{XIV-3}$, $J_{XIV-4}$ and $K_{XIV-2}$ is O, no more than one of $D_{XIV-3}$, $D_{XIV-}4$, $J_{XIV-3}$, $J_{XIV-4}$ and $K_{XIV-2}$ is S, one of $D_{XIV-3}$, $D_{XIV-4}$, $J_{XIV-3}$, $J_{XIV-}4$ and $K_{XIV-2}$ must be a covalent bond when two of $D_{XIV-3}$, $D_{XIV-4}$, $J_{XIV-3}$, $J_{XIV-4}$ and $K_{XIV-2}$ are O and S, and no more than four of $D_{XIV-3}$, $D_{XIV-4}$, $J_{XIV-3}$, $J_{XIV-4}$ and $K_{XIV-2}$ and $K_{XIV-2}$ are N;

$R_{XIV-2}$ is independently selected from the group consisting of hydrido, hydroxy, hydroxyalkyl, amino, aminoalkyl, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, aloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_{XIV-2}$ and $R_{XIV-3\ are}$ taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_{XIV-3\ is}$ selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy; carboxamide, carboxamidoalkyl, carboaralkoxy, dialkoxyphosphono, diaralkoxyphosphono, dialkoxyphosphonoalkyl, and diaralkoxyphosphonoalkyl;

$Y_{XIV}$ is selected from a group consisting of a covalent single bond, $(C(R_{XIV-14})_2)_{qXIV}$ wherein $_{qXIV}$ is an integer selected from 1 and 2 and $(CH(R_{XIV-14}))_{gXIV}-W_{XIV}-(CH(R_{XIV-14}))_{pXIV}$ wherein $_{gXIV}$ and $_{pXIV}$ are integers independently selected from 0 and 1;

$R_{XIV-14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-9}$ and $R_{XIV-13}$ to form a ring selected from the group consisting of a cycloalkenyl ring having from 5 through 8 contiguous members and a heterocyclyl ring having from 5 through 8 contiguous members and a spacer selected from a moiety having a chain length of 2 to 5 atoms connected to the point of bonding selected from the group consisting of $R_{XIV-4}$ and $R_{XIV-8}$ to form a heterocyclyl having from 5 through 8 contiguous members with the proviso that, when $Y_{XIV}$ is a covalent bond, an $R_{XIV-14}$ substituent is not attached to $Y_{XIV}$;

$R_{XIV-14}$ and $R_{XIV-14}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-14}$ and $R_{XIV-14}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$W_{XIV}$ is selected from the group consisting of O, C(O), C(S), C(O)N($R_{XIV-14}$), C(S)N($R_{XIV-14}$), ($R_{XIV-14}$)NC(O), ($R_{XIV-14}$)NC(S), S, S(O), S(O)$_2$, S(O)$_2$N($R_{XIV-14}$), ($R_{XIV-14}$)NS(O)$_2$, and N($R_{XIV-14}$) with the proviso that $R_{XIV-14}$ is selected from other than halo and cyano;

$Z_{XIV}$ is independently selected from a group consisting of a covalent single bond, (C($R_{XIV-15}$)$_2$)$_{qXIV-2}$ wherein $_{qXIV-2}$ is an integer selected from 1 and 2, (CH($R_{XIV-15}$))$_{jXIV}$—W—(CH($R_{XIV-15}$))$_{kXIV}$ wherein $_{jXIV}$ and $_{kXIV}$ are integers independently selected from 0 and 1 with the proviso that, when $Z_{XIV}$ is a covalent single bond, an $R_{XIV-15}$ substituent is not attached to $Z_{XIV}$;

$R_{XIV-15}$ is independently selected, when $Z_{XIV}$ is (C($R_{XIV-15}$)$_2$)$_{qXIV}$ wherein $_{qXIV}$ is an integer selected from 1 and 2, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroaralkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_{XIV-9}$ and $R_{XIV-13}$ to form a heterocyclyl having from 5 through 8 contiguous members;

$R_{XIV-15}$ and $R_{XIV-15}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-15}$ and $R_{XIV-15}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{XIV-15}$ is independently selected, when $Z_{XIV}$ is (CH($R_{XIV-15}$))$_{jXIV}$—W—(CH($R_{XIV-15}$))$_{kXIV}$ wherein $_{jXIV}$ and $_{kXIV}$ are integers independently selected from 0 and 1, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroaralkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_{XIV-g}$ and $R_{XIV-13}$ to form a heterocyclyl ring having from 5 through 8 contiguous members;

$R_{XIV-4}$, $R_{XIV-5}$, $R_{XIV-6}$ $R_{XIV-7}$, $R_{XIV-8}$, $R_{XIV-9}$, $R_{XIV-10}$, $R_{XIV-11}$, $R_{XIV-12}$, and $R_{XIV-13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl, amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl; haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_{XIV-4}$, $R_{XIV-5}$, $R_{XIV-6}$, $R_{XIV-7}$, and $R_{XIV-8}$ present, that there are one to five non-hydrido ring substituents $R_{XIV-9}$, $R_{XIV-10}$, $R_{XIV-11}$, $R_{XIV-12}$, and $R_{XIV-13}$ present, and $R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are each independently selected to maintain the tetravalent nature of carbon, trivalent nature of nitrogen, the divalent nature of sulfur, and the divalent nature of oxygen;

$R_{XIV-4}$ and $R_{XIV-5}$, $R_{XIV-5}$ and $R_{XIV-6}$, $R_{XIV-6}$ and $R_{XIV-7}$, $R_{XIV-7}$ and $R_{XIV-8}$, $R_{XIV-8}$ and $R_{XIV-9}$, $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XIV}4$ and $R_{XIV-5}$, $R_{XIV-5}$ and $R_{XIV-6}$, $R_{XIV\ and\ RxXIV-7}$, and $R_{XIV-7}$ and $R_{XIV-8}$ are used at the same time and that no more than one of the group consisting of spacer pairs $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are used at the same time;

$R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ are independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ is used at the same time.

Compounds of Formula XIV are disclosed in WO 00/18721, the entire disclosure of which is incorporated by reference.

In a preferred embodiment, the CETP inhibitor is selected from the following compounds of Formula XIV:

3-[[3-(3-trifluoromethoxyphenoxy)phenyl][[3-(1,1,2,2-tetrafluoroethoxy)-phenyl]methyl]amino]-1,1,1-trifluoro-2-propanol;

3-[[3-(3-isopropylphenoxy)phenyl][[3-(1,1,2,2-tetrafluoroethoxy)phenyl]-methyl]amino]-1,1,1-trifluoro-2-propanol;

3-[[3-(3-cyclopropylphenoxy)phenyl][[3-(1,1,2,2-tetrafluoroethoxy)phenyl]-methyl]amino]-1,1,1-trifluoro-2-propanol;

3-[[3-(3-(2-furyl)phenoxy)phenyl][[3-(1,1,2,2-tetrafluoroethoxy)phenyl]-methyl]amino]1,1,1-trifluoro-2-propanol;

3-[[3-(2,3-dichlorophenoxy)phenyl][[3-(1,1,2,2-tetrafluoroethoxy)phenyl]-methyl]amino]-1,1,1-trifluoro-2-propanol;

3-[[3-(4-fluorophenoxy)phenyl][[3-(1,1,2,2-tetrafluoroethoxy)phenyl]-methyl]amino]-1,1,1-trifluoro-2-propanol;

3-[[3-(4-methlylphenoxy)phenyl][[3-(1,1,2,2-tetrafluoroethoxy)phenyl]-methyl]amino]-1,1,1-trifluoro-2-propanol;

3-[[3-(2-fluoro-5-bromophenoxy)phenyl][[3-(1,1,2,2-tetrafluoroethoxy)phenyl]-methyl]amino]-1,1,1-trifluoro-2-propanol;

3-[[3-(4-chloro-3-ethylphenoxy)phenyl][[3-(1,1,2,2-tetrafluoroethoxy)phenyl]-methyl]amino]-1,1,1-trifluoro-2-propanol;

3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

3-[[3-[3-(pentafluoroethyl)phenoxy]phenyl][[3-(1,1,2,2-tetrafluoroethoxy)-phenyl]methyl]amino]-1,1,1-trifluoro-2-propanol;

3-[[3-(3,5-dimethylphenoxy)phenyl][[3-(1,1,2,2-tetrafluoroethoxy)phenyl]-methyl]amino]-1 1,1,1-trifluoro-2-propanol;

3-[[3-(3-ethylphenoxy)phenyl][[3-(1,1,2,2-tetrafluoroethoxy)phenyl]-methyl]amino]-1,1,1-trifluoro-2-propanol;

3-[[3-(3-t-butylphenoxy)phenyl][[3-(1,1,2,2-tetrafluoroethoxy)phenyl]-methyl]amino] 1,1,1-trifluoro-2-propanol;

3-[[3-(3-methylphenoxy)phenyl][[3-(1,1,2,2-tetrafluoroethoxy)phenyl]-methyl]amino]-1,1,1-trifluoro-2-propanol;

3-[[3-(5,6,7,8-tetrahydro-2-naphthoxy)phenyl][[3-(1,1,2,2-tetrafluoroethoxy)phenyl]methyl]amino]-1,1,1-trifluoro-2-propanol;

3-[[3-(phenoxy)phenyl][[3-(1,1,2,2-tetrafluoroethoxy)phenyl]methyl]amino]-1,1,1-trifluoro-2-propanol;

3-[[3-[3-(N,N-dimethylamino)phenoxy]phenyl][[3-(1,1,2,2-tetrafluoroethoxy)phenyl]methyl]amino]-1,1,1-trifluoro-2-propanol;

3-[[[3-(1,1,2,2-tetrafluoroethoxy)phenyl]methyl][3-[[3-(trifluoromethoxy)-phenyl]methoxy]phenyl]amino]-1,1,1-trifluoro-2-propanol;

3-[[[3-(1,1,2,2-tetrafluoroethoxy)phenyl]methyl][3-[[3-(trifluoromethyl)-phenyl]methoxy]phenyl]amino]-1,1,1-trifluoro-2-propanol;

3-[[[3-(1,1,2,2-tetrafluoroethoxy)phenyl]methyl][3-[[3,5-dimethylphenyl]-methoxy]phenyl]amino]-1,1,1-trifluoro-2-propanol;

3-[[[3-(1,1,2,2-tetrafluoroethoxy)phenyl]methyl][3-[[3-(trifluoromethylthio)-phenyl]methoxy]phenyl]amino]-1,11,-trifluoro-2-propanol;

3-[[[3-(1,1,2,2-tetrafluoroethoxy)phenyl]methyl][3-[[3,5-difluorophenyl]-methoxy]phenyl]amino]-1,1,1-trifluoro-2-propanol;

3-[[[3-(1,1,2,2-tetrafluoroethoxy)phenyl]methyl][3-[cyclohexylmethoxy]-phenyl]amino]-1,1,1-trifluoro-2-propanol;

3-[[3-(2-difluoromethoxy-4-pyridyloxy)phenyl][[3-(1,1,2,2-tetrafluoroethoxy)-phenyl]methyl]amino]-1,1,1-trifluoro-2-propanol;

3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

3-[[3-(3-difluoromethoxyphenoxy)phenyl][[3-(1,1,2,2-tetrafluoroethoxy)-phenyl]methyl]amino]-1,1,1-trifluoro-2-propanol;

3-[[[3-(3-trifluoromethylthio)phenoxy]phenyl][[3-(1,1,2,2-tetrafluoroethoxy)-phenyl]methyl]amino]-1,1,1-trifluoro-2-propanol;

3-[[3-(4-chloro-3-trifluoromethylphenoxy)phenyl][[3-(1,1,2,2-tetrafluoroethoxy)-phenyl]methyl]amino]-1,1,1,-trifluoro-2-propanol;

3-[[3-(3-trifluoromethoxyphenoxy)phenyl][[3-(pentafluoroethymethyl]amino]-1,1,1-trifluoro-2-propanol;

3-[[3-(3-isopropylphenoxy)phenyl][[3-(pentafluoroethyl)phenyl]methyl]-amino]-1,1,1-trifluoro-2-propanol;

3-[[3-(3-cyclopropylphenoxy)phenyl][[3-(pentafluoroethyl)phenyl]methyl]-amino]-1,1,1-trifluoro-2-propanol;

3-[[3-(3-(2-furyl)phenoxy)phenyl][[3-(pentafluoroethyl)phenyl]methyl]-amino]-1,1,1-trifluoro-2-propanol;

3-[[3-(2,3-dichlorophenoxy)phenyl][[3-(pentafluoroethyl)phenyl]methyl]-amino]-1,1,1-trifluoro-2-propanol;

3-[[3-(4-fluorophenoxy)phenyl][[3-(pentafluoroethyl)phenyl]methyl]amino]-1,1,1-trifluoro-2-propanol;

3-[[3-(4-methylphenoxy)phenyl][[3-(pentafluoroethyl)phenyl]methyl]amino]-1,1,1-trifluoro-2-propanol;

3-[[3-(2-fluoro-5-bromophenoxy)phenyl][[3-(pentafluoroethyl)phenyl]methyl]-amino]-1,1,1-trifluoro-2-propanol;

3-[[3-(4-chloro-3-ethylphenoxy)phenyl][[3-(pentafluoroethyl)phenyl]methyl]-amino]-1,1,1-trifluoro-2-propanol;

3-[[3-[3-(1,1,2,2-tetrafluoroethoxy)phenoxy]phenyl][[3-(pentafluoroethyl)-phenyl]methyl]amino]-11,1,1-trifluoro-2-propanol;

3-[[3-[3-(pentafluoroethyl)phenoxy]phenyl][[3-(pentafluoroethyl)phenyl]-methyl]amino]-1,1,1-trifluoro-2-propanol;

3-[[3-(3,5-dimethylphenoxy)phenyl][[3-(pentafluoroethyl)phenyl]methyl]-amino]-1,1,1-trifluoro-2-propanol;

3-[[3-(3-ethylphenoxy)phenyl][[3-(pentafluoroethyl)phenyl]methyl]amino]-1,1,1-trifluoro-2-propanol;

3-[[3-(3-t-butylphenoxy)phenyl][[3-(pentafluoroethyl)phenyl]methyl]amino]-1,1,1-trifluoro-2-propanol;

3-[[3-(3-methylphenoxy)phenyl][[3-pentafluoroethyl)phenyl]methyl]amino]-1,1,1-trifluoro-2-propanol;

3-[[3-(5,6,7,8-tetrahydro-2-naphthoxy)phenyl][[3-(pentafluoroethyl)phenyl]-methyl]amino]-1,1,1-trifluoro-2-propanol;

3-[[3-(phenoxy)phenyl][[3-(pentafluoroethyl)phenyl]methyl]amino]-1,1,1-trifluoro-2-propanol;

3-[[3-[3-(N,N-dimethylamino)phenoxy]phenyl][[3-(pentafluoroethyl)phenyl]-methyl]amino]-1,1,1-trifluoro-2-propanol;

3-[[[3-(pentafluoroethyl)phenyl]methyl][3-[[3-(trifluoromethoxy)phenyl]-methoxy]phenyl]amino]-1,1,1-trifluoro-2-propanol;

3-[[[3-(pentafluoroethyl)phenyl]methyl][3-[[3-(trifluoromethyl)phenyl]-methoxy]phenyl]amino]-1,1,1-trifluoro-2-propanol;

3-[[[3-(pentafluoroethyl)phenyl]methyl][3-[[3,5-dimethylphenyl]methoxy]-phenyl]amino]-1,1,1-trifluoro-2-propanol;

3-[[[3-(pentafluoroethyl)phenyl]methyl][3-[[3-(trifluoromethylthio)phenyl]-methoxy]phenyl]amino]-1,1,1-trifluoro-2-propanol;

3-[[[3-(pentafluoroethyl)phenyl]methyl][3-[[3,5-difluorophenyl]methoxy]-phenyl]amino]-1,1,1-trifluoro-2-propanol;

3-[[[3-(pentafluoroethyl)phenyl]methyl][3-[cyclohexylmethoxy]phenyl]-amino]-1,1,-trifluoro-2-propanol;

3-[[3-(2-difluoromethoxy-4-pyridyloxy)phenyl][[3-(pentafluoroethyl)phenyl]-methyl]amino]-1,1,1-trifluoro-2-propanol;

3-[[3-(2-trifluoromethyl-4-pyridyloxy)phenyl][[3-(pentafluoroethyl)phenyl]-methyl]amino]-1,1,1-trifluoro-2-propanol;

3-[[3-(3-difluoromethoxyphenoxy)phenyl][[3-(pentafluoroethyl)phenyl]-30 methyl]amino]-1,1,1-trifluoro-2-propanol;

3-[[[3-(3-trifluoromethylthio)phenoxy]phenyl][[3-(pentafluoroethyl)phenyl]-methyl]amino]-1,1,1-trifluoro-2-propanol;

3-[[3-(4-chloro-3-trifluoromethylphenoxy)phenyl][[3-(pentafluoroethyl)-phenyl]methyl]amino]-1,1,1-trifluoro-2-propanol;

3-[[3-(3-trifluoromethoxyphenoxy)phenyl][[3-(heptafluoropropyl)phenyl]-methyl]amino]-1,1,1-trifluoro-2-propanol;

3-[[3-(3-isopropylphenoxy)phenyl][[3-(heptafluoropropyl)phenyl]methyl]-amino]-1,1,1-trifluoro-2-propanol;

3-[[3-(3-cyclopropylphenoxy)phenyl][[3-(heptafluoropropyl)phenyl]methyl]-amino]-1,1,1-trifluoro-2-propanol;

3-[[3-(3-(2-furyl)phenoxy)phenyl][[3-(heptafluoropropyl)phenyl]methyl]-amino]-1,1,1-trifluoro-2-propanol;

3-[[3-(2,3-dichlorophenoxy)phenyl][[3-(heptafluoropropyl)phenyl]methyl]-amino]-1,1,1-trifluoro-2-propanol;

3-[[3-(4-fluorophenoxy)phenyl][[3-(heptafluoropropyl)phenyl]methyl]amino]-1,1,1-trifluoro-2-propanol;

3-[[3-(4-methylphenoxy)phenyl][[3-(heptafluoropropyl)phenyl]methyl]amino]-1,1,1-trifluoro-2-propanol;

3-[[3-(2-fluoro-5-bromophenoxy)phenyl][[3-(heptafluoropropyl)phenyl]-methyl]amino]-1,1,1-trifluoro-2-propanol;

3-[[3-(4-chloro-3-ethylphenoxy)phenyl][[3-(heptafluoropropyl)phenyl]methyl]-amino]-1,11-trifluoro-2-propanol;

3-[[3-[3-(1,1,2,2-tetrafluoroethoxy)phenoxy]phenyl][[3-(heptafluoropropyl)-phenyl]methyl]amino]-1,1,1-trifluoro-2-propanol;

3-[[3-[3-(pentafluoroethyl)phenoxy]phenyl][[3-(heptafluoropropyl)phenyl]-methyl]amino]-1,1,1-trifluoro-2-propanol;

3-[[3-(3,5-dimethylphenoxy)phenyl][[3-(heptafluoropropyl)phenyl]methyl]-amino]-1,1,1-trifluoro-2-propanol;

3-[[3-(3-ethylphenoxy)phenyl][[3-(heptafluoropropyl)phenyl]methyl]amino]-1,1,1-trifluoro-2-propanol;

3-[[3-(3-t-butylphenoxy)phenyl][[3-(heptafluoropropyl)phenyl]methyl]amino]-1,1,1-trifluoro-2-propanol;

3-[[3-(3-methylphenoxy)phenyl][[3-(heptafluoropropyl)phenyl]methyl]amino]-1,1,-trifluoro-2-propanol;

3-[[3-(5,6,7,8-tetrahydro-2-naphthoxy)phenyl][3-(heptafluoropropyl)phenyl]-methyl]amino]-1,1,1-trifluoro-2-propanol;

3-[[3-(phenoxy)phenyl][[3-(heptafluoropropyl)phenyl]methyl]amino]-1,1,1-trifluoro-2-propanol;

3-[[3-[3-(N,N-dimethylamino)phenoxy]phenyl][[3-(heptafluoropropyl)phenyl]-methyl]amino]-1,1,1-trifluoro-2-propanol;

3-[[[3-(heptafluoropropyl)phenyl]methyl][3-[[3-(trifluoromethoxy)phenyl]-methoxy]phenyl]amino]-1,1,1-trifluoro-2-propanol;

3-[[[3-(heptafluoropropyl)phenyl]methyl][3-[[3-(trifluoromethyl)phenyl]-methoxy]phenyl]amino]-1,1,1-trifluoro-2-propanol;

3-[[[3-(heptafluoropropyl)phenyl]methyl][3-[[3,5-dimethylphenyl]methoxy]-phenyl]amino]-1,1,1-trifluoro-2-propanol;

3-[[[3-(heptafluoropropyl)phenyl]methyl][3-[[3-(trifluoromethylthio)phenyl]-methoxy]phenyl]amino]-1,1,1-trifluoro-2-propanol;

3-[[[3-(heptafluoropropyl)phenyl]methyl][3-[[3,5-difluorophenyl]methoxy]-phenyl]amino]-1,1,1-trifluoro-2-propanol;

3-[[[3-(heptafluoropropyl)phenyl]methyl][3-[cyclohexylmethoxy]phenyl]-amino]-1,1,1-trifluoro-2-propanol;

3-[[3-(2-difluoromethoxy-4-pyridyloxy)phenyl][[3-(heptafluoropropyl)phenyl]-methyl]amino]-1,1,1-trifluoro-2-propanol;

3-[[3-(2-trifluoromethyl-4-pyridyloxy)phenyl][[3-(heptafluoropropyl)phenyl]-methyl]amino]-1,1,1-trifluoro-2-propanol; 3-[[3-(3-difluoromethoxyphenoxy)phenyl][[3-(heptafluoropropyl)phenyl]-methyl]amino]-1,1,1-trifluoro-2-propanol;

3-[[[3-(3-trifluoromethylthio)phenoxy]phenyl][[3-(heptafluoropropyl)phenyl]-methyl]amino]-1,1,1-trifluoro-2-propanol;

3-[[3-(4-chloro-3-trifluoromethylphenoxy)phenyl][[3-(heptafluoropropyl)-phenyl]-methyl]amino]-1,1,1-trifluoro-2-propanol;

3-[[3-(3-trifluoromethoxyphenoxy)phenyl][[2-fluoro-5-(trifluoromethyl)-phenyl]-methyl]amino]-1,1,1-trifluoro-2-propanol;

3-[[3-(3-isopropylphenoxy)phenyl][[2-fluoro-5-(trifluoromethyl)phenyl]-methyl]amino]-1,1,1-trifluoro-2-propanol;

3-[[3-(3-cyclopropylphenoxy)phenyl][[2-fluoro-5-(trifluoromethyl)phenyl]-methyl]amino]-1,1,1-trifluoro-2-propanol;

3-[[3-(3-(2-furyl)phenoxy)phenyl][[2-fluoro-5-(trifluoromethyl)phenyl]-methyl]amino]-1,1,1-trifluoro-2-propanol;

3-[[3-(2,3-dichlorophenoxy)phenyl][[2-fluoro-5-(trifluoromethyl)phenyl]-methyl]amino]-1,1,1-trifluoro-2-propanol;

3-[[3-(4-fluorophenoxy)phenyl][[2-fluoro-5-(trifluoromethyl)phenyl]-methyl]amino]-1,1,1-trifluoro-2-propanol;

3-[[3-(4-methylphenoxy)phenyl][[2-fluoro-5-(trifluoromethyl)phenyl]-methyl]amino]-1,1,1-trifluoro-2-propanol;

3-[[3-(2-fluoro-5-bromophenoxy)phenyl][[2-fluoro-5-(trifluoromethyl)-phenyl]methyl]amino]-1,1,1-trifluoro-2-propanol;

3-[[3-(4-chloro-3-ethylphenoxy)phenyl][[2-fluoro-5-(trifluoromethyl)-phenyl]methyl]amino]-1,1,1-trifluoro-2-propanol;

3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;

3-[[3-[3-(pentafluoroethyl)phenoxy]phenyl][[2-fluoro-5-(trifluoromethyl)-phenyl]-methyl]amino]-1,1,1-trifluoro-2-propanol;

3-[[3-(3,5-dimethylphenoxy)phenyl][[2-fluoro-5-(trifluoromethyl)phenyl]-methyl]amino]-1,1,1-trifluoro-2-propanol;

3-[[3-(3-ethylphenoxy)phenyl][[2-fluoro-5-(trifluoromethyl)phenyl]methyl]-amino]-1,1,1-trifluoro-2-propanol;

3-[[3-(3-t-butylphenoxy)phenyl][[2-fluoro-5-(trifluoromethyl)phenyl]methyl]-amino]-1,1,1-trifluoro-2-propanol;

3-[[3-(3-methylphenoxy)phenyl][[2-fluoro-5-(trifluoromethyl)phenyl]methyl]-amino]-1,1,1-trifluoro-2-propanol;

3-[[3-(5,6,7,8-tetrahydro-2-naphthoxy)phenyl][[2-fluoro-5-(trifluoromethyl)-phenyl]methyl]amino]-1,1,1-trifluoro-2-propanol;

3-[[3-(phenoxy)phenyl][[2-fluoro-5-(trifluoromethyl)phenyl]methyl]amino]-1,1,1-trifluoro-2-propanol;

3-[[3-[3-(N,N-dimethylamino)phenoxy]phenyl][[2-fluoro-5-(trifluoromethyl)phenyl]methyl]amino]-1,1,1-trifluoro-2-propanol;

3-[[[2-fluoro-5-(trifluoromethyl)phenyl]methyl][3-[[3-(trifluoromethoxy)-phenyl]methoxy]phenyl]amino]-1,1,1-trifluoro-2-propanol;

3-[[[2-fluoro-5-(trifluoromethyl)phenyl]methyl][3-[[3-(trifluoromethyl)-phenyl]methoxy]phenyl]amino]-1,1,1-trifluoro-2-propanol;

3-[[[2-fluoro-5-(trifluoromethyl)phenyl]methyl][3-[[3,5-dimethylphenyl]-methoxy]phenyl]amino]-1,1,1-trifluoro-2-propanol;

3-[[[2-fluoro-5-(trifluoromethyl)phenyl]methyl][3-[[3-(trifluoromethylthio)-phenyl]methoxy]phenyl]amino]-1,1,1-trifluoro-2-propanol;

3-[[[2-fluoro-5-(trifluoromethyl)phenyl]methyl][3-[[3,5-difluorophenyl]-methoxy]phenyl]amino]-1,1,1-trifluoro-2-propanol;

3-[[[2-fluoro-5-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-5-(trifluoromethyl)-phenyl]methyl]amino]-1,1,1-trifluoro-2-propanol;

3-[[3-(2-trifluoromethyl-4-pyridyloxy)phenyl][[2-fluoro-5-(trifluoromethyl)-phenyl]methyl]amino]-1,1,1-trifluoro-2-propanol;

3-[[3-(3-difluoromethoxyphenoxy)phenyl][[2-fluoro-5-(trifluoromethyl)-phenyl]methyl]amino]-1,1,1-trifluoro-2-propanol;

3-[[[3-(3-trifluoromethylthio)phenoxy]phenyl][[2-fluoro-5-(trifluoromethyl)-phenyl]methyl]amino]-1,1,1-trifluoro-2-propanol;

3-[[3-(4-chloro-3-trifluoromethylphenoxy)phenyl][[2-fluoro-5-(trifluoromethyl)phenyl]methyl]amino]-1,1,1-trifluoro-2-propanol;

3-[[3-(3-trifluoromethoxyphenoxy)phenyl][[2-fluoro-4-(trifluoromethyl)-phenyl]methyl]amino]-1,1,1-trifluoro-2-propanol;

3-[[3-(3-isopropylphenoxy)phenyl][[2-fluoro-4-(trifluoromethyl)phenyl]-methyl]amino]-1,1,1-trifluoro-2-propanol;

3-[[3-(3-cyclopropylphenoxy)phenyl][[2-fluoro-4-(trifluoromethyl)phenyl]-methyl]amino]-1,1,1-trifluoro-2-propanol;

3-[[3-(3-(2-furyl)phenoxy)phenyl][[2-fluoro-4-(trifluoromethyl)phenyl]-methyl]amino]-1,1,1-trifluoro-2-propanol;

3-[[3-(2,3-dichlorophenoxy)phenyl][[2-fluoro-4-(trifluoromethyl)phenyl]-methyl]amino]-1,1,1-trifluoro-2-propanol;

3-[[3-(4-fluorophenoxy)phenyl][[2-fluoro-4-(trifluoromethyl)phenyl]-methyl]amino]-1,1,1-trifluoro-2-propanol;
3-[[3-(4-methylphenoxy)phenyl][[2-fluoro-4-(trifluoromethyl)phenyl]-methyl]amino]-1,1,1-trifluoro-2-propanol;
3-[[3-(2-fluoro-5-bromophenoxy)phenyl][[2-fluoro-4-(trifluoromethyl)-phenyl]methyl]amino]-1,1,1-trifluoro-2-propanol;
3-[[3-(4-chloro-3-ethylphenoxy)phenyl][[2-fluoro-4-(trifluoromethyl)-phenyl]methyl]amino]-1,1,1-trifluoro-2-propanol;
3-[[3-[3-(1,1,2,2-tetrafluoroethoxy)phenoxy]phenyl][[2-fluoro-4-(trifluoro-methyl)phenyl]methyl]amino]-1,1,1-trifluoro-2-propanol;
3-[[3-[3-(pentafluoroethyl)phenoxy]phenyl][[2-fluoro-4-(trifluoromethyl)-phenyl]methyl]amino]-1,1,1-trifluoro-2-propanol;
3-[[3-(3,5-dimethylphenoxy)phenyl][[2-fluoro-4-(trifluoromethyl)phenyl]-methyl]amino]-1,1,1-trifluoro-2-propanol;
3-[[3-(3-ethylphenoxy)phenyl][[2-fluoro-4-(trifluoromethyl)phenyl]methyl]-amino]-1,1,1-trifluoro-2-propanol;
3-[[3-(3-t-butylphenoxy)phenyl][[2-fluoro-4-(trifluoromethyl)phenyl]methyl]-amino]-1,1,1-trifluoro-2-propanol;
3-[[3-(3-methylphenoxy)phenyl][[2-fluoro-4-(trifluoromethyl)phenyl]methyl]-amino]-1,1,1-trifluoro-2-propanol;
3-[[3-(5,6,7,8-tetrahydro-2-naphthoxy)phenyl][[2-fluoro-4-(trifluoromethyl)-phenyl]methyl]amino]-1,1,1-trifluoro-2-propanol;
3-[[3-(phenoxy)phenyl][[2-fluoro-4-(trifluoromethyl)phenyl]methyl]amino]-1,1,1-trifluoro-2-propanol;
3-[[3-[3-(N,N-dimethylamino)phenoxy]phenyl][[2-fluoro-4-(trifluoromethyl)-phenyl]methyl]amino]-1,1,1-trifluoro-2-propanol;
3-[[[2-fluoro-4-(trifluoromethyl)phenyl]methyl][3-[[3-(trifluoromethoxy)-phenyl]methoxy]phenyl]amino]-1,1,1-trifluoro-2-propanol;
3-[[[2-fluoro-4-(trifluoromethyl)phenyl]methyl][3-[[3-(trifluoromethyl)-phenyl]methoxy]phenyl]amino]-1,1,1-trifluoro-2-propanol;
3-[[[2-fluoro-4-(trifluoromethyl)phenyl]methyl][3-[[3,5-dimethylphenyl]-methoxy]phenyl]amino]-1,1,1-trifluoro-2-propanol;
3-[[[2-fluoro-4-(trifluoromethyl)phenyl]methyl][3-[[3-(trifluoromethylthio)-phenyl]methoxy]phenyl]amino]-1,1,1-trifluoro-2-propanol;
3-[[[2-fluoro-4-(trifluoromethyl)phenyl]methyl][3-[[3,5-difluorophenyl]-methoxy]phenyl]amino]-1,1,1-trifluoro-2-propanol;
3-[[[2-fluoro-4-(trifluoromethyl)phenyl]methyl][3-[cyclohexylmethoxy]-phenyl]amino]-1,1,1-trifluoro-2-propanol;
3-[[3-(2-difluoromethoxy-4-pyridyloxy)phenyl][[2-fluoro-4-(trifluoromethyl)-phenyl]methyl]amino]-1,1,1-trifluoro-2-propanol;
3-[[3-(2-trifluoromethyl-4-pyridyloxy)phenyl][[2-fluoro-4-(trifluoromethyl)-phenyl]methyl]amino]-1,1,1-trifluoro-2-propanol;
3-[[3-(3-difluoromethoxyphenoxy)phenyl][[2-fluoro-4-(trifluoromethyl)-phenyl]methyl]amino]-1,1,1-trifluoro-2-propanol;
3-[[[3-(3-trifluoromethylthio)phenoxy)phenyl][[2-fluoro-4-(trifluoromethyl)-phenyl]methyl]amino]-1,1,1-trifluoro-2-propanol; and
3-[[3-(4-chloro-3-trifluoromethylphenoxy)phenyl][[2-fluoro-4-(trifluoro-methyl)phenyl]methyl]amino]-1,1,1-trifluoro-2-propanol.

Another class of CETP inhibitors that finds utility with the present invention consists of substituted N-Aliphatic-N-Aromatic tertiary-Heteroalkylamines having the Formula XV

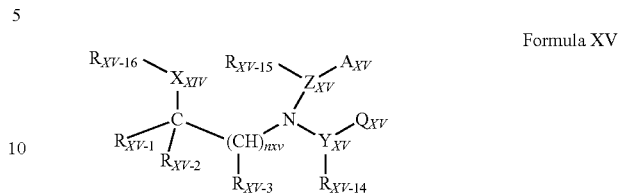

Formula XV and pharmaceutically acceptable forms thereof, wherein:

$n_{XV}$ is an integer selected from 1 through 2;

$A_{XV}$ and $Q_{XV}$ are independently selected from the group consisting of —$CH_2(CR_{XV-37}R_{XV-38})_{vXV}$—$(CR_{XV-33}R_{XV-34})_{uXV}$-$T_{XV}$—$(CR_{XV-35}R_{XV-36})_{wXV}$—H,

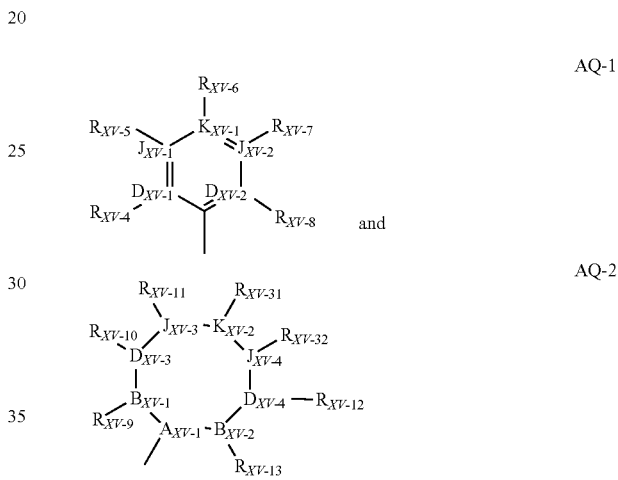

with the provisos that one of $A_{XV}$ and $Q_{XV}$ must be AQ-1 and that one of $A_{XV}$ and $Q_{XV}$ must be selected from the group consisting of AQ-2 and —$CH_2(CR_{XV-37}R_{XV-38})_{vXV}$—$(CR_{XV-33}R_{XV-34})_{uXV}$-$T_{XV}$—$(CR_{XV-35}R_{XV-36})_{wXV}$—H;

$T_{XV}$ is selected from the group consisting of a single covalent bond, O, S, S(O), S(O)$_2$, $C(R_{XV-33})$=$C(R_{XV-35})$, and C≡C;

$_vXV$ is an integer selected from 0 through 1 with the proviso that $_vXV$ is 1 when any one of $R_{XV-33}$, $R_{XV-34}$, $R_{XV-35}$, and $R_{XV-36}$ is aryl or heteroaryl;

$_uXV$ and $_wXV$ are integers independently selected from 0 through 6;

$A_{XV-1}$ is $C(R_{XV-30})$;

$D_{XV-1}$, $D_{XV-2}$, $J_{XV-1}$, $J_{XV-2}$, and $K_{XV-1}$, are independently selected from the group consisting of C, N, O, S and a covalent bond with the provisos that no more than one of $D_{XV-1}$, $D_{XV-2}$, $J_{XV-1}$, $J_{XV-2}$, and $K_{XV-1}$, is a covalent bond, no more than one of $D_{XV-1}$, $D_{XV-2}$, $J_{XV-1}$, $J_{XV-2}$, and $K_{XV-1}$ is O, no more than one of $D_{XV-1}$, $D_{XV-2}$, $J_{XV-1}$, $J_{XV-2}$, and $K_{XV-1}$ is S, one of $D_{XV-1}$, $D_{XV-2}$, $J_{XV-1}$, $J_{XV-2}$, and $K_{XV-1}$ must be a covalent bond when two of $D_{XV-1}$, $D_{XV-2}$, $J_{XV-1}$, $J_{XV-2}$, and $K_{XV}$ are O and S, and no more than four of $D_{XV-1}$, $D_{XV-2}$, $J_{XV-1}$, $J_{XV-2}$, and $K_{XV}$, are N;

$B_{XV-1}$, $B_{XV-2}$, $D_{XV-3}$, $D_{XV-4}$ $J_{XV-3}$, $J_{XV-4}$, and $K_{XV-2}$ are independently selected from the group consisting of C, $C(R_{XV-30})$, N, O, S and a covalent bond with the provisos that no more than 5 of $B_{XV\text{-}1}$, $B_{XV\text{-}2}$, $D_{XV\text{-}3}$, $J_{XV\text{-}4}$, $J_{XV\text{-}3}$, $J_{XV\text{-}4}$, and $K_{XV\text{-}2}$ are a covalent bond, no more than two of $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are 0, no more than two of $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are S, no more than two of $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are simultaneously O and S, and no more than two of $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are N;

$B_{XV\text{-}1}$ and $D_{XV\text{-}3}$, $D_{XV\text{-}3}$ and $J_{XV\text{-}3}$, $J_{XV\text{-}3}$ and $K_{XV\text{-}2}$ $K_{XV\text{-}2}$ and $J_{XV\text{-}4}$, $J_{XV\text{-}4}$ and $D_{XV\text{-}4}$, and $D_{XV\text{-}4}$ and $B_{XV\text{-}2}$ are independently selected to form an in-ring spacer pair wherein said spacer pair is selected from the group consisting of $C(R_{XV\text{-}33})=C(R_{XV\text{-}35})$ and N=N with the provisos that AQ-2 must be a ring of at least five contiguous members, that no more than two of the group of said spacer pairs are simultaneously $C(R_{XV\text{-}33})=C(R_{XV\text{-}35})$ and that no more than one of the group of said spacer pairs can be N=N unless the other spacer pairs are other than $C(R_{XV\text{-}33})=C(R_{XV\text{-}35})$,O, N, and S;

$R_{XV\text{-}1}$ is selected from the group consisting of haloalkyl and haloalkoxymethyl;

$R_{XV\text{-}2}$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl and heteroaryl;

$R_{XV\text{-}3}$ is selected from the group consisting of hydrido, aryl, alkyl, alkenyl, haloalkyl, and haloalkoxyalkyl;

$Y_{XV}$ is selected from the group consisting of a covalent single bond, $(CH_2)_q$ wherein q is an integer selected from 1 through 2 and $(CH_2)_j$—O—$(CH_2)_k$ wherein j and k are integers independently selected from 0 through 1;

$Z_{XV}$ is selected from the group consisting of covalent single bond, $(CH_2)_q$ wherein q is an integer selected from 1 through 2, and $(CH_2)_j$—O—$(CH_2)_k$ wherein j and k are integers independently selected from 0 through 1;

$R_{XV\text{-}4}$, $R_{XV\text{-}8}$, $R_{XV\text{-}9}$ and $R_{XV\text{-}13}$ are independently selected from the group consisting of hydrido, halo, haloalkyl, and alkyl;

$R_{XV\text{-}30}$ is selected from the group consisting of hydrido, alkoxy, alkoxyalkyl, halo, haloalkyl, alkylamino, alkylthio, alkylthioalkyl, alkyl, alkenyl, haloalkoxy, and haloalkoxyalkyl with the proviso that $R_{XV\text{-}30}$ is selected to maintain the tetravalent nature of carbon, trivalent nature of nitrogen, the divalent nature of sulfur, and the divalent nature of oxygen;

$R_{XV\text{-}30}$, when bonded to $A_{XV\text{-}I}$ is taken together to form an intra-ring linear spacer connecting the $A_{XV\text{-}I}$-carbon at the point of attachment of $R_{XV\text{-}30}$ to the point of bonding of a group selected from the group consisting of $R_{XV\text{-}10}$, $R_{XV\text{-}11}$, $R_{XV\text{-}12}$, $R_{XV\text{-}31}$, and $R_{XV\text{-}32}$ wherein said intra-ring linear spacer is selected from the group consisting of a covalent single bond and a spacer moiety having from 1 through 6 contiguous atoms to form a ring selected from the group consisting of a cycloalkyl having from 3 through 10 contiguous members, a cycloalkenyl having from 5 through 10 contiguous members, and a heterocyclyl having from 5 through 10 contiguous members;

$R_{XV\text{-}30}$, when bonded to $A_{XV\text{-}I}$ is taken together to form an intra-ring branched spacer connecting the $A_{XV\text{-}I}$-carbon at the point of attachment of $R_{XV\text{-}30}$ to the points of bonding of each member of any one of substituent pairs selected from the group consisting of susbitituent pairs $R_{XV\text{-}10}$ and $R_{XV\text{-}11}$, $R_{XV\text{-}10}$ and $R_{XV\text{-}31}$, $R_{XV\text{-}10}$ and $R_{XV\text{-}32}$, $R_{XV\text{-}10}$ and $R_{XV\text{-}12}$, $R_{XV\text{-}11}$ and $R_{XV\text{-}31}$, $R_{XV\text{-}11}$ and $R_{XV\text{-}32}$, $R_{XV\text{-}11}$ and $R_{XV\text{-}12}$, $R_{XV\text{-}31}$ and $R_{XV\text{-}32}$, $R_{XV\text{-}31}$ and $R_{XV\text{-}12}$ and $R_{XV\text{-}32}$ and $R_{XV\text{-}12}$ and wherein said intra-ring branched spacer is selected to form two rings selected from the group consisting of cycloalkyl having from 3 through 10 contiguous members, cycloalkenyl having from 5 through 10 contiguous members, and heterocyclyl having from 5 through 10 contiguous members;

$R_{XV\text{-}4}$, $R_{XV\text{-}5}$, $R_{XV\text{-}6}$, $R_{XV\text{-}7}$, $R_{XV\text{-}8}$, $R_{XV\text{-}9}$, $R_{XV\text{-}10}$, $R_{XV\text{-}11}$, $R_{XV\text{-}12}$, $R_{XV\text{-}13}$, $R_{XV\text{-}31}$, $R_{XV\text{-}32}$, $R_{XV\text{-}33}$, $R_{XV\text{-}34}$, $R_{XV\text{-}35}$, and $R_{XV\text{-}36}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, alkylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the provisos that $R_{XV\text{-}4}$, $R_{XV\text{-}5}$, $R_{XV\text{-}6}$, $R_{XV\text{-}7}$, $R_{XV\text{-}8}$, $R_{XV\text{-}9}$, $R_{XV\text{-}10}$, $R_{XV\text{-}11}$, $R_{XV\text{-}12}$, $R_{XV\text{-}13}$, $R_{XV\text{-}31}$, $R_{XV\text{-}32}$, $R_{XV\text{-}33}$, $R_{XV\text{-}34}$, $R_{XV\text{-}35}$, and $R_{XV\text{-}36}$ are each independently selected to maintain the tetravalent nature of carbon, trivalent nature of nitrogen, the divalent nature of sulfur, and the divalent nature of oxygen, that no more than three of the $R_{XV\text{-}33}$ and $R_{XV\text{-}34}$ substituents are simultaneously selected from other than the group consisting of hydrido and halo, and that no more than three of the $R_{XV\text{-}35}$ and $R_{XV\text{-}36}$ substituents are simultaneously selected from other than the group consisting of hydrido and halo;

$R_{XV\text{-}9}$, $R_{XV\text{-}10}$, $R_{XV\text{-}11}$, $R_{XV\text{-}12}$, $R_{XV\text{-}13}$, $R_{XV\text{-}31}$ and $R_{XV\text{-}32}$ are independently selected to be oxo with the provisos that $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are independently selected from the group consisting of C and S, no more than two of $R_{XV\text{-}9}$, $R_{XV\text{-}10}$, $R_{XV\text{-}11}$, $R_{XV\text{-}12}$, $R_{XV\text{-}13}$, $R_{XV\text{-}31}$, and $R_{XV\text{-}32}$ are simultaneously oxo, and that $R_{XV\text{-}9}$, $R_{XV\text{-}10}$, $R_{XV\text{-}11}$, $R_{XV\text{-}12}$, $R_{XV\text{-}13}$, $R_{XV\text{-}31}$, and $R_{XV\text{-}32}$ are each independently selected to maintain the tetravalent nature of carbon, trivalent nature of nitrogen, the divalent nature of sulfur, and the divalent nature of oxygen;

$R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$, $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XV-4}$ and $R_{XV-5}$, $R_{XV-5}$ and $RXV-6$, $R_{XV-6}$ and $R_{XV-7}$, $R_{XV-7}$ and $R_{XV-8}$ is used at the same time and that no more than one of the group consisting of spacer pairs $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$ and $R_{XV-12}$ and $R_{XV-13}$ are used at the same time;

$R_{XV-9}$ and $R_{XV-11}$, $R_{XV-9}$ and $R_{XV-12}$, $R_{XV-9}$ and $R_{XV-13}$ $R_{XV-9}$ and $R_{XV-31}$, $R_{XV-9}$ and $R_{XV-32}$, $R_{XV-10}$ and $R_{XV-12}$, $R_{XV-10}$ and $R_{XV-13}$, $R_{XV-10}$ and $R_{XV-31}$, $R_{XV-10}$ and $R_{XV-32}$, $R_{XV-11}$ and $R_{XV-12}$, $R_{XV-11}$ and $R_{XV-13}$, $R_{XV-11}$ and $R_{XV-32}$, $R_{XV-12}$ and $R_{XV-31}$, $R_{XV-13}$ and $R_{XV-31}$, and $R_{XV-13}$ and $R_{XV-32}$ are independently selected to form a spacer pair wherein said spacer pair is taken together to form a linear spacer moiety selected from the group consisting of a covalent single bond and a moiety having from 1 through 3 contiguous atoms to form a ring selected from the group consisting of a cycloalkyl having from 3 through 8 contiguous members, a cycloalkenyl having from 5 through 8 contiguous members, a saturated heterocyclyl having from 5 through 8 contiguous members and a partially saturated heterocyclyl having from 5 through 8 contiguous members with the provisos that no more than one of said group of spacer pairs is used at the same time;

$R_{XV-37}$ and $R_{XV-38}$ are independently selected from the group consisting of hydrido, alkoxy, alkoxyalkyl, hydroxy, amino, thio, halo, haloalkyl, alkylamino, alkylthio, alkylthioalkyl, cyano, alkyl, alkenyl, haloalkoxy, and haloalkoxyalkyl.

Compounds of Formula XV are disclosed in WO 00/18723, the entire disclosure of which is incorporated by reference.

In a preferred embodiment, the CETP inhibitor is selected from the following compounds of Formula XV:

3-[[3-(4-chloro-3-ethylphenoxy)phenyl](cyclohexylmethyl)amino]-1,1,1-trifluoro-2-propanol;
3-[[3-(4-chloro-3-ethylphenoxy)phenyl](cyclopentylmethyl)amino]-1,1,1-trifluoro-2-propanol;
3-[[3-(4-chloro-3-ethylphenoxy)phenyl](cyclopropylmethyl)amino]-1,1,1-trifluoro-2-propanol;
3-[[3-(4-chloro-3-ethylphenoxy)phenyl][(3-trifluoromethyl)cyclohexyl-methyl]amino]-1,1,1-trifluoro-2-propanol;
3-[[3-(4-chloro-3-ethylphenoxy)phenyl][(3-pentafluoroethyl)cyclohexyl-methyl]amino]-1,1,1-trifluoro-2-propanol;
3-[[3-(4-chloro-3-ethylphenoxy)phenyl][(3-trifluoromethoxy)cyclohexyl-methyl]amino]-1,1,1-trifluoro-2-propanol;
3-[[3-(4-chloro-3-ethylphenoxy)phenyl][[3-(1,1,2,2-tetrafluoroethoxy)cyclo-hexylmethyl]amino]-1,1,1-trifluoro-2-propanol;
3-[[3-(3-trifluoromethoxyphenoxy)phenyl](cyclohexylmethyl)amino]-1,1,1-trifluoro-2-propanol;
3-[[3-(3-trifluoromethoxyphenoxy)phenyl](cyclopentylmethyl)amino]-1,1,1-trifluoro-2-propanol;
3-[[3-(3-trifluoromethoxyphenoxy)phenyl](cyclopropylmethyl)amino]-1,1,1-trifluoro-2-propanol;
3-[[3-(3-trifluoromethoxyphenoxy)phenyl][(3-trifluoromethyl)cyclohexyl-methyl]amino]-1,1,1-trifluoro-2-propanol;
3-[[3-(3-trifluoromethoxyphenoxy)phenyl]](3-pentafluoroethyl)cyclohexyl-methyl]amino]-1,1,1-trifluoro-2-propanol;
3-[[3-(3-trifluoromethoxyphenoxy)phenyl][(3-trifluoromethoxy)cyclohexyl-methyl]amino]-1,1,1-trifluoro-2-propanol;
3-[[3-(3-trifluoromethoxyphenoxy)phenyl][[3-(1,1,2,2-tetrafluoroethoxy)cyclohexyl-methyl]amino]-1,1,1-trifluoro-2-propanol;
3-[[3-(3-isopropylphenoxy)phenyl](cyclohexylmethyl]amino]-1,1,1-trifluoro-2-propanol:
3-[[3-(3-isopropylphenoxy)phenyl](cyclopentylmethyl]amino]-1,1,1-trifluoro-2-propanol;
3-[[3-(3-isopropylphenoxy)phenyl](cyclopropylmethyl)amino]-1,1,1-trifluoro-2-propanol;
3-[[3-(3-isopropylphenoxy)phenyl][(3-trifluoromethyl)cyclohexyl-methyl]amino]-1,11-trifluoro-2-propanol;
3-[[3-(3-isopropylphenoxy)phenyl][(3-pentafluoroethyl)cyclohexyl-methyl]amino]-1,1,1-trifluoro-2-propanol;
3-[[3-(3-isopropylphenoxy)phenyl][(3-trifluoromethoxy)cyclohexyl-methyl]amino]-1,1,1-trifluoro-2-propanol;
3-[[3-(3-isopropylphenoxy)phenyl][[3-(1,1,2,2-tetrafluoroethoxy)cyclohexyl-methyl]amino]-1,1,1-trifluoro-2-propanol;
3-[[3-(2,3-dichlorophenoxy)phenyl](cyclohexylmethyl)amino]-1,1,1-trifluoro-2-propanol;
3-[[3-(2,3-dichlorophenoxy)phenyl](cyclopentylmethyl)amino]-1,1,1-trifluoro-2-propanol;
3-[[3-(2,3-dichlorophenoxy)phenyl](cyclopropylmethy)amino]-1,1,1-trifluoro-2-propanol;
3-[[3-(2,3-dichlorophenoxy)phenyl][(3-trifluoromethyl)cyclohexyl-methyl]amino]-1,1,1-trifluoro-2-propanol;
3-[[3-(2,3-dichlorophenoxy)phenyl][(3-pentafluoroethyl)cyclohexyl-methyl]amino]-1,1,1-trifluoro-2-propanol;
3-[[3-(2,3-dichlorophenoxy)phenyl][(3-trifluoromethoxy)cyclohexyl-methyl]amino]-1,1,1-trifluoro-2-propanol;
3-[[3-(2,3-dichlorophenoxy)phenyl][3-(1,1,2,2-tetrafluoroethoxy)cyclo-hexyl-methyl]amino]-1,1,1-trifluoro-2-propanol;
3-[[3-(4-fluorophenoxy)phenyl](cyclohexylmethyl)amino]-1,1,1-trifluoro-2-propanol;
3-[[3-(4-fluorophenoxy)phenyl](cyclopentylmethyl)amino]-1,1,1-trifluoro-2-propanol;
3-[[3-(4-fluorophenoxy)phennyl](cyclopropylmethyl)amino]-1,1,1-triflouro-2-propanol;
3-[[3-(4-fluorophenoxy)phenyl][(3-trifluoromethyl)cyclohexyl-methyl]amino]-1,1,1-trifluoro-2-propanol;
3-[[3-(4-fluorophenoxy)phenyl][(3-pentafluoroethyl)cyclohexyl-methyl]amino]-1,1,1-trifluoro-2-propanol;
3-[[3-(4-fluorophenoxy)phenyl][(3-trifluoromethoxy)cyclohexyl-methyl]amino]-1,1,1-trifluoro-2-propanol;
3-[[3-(4-fluorophenoxy)phenyl][[3-(1,1,2,2-tetrafluoroethoxy)cyclohexyl-methyl]amino]-1,1,1-trifluoro-2-propanol;
3-[[3-(3-trifluoromethoxybenzyloxy]phenyl](cyclohexylmethyl)amino]-1,1,1-trifluoro-2-propanol;
3-[[3-(3-trifluoromethoxybenzyloxy)phenyl](cyclopentylmethyl)amino]-1,1,1-trifluoro-2-propanol;
3-[[3-(3-trifluoromethoxybenzyloxy)phenyl](cyclopropylmethyl]amino]-1,1,1-trifluoro-2-propanol;
3-[[3-(3-trifluoromethoxybenzyloxy)phenyl][(3-trifluoromethyl)cyclohexyl-methyl]amino]-1,1,1-trifluoro-2-propanol;

3-[[3-(3-trifluoromethoxybenzyloxy)phenyl][(3-pentafluoroethyl)cyclohexyl-methyl]amino]-1,1,1-trifluoro-2-propanol;

3-[[3-(3-trifluoromethoxybenzyloxy)phenyl][(3-trifluoromethoxy)cyclohexyl-methyl]amino]-1,1,1-trifluoro-2-propanol;

3-[[3-(3-trifluoromethoxybenzyloxy)phenyl][3-(1,1,2,2-tetrafluoroethoxy)-cyclohexylmethyl]amino]-1,1,1-trifluoro-2-propanol;

3-[[3-(3-trifluoromethylbenzyloxy)phenyl](cyclohexylmethyl)amino]-1,1,1-trifluoro-2-propanol;

3-[[3-(3-trifluoromethylbenzyloxy)phenyl](cyclopentylmethyl)amino]-1,1,1-trifluoro-2-propanol;

3-[[3-(3-trifluoromethylbenzyloxy)phenyl](cyclopropylmethyl)amino]-1,1,1-trifluoro-2-propanol;

3-[[3-(3-trifluoromethylbenzyloxy)phenyl][(3-trifluoromethyl)cyclohexyl-methyl]amino]-1,1,1-trifluoro-2-propanol;

3-[[3-(3-trifluoromethylbenzyloxy)phenyl][(3-pentafluoroethyl)cyclohexyl-methyl]amino]-1,1,1-trifluoro-2-propanol;

3-[[3-(3-trifluoromethylbenzyloxy)phenyl][(3-trifluoromethoxy)cyclohexyl-methyl]amino]-1,1,1-trifluoro-2-propanol;

3-[[3-(3-trifluoromethylbenzyloxy)phenyl][3-(1,1,2,2-tetrafluoroethoxy)cyclohexyl-methyl]amino]-1,1,1-trifluoro-2-propanol;

3-[[[(3-trifluoromethyl)phenyl]methyl](cyclohexyl)amino]-1,1,1-trifluoro-2-propanol;

3-[[[(3-pentafluoroethyl)phenyl]methyl](cyclohexyl)amino]-1,1,1-trifluoro-2-propanol;

3-[[[(3-trifluoromethoxy)phenyl]methyl](cyclohexyl)amino]-1,1,1-trifluoro-2-propanol;

3-[[[3-(1,1,2,2-tetrafluoroethoxy)phenyl]methyl](cyclohexyl)amino]-1,1,1-trifluoro-2-propanol;

3-[[[(3-trifluoromethyl)phenyl]methyl](4-methylcyclohexyl)amino]-1,1,1-trifluoro-2-propanol;

3-[[[(3-pentafluoroethyl)phenyl]methyl](4-methylcyclohexyl)amino]-1,1,1-trifluoro-2-propanol;

3-[[[(3-trifluoromethoxy)phenyl]methyl](4-methylcyclohexyl)amino]-1,1,1-trifluoro-2-propanol;

3-[[[3-(1,1,2,2-tetrafluoroethoxy)phenyl]methyl](4-methylcyclohexyl)amino]-1,1,1-trifluoro-2-propanol;

3-[[[(3-trifluoromethyl)phenyl]methyl](3-trifluoromethylcyclohexyl)amino]-1,1,1-trifluoro-2-propanol;

3-[[[(3-pentafluoroethyl)phenyl]methyl](3-trifluoromethylcyclohexyl)amino]-1,1,1-trifluoro-2-propanol;

3-[[[(3-trifluoromethoxy)phenyl]methyl](3-trifluoromethylcyclohexyl)amino]-1,1,1-trifluoro-2-propanol;

3-[[[3-(1,1,2,2-tetrafluoroethoxy)phenyl]methyl](3-trifluoromethylcyclohexyl)amino]-1,1,1-trifluoro-2-propanol;

3-[[[(3-trifluoromethyl)phenyl]methyl][3-(4-chloro-3-ethylphenoxy)cyclo-hexyl]amino]-1,1,1-trifluoro-2-propanol;

3-[[[(3-pentafluoroethyl)phenyl]methyl][3-(4-chloro-3-ethylphenoxy)cyclo-hexyl]amino]-1,1,1-trifluoro-2-propanol;

3-[[[(3-trifluoromethoxy)phenyl]methyl][3-(4-chloro-3-ethylphenoxy)cyclo-hexyl]amino]-1,1,1-trifluoro-2-propanol;

3-[[[3-(1,1,2,2-tetrafluoroethoxy)phenyl]methyl][3-(4-chloro-3-ethylphenoxy)-cyclohexyl]amino]-1,1,1-trifluoro-2-propanol;

3-[[[(3-trifluoromethyl)phenyl]methyl](3-phenoxycyclohexyl)amino]-1,1,1-trifluoro-2-propanol;

3-[[[(3-pentafluoroethyl)phenyl]methyl](3-phenoxycyclohexyl)amino]-1,1,1-trifluoro-2-propanol;

3-[[[(3-trifluoromethoxy)phenyl]methyl](3-phenoxycyclohexyl)amino]-1,1,1-trifluoro-2-propanol;

3-[[[3-(1,1,2,2-tetrafluoroethoxy)phenyl]methyl](3-phenoxycyclohexyl)amino]-1,1,1-trifluoro-2-propanol;

3-[[[(3-trifloromethyl)phenyl]methyl](3-isopropoxycyclohexyl)amino]-1,1,1-trifluoro-2-propanol;

3-[[[(3-pentafluoroethyl)phenyl]methyl](3-isopropoxycyclohexyl)amino]-1,1,1-trifluoro-2-propanol;

3-[[[(3-trifluoromethoxy)phenyl]methyl](3-isopropoxycyclohexyl)amino]-1,1,1-trifluoro-2-propanol;

3-[[[3-(1,1,2,2-tetrafluoroethoxy)phenyl]methyl](3-isopropoxycyclohexyl)-amino]-1,1,1-trifluoro-2-propanol;

3-[[[(3-trifluoromethyl)phenyl]methyl](3-cyclopentyloxycyclohexyl]amino]-1,1,1-trifluoro-2-propanol;

3-[[[(3-pentafluoroethyl)phenyl]methyl](3-cyclopentyloxycyclohexyl)amino]-1,1,1-trifluoro-2-propanol;

3-[[[(3-trifluoromethoxy)phenyl]methyl](3-cyclopentyloxycyclohexyl)amino]-1,1,1-trifluoro-2-propanol;

3-[[[3-(1,1,2,2-tetrafluoroethoxy)phenyl]methyl](3-cyclopentyloxycyclohexyl)-amino]-1,1,1-trifluoro-2-propanol;

3-[[[(2-trifluoromethyl)pyrid-6-yl]methyl](3-isopropoxycyclohexyl)amino]-1,1,1-trifluoro-2-propanol;

3-[[[(2-trifluoromethyl)pyrid-6-yl]methyl](3-cyclopentyloxycyclohexyl)-amino]-1,1,1-trifluoro-2-propanol;

3-[[[(2-trifluoromethyl)pyrid-6-yl]methyl](3-phenoxycyclohexyl)amino]-1,1,1-trifluoro-2-propanol;

3-[[[(2-trifluoromethyl)pyrid-6-yl]methyl](3-trifluoromethylcyclohexyl)amino]-1,1,1-trifluoro-2-propanol;

3-[[[(2-trifluoromethyl)pyrid-6-yl]methyl][3-(4-chloro-3-ethylphenoxy)cyclo-hexyl]amino]-1,1,1-trifluoro-2-propanol;

3-[[[(2-trifluoromethyl)pyrid-6-yl]methyl][3-(1,1,2,2-tetrafluoroethoxy)cyclo-hexyl]amino]-1,1,1-trifluoro-2-propanol;

3-[[[(2-trifluoromethyl)pyrid-6-yl]methyl](3-pentafluoroethylcyclohexyl)-amino]-1,1,1-trifluoro-2-propanol;

3-[[[(2-trifluoromethyl)pyrid-6-yl]methyl](3-trifluoromethoxycyclohexyl)-amino]-1,1,1-trifluoro-2-propanol;

3-[[[(3-trifluoromethyl)phenyl]methyl][3-(4-chloro-3-ethylphenoxy)propyl]-amino]-1,1,1-trifluoro-2-propanol;

3-[[[(3-pentafluoroethyl)phenyl]methyl][3-(4-chloro-3-ethylphenoxy)propyl]-amino]-1,1,1-trifluoro-2-propanol;

3-[[[(3-trifluoromethoxy)phenyl]methyl][3-(4-chloro-3-ethylphenoxy)propyl]-amino]-1,1,1-trifluoro-2-propanol;

3-[[[3-(1,1,2,2-tetrafluoroethoxy)phenyl]methyl][3-(4-chloro-3-ethylphenoxy)-propyl]amino]-1,1,1-trifluoro-2-propanol;

3-[[[(3-trifluoromethyl)phenyl]methyl][3-(4-chloro-3-ethylphenoxy)-2,2,-di-fluropropyl]amino]-1,1,1-trifluoro-2-propanol;

3-[[[(3-pentafluoroethyl)phenyl]methyl][3-(4-chloro-3-ethylphenoxy)-2,2-di-fluropropyl]amino]-1,1,1-trifluoro-2-propanol;

3-[[[(3-trifluoromethoxy)phenyl]methyl][3-(4-chloro-3-ethylphenoxy)-2,2,-di-fluropropyl]amino]-1,1,1-trifluoro-2-propanol;

3-[[[3-(1,1,2,2-tetrafluoroethoxy)phenyl]methyl][3-(4-chloro-3-ethylphenoxy)-2,2,-difluropropyl]amino]-1,1,1-trifluoro-2-propanol;

3-[[[(3-trifluoromethyl)phenyl]methyl][3-(isopropoxy)propyl]amino]-1,1,1-trifluoro-2-propanol;

3-[[[(3-pentafluoroethyl)phenyl]methyl][3-(isopropoxy)propyl]amino]-1,1,1-trifluoro-2-propanol;

3-[[[(3-trifluoromethoxy)phenyl]methyl][3-(isopropoxy)propyl]amino]-1,1,1-trifluoro-2-propanol;

3-[[[3-(1,1,2,2-tetrafluoroethoxy)phenyl]methyl]]3-(isopropoxy)propyl]amino]-1,1,1-trifluoro-2-propanol; and
3-[[[3-(1,1,2,2-tetrafluoroethoxy)phenyl]methyl][3-(phenoxy)propyl]amino]-1,1,1-trifluoro-2-propanol.

Another class of CETP inhibitors that finds utility with the present invention consists of (R)-chiral halogenated 1-substituted amino-(n+1)-alkanols having the Formula XVI Formula XVI

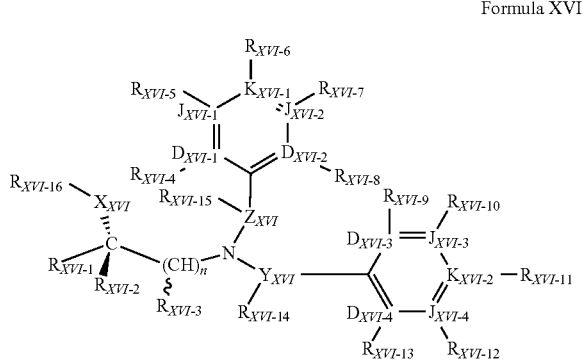

and pharmaceutically acceptable forms thereof, wherein:
$n_{XVI}$ is an integer selected from 1 through 4;
$X_{XVI}$ is oxy;
$R_{XVI-1}$ is selected from the group consisting of haloalkyl, haloalkenyl, haloalkoxymethyl, and haloalkenyloxymethyl with the proviso that $R_{XVI-1}$ has a higher Cahn-lngold-Prelog stereochemical system ranking than both $R_{XVI-2}$ and $(CHR_{XVI-3})_n$—$N(A_{XVI})Q_{XVI}$ wherein $A_{XVI}$ is Formula XVI-(II) and Q is Formula XVI-(II);

XVI-II

XVI-III

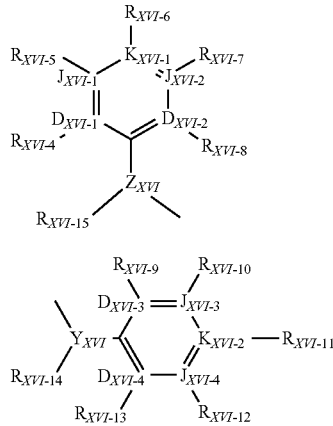

$R_{XVI-16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_{XVI-4}$, $R_{XVI-8}$, $R_{XVI-9}$, and $R_{XVI-13}$ to form a heterocyclyl ring having from 5 through 10 contiguous members;

$D_{XVI-1}$, $D_{XVI-2}$, $J_{XVI-1}$, $J_{XVI-2}$ and $K_{XVI-1}$ are independently selected from the group consisting of C, N, O, S and covalent bond with the provisos that no more than one of $D_{XVI-1}$, $D_{XVI-2}$, $J_{XVI-1}$, $J_{XVI-2}$ and $K_{XVI-1}$ is a covalent bond, no more than one $D_{XVI-1}$, $D_{XVI-2}$, $J_{XVI-1}$, $J_{XVI-2}$ and $K_{XVI-1}$ is be O, no more than one of $D_{XVI-1}$, $D_{XVI-2}$, $J_{XVI-1}$, $J_{XVI-2}$ and $K_{XVI-1}$ is S, one of $D_{XVI-1}$, $D_{XVI-2}$, $J_{XVI-1}$, $J_{XVI-2}$ and $K_{XVI-1}$, must be a covalent bond when two of $D_{XVI-1}$, $D_{XVI-2}$, $J_{XVI-1}$, $J_{XVI-2}$ and $K_{XVI-1}$ are O and S, and no more than four of $D_{XVI-1}$, $D_{XVI-2}$, $J_{XVI-1}$, $J_{XVI-2}$ and $K_{XVI-1}$ is N;

$D_{XVI-3}$, $D_{XVI-4}$, $J_{XVI-3}$, $J_{XVI-4}$ and $K_{XVI-2}$ are independently selected from the group consisting of C, N, O, S and covalent bond with the provisos that no more than one is a covalent bond, no more than one of $D_{XVI-3}$, $D_{XVI-4}$, $J_{XVI-3}$, $J_{XVI-4}$ and $K_{XVI-2}$ is 0, no more than one of $D_{XVI-3}$, $D_{XVI-49}$ $J_{XVI-3}$, $J_{XVI-4}$ and $K_{XVI-2}$ is S, no more than two of $D_{XVI-3}$, $D_{XVI-4}$, $J_{XVI-3}$, $J_{XVI-4}$ and $K_{XVI-2}$ is O and S, one of $D_{XVI-3}$, $D_{XVI-4}$, $J_{XVI-3}$, $J_{XVI-4}$ and $K_{XVI-2}$ must be a covalent bond when two of $D_{XVI-3}$, $D_{XVI-4}$, $J_{XVI-3}$, $J_{XVI-4}$ and $K_{XVI-2}$ are O and S, and no more than four of $D_{XVI-3}$, $D_{XVI-4}$, $J_{XVI-3}$, $J_{XVI-4}$ and $K_{XVI-2}$ are N;

$R_{XVI-2}$ is selected from the group consisting of hydrido, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl, with the proviso that $R_{XVI-2}$ has a lower Cahn-Ingold-Prelog system ranking than both $R_{XVI-1}$ and $(CHR_{XVI-3})_n$—$N(A_{XVI})Q_{XVI}$;

$R_{XVI-3}$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl, with the provisos that $(CHR_{XVI-3})_n$—$N(A_{XVI})Q_{XVI}$ has a lower Cahn-lngold-Prelog stereochemical system ranking than $R_{XVI-1}$ and a higher Cahn-lngold-Prelog stereochemical system ranking than $R_{XVI-2}$;

$Y_{XVI}$ is selected from a group consisting of a covalent single bond, $(C(R_{XVI-14})_2)_q$ wherein q is an integer selected from 1 and 2 and $(CH(R_{XVI-14}))_g$—$W_{XVI}$—$(CH(R_{XVI-14}))_p$ wherein g and p are integers independently selected from 0 and 1;

$R_{XVI-14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$Z_{XVI}$ is selected from a group consisting of a covalent single bond, $(C(R_{XVI-15})_2)_q$, wherein q is an integer selected from 1 and 2, and $(CH(R_{XVI-15}))_j$—$W_{XVI}$-$(CH(R_{XVI}.15))_k$ wherein j and k are integers independently selected from 0 and 1;

$W_{XVI}$ is selected from the group consisting of O, C(O), C(S),C(O)N($R_{XVI-14}$), C(S)N($R_{XVI-14}$),($R_{XVI-14}$)NC(O), ($R_{XVI-14}$)NC(S), S, S(O), S(O)$_2$, S(O)$_2$N($R_{XVI-14}$), ($R_{XVI-14}$)NS(O)$_2$, and N($R_{XVI-14}$) with the proviso that $R_{XVI-14}$ is other than cyano;

$R_{XVI-5}$ is selected, from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are independently selected, from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkyl, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl, amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are each independently selected to maintain the tetravalent nature of carbon, trivalent nature of nitrogen, the divalent nature of sulfur, and the divalent nature of oxygen;

$R_{XVI-4}$ and $R_{XVI-5}$, $R_{XVI-5}$ and $R_{XVI-6}$, $R_{XVI-6}$ and $R_{XVI-7}$, $R_{XVI-7}$ and $R_{XVI-9}$, $R_{XVI-9}$ and $R_{XVI-10}$, $R_{XVI-10}$ and $R_{XVI-11}$, $R_{XVI-11}$ and $R_{XVI-12}$ and $R_{XVI-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XVI-4}$ and $R_{XVI-5}$, $R_{XVI-5}$ and $R_{XVI-6}$, $R_{XVI-6}$ and $R_{XVI-7}$, and $R_{XVI-7}$ and $R_{XVI-8}$ is used at the same time and that no more than one of the group consisting of spacer pairs $R_{XIV-9}$ and $R_{XVI-10}$, $R_{XVI-10}$ and $R_{XVI-11}$, $R_{XVI-11}$ and $R_{XVI-12}$, and $R_{XVI-12}$ and $R_{XV-113}$ can be used at the same time;

$R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XVI-4}$ and $R_{XVI-9}$, $R_{XVI-4}$ and $R_{XVI-13}$, $P_{XVI-8}$ and $R_{XVI-9}$, and $R_{XVI-8}$ and $R_{XVI-13}$ is used at the same time.

Compounds of Formula XVI are disclosed in WO 00/18724, the entire disclosure of which is incorporated by reference.

In a preferred embodiment, the CETP inhibitor is selected from the following compounds of Formula XVI:

(2R)-3-[[3-(3-trifluoromethoxyphenoxy)phenyl][[3-(1,1,2,2-tetrafluoroethoxy)phenyl]methyl]amino]-1,1,1-trifluoro-2-propanol;

(2R)-3-[[3-(3-isopropylphenoxy)phenyl][[3-(1,1,2,2-tetrafluoroethoxy)phenyl]-methyl]amino]-1,1,1-trifluoro-2-propanol;

(2R)-3-[[3-(3-cyclopropylphenoxy)phenyl][[3-(1,1,2,2-tetrafluoroethoxy)phenyl]-methyl]amino]-1,1,1-trifluoro-2-propanol;

(2R)-3-[[3-(3-(2-furyl)phenoxy)phenyl][[3-(1,1,2,2-tetrafluoroethoxy)phenyl]-methyl]amino]-1,1,1-trifluoro-2-propanol;

(2R)-3-[[3-(2,3-dichlorophenoxy)phenyl][[3-(1,1,2,2-tetrafluoroethoxy)phenyl]-methyl]amino]-1,1,1-trifluoro-2-propanol;

(2R)-3-[[3-(4-fluorophenoxy)phenyl][[3-(1,1,2,2-tetrafluoroethoxy)phenyl]-methyl]amino]-1,1,1-trifluoro-2-propanol;

(2R)-3-[[3-(4-methylphenoxy)phenyl][[3-(1,1,2,2-tetrafluoroethoxy)phenyl]-methyl]amino]-1,1,1-trifluoro-2-propanol;

(2R)-3-[[3-(2-fluoro-5-bromophenoxy)phenyl][[3-(1,1,2,2-tetrafluoroethoxy)phenyl]-methyl]amino]-1,1,1-trifluoro-2-propanol;

(2R)-3-[[3-(4-chloro-3-ethylphenoxy)phenyl][[3-(1,1,2,2-tetrafluoroethoxy)phenyl]-methyl]amino]-1,1,1-trifluoro-2-propanol;

(2R)-3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

(2R)-3-[[3-[3-(pentafluoroethyl)phenoxy]phenyl][[3-(1,1,2,2-tetrafluoroethoxy)-phenyl]methyl]amino]-1,1,1-trifluoro-2-propanol;

(2R)-3-[[3-(3,5-dimethylphenoxy)phenyl][[3-(1,1,2,2-tetrafluoroethoxy)phenyl]-methyl]amino]-1,1,1-trifluoro-2-propanol;

(2R)-3-[[3-(3-ethylphenoxy)phenyl][[3-(1,1,2,2-tetrafluoroethoxy)phenyl]-methyl]amino]-1,1,1-trifluoro-2-propanol;

(2R)-3-[[3-(3-t-butylphenoxy)phenyl][[3-(1,1,2,2-tetrafluoroethoxy)phenyl]-methyl]amino]-1,1,1-trifluoro-2-propanol:

(2R)-3-[[3-(3-methylphenoxy)phenyl][[3-(1,1,2,2-tetrafluoroethoxy)phenyl]-methyl]amino]-1,1,1-trifluoro-2-propanol;

(2R)-3-[[3-(5,6,7,8-tetrahydro-2-naphthoxy)phenyl][[3-(1,1,2,2-tetrafluoro-ethoxy)phenyl] methyl]amino]-1,1,1-trifluoro-2-propanol;

(2R)-3-[[3-(phenoxy)phenyl][[3-(1,1,2,2-tetrafluoroethoxy)phenyl]methyl]amino]-1,1,1-trifluoro-2-propanol;

(2R)-3-[[3-[3-(N,N-dimethylamino)phenoxy]phenyl][[3-(1,1,2,2-tetrafluoro-ethoxy)phenyl] methyl]amino]-1,1,1-trifluoro-2-propanol;

(2R)-3-[[[3-(1,1,2,2,-tetrafluoroethoxy)phenyl]methyl][3-[[3-(trifluoromethoxy)-phenyl] methoxy]phenyl]amino]-1,1,1-trifluoro-2-propanol;

(2R)-3-[[[3-(1,1,2,2-tetrafluoroethoxy)phenyl]methyl][3-[[3-(trifluoro-methyl)phenyl] methoxy]phenyl]amino]-1,1,1-trifluoro-2-propanol;

(2R)-3-[[[3-(1,1,2,2-tetrafluoroethoxy)phenyl]methyl][3-[[3,5-dimethylphenyl]-methoxy]phenyl]amino]-1,1,1-trifluoro-2-propanol;

(2R)-3-[[[3-(1,1,2,2-tetrafluoroethoxy)phenyl]methyl][3-[[3-(trifluoromethylthio)-phenyl]methoxy]phenyl]amino]-1,1,1-trifluoro-2-propanol;

(2R)-3-[[[3-(1,1,2,2-tetrafluoroethoxy)phenyl]methyl][3-[[3,5-difluorophenyl]-methoxy]phenyl]amino]-1,1,1-trifluoro-2-propanol;

(2R)-3-[[[3-(1,1,2,2-tetrafluoroethoxy)phenyl]methyl][3-[cyclohexylmethoxy]-phenyl]amino]-1,1,1-trifluoro-2-propanol;

(2R)-3-[[3-(2-difluoromethoxy-4-pyridyloxy)phenyl][[3-(1,1,2,2-tetrafluoroethoxy)-phenyl]methyl]amino]-1,1,1-trifluoro-2-propanol;

(2R)-3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

(2R)-3-[[3-(3-difluoromethoxyphenoxy)phenyl][[3-(1,1,2,2-tetrafluoroethoxy)-phenyl]methyl]amino]-1,1,1-trifluoro-2-propanol;

(2R)-3-[[[3-(3-trifuoromethylthio)phenoxy]phenyl][[3-(1,1,2,2-tetrafluoroethoxy)-phenyl]methyl]amino]-1,1,1-trifluoro-2-propanol;

(2R)-3-[[3-(4-chloro-3-trifluoromethylphenoxy)phenyl][[3-(1,1,2,2-tetrafluoroethoxy)-phenyl]methyl]amino]-1,1,1-trifluoro-2-propanol;

(2R)-3-[[3-(3-trifluoromethoxyphenoxy)phenyl][[3-(pentafluoroethyl)phenyl]-methyl]amino]-1,1,1-trifluoro-2-propanol;

(2R)-3-[[3-(3-isopropylphenoxy)phenyl][[3-(pentafluoroethyl)phenyl]methyl]-amino]-1,1,1-trifluoro-2-propanol;

(2R)-3-[[3-(3-cyclopropylphenoxy)phenyl][[3-(pentafluoroethyl)phenyl]methyl]-amino]-1,1,1-trifluoro-2-propanol;

(2R)-3-[[3-(3-(2-furyl)phenoxy)phenyl][[3-(pentafluoroethyl)phenyl]methyl]-amino]-1,1,1-trifluoro-2-propanol;

(2R)-3-[[3-(2,3-dichlorophenoxy)phenyl][[3-(pentafluoroethyl)phenyl]methyl]-amino]-1,1,1-trifluoro-2-propanol;

(2R)-3-[[3-(4-fluorophenoxy)phenyl][[3-(pentafluoroethyl)phenyl]methyl]amino]-1,1,1-trifluoro-2-propanol;

(2R)-3-[[3-(4-methylphenoxy)phenyl][[3-(pentafluoroethyl)phenyl]methyl]amino]-1,1,1-trifluoro-2-propanol;

(2R)-3-[[3-(2-fluoro-5-bromophenoxy)phenyl][[3-(pentafluoroethyl)phenyl]methyl]amino]-1,1,1-trifluoro-2-propanol;

(2R)-3-[[3-(4-chloro-3-ethylphenoxy)phenyl][[3-(pentafluoroethyl)phenyl]methyl]amino]-1,1,1-trifluoro-2-propanol;

(2R)-3-[[3-[3-(1,1,2,2-tetrafluoroethoxy)phenoxy]phenyl][[3-(pentafluoroethyl)-phenyl]methyl]amino]-1,1,1-trifluoro-2-propanol;

(2R)-3-[[3-[3-(pentafluoroethyl)phenoxy]phenyl][[3-(pentafluoroethyl)phenyl]-methyl]amino]-1,1,1-trifluoro-2-propanol;

(2R)-3-[[3-(3,5-dimethylphenoxy)phenyl][[3-(pentafluoroethyl)phenyl]methyl]amino]-1,1,1-trifluoro-2-propanol;

(2R)-3-[[3-(3-ethylphenoxy)phenyl][[3-(pentafluoroethyl)phenyl]methyl]amino]-1,1,1-trifluoro-2-propanol;

(2R)-3-[[3-(3-t-butylphenoxy)phenyl][[3-(pentafluoroethyl)phenyl]methyl]amino]-1,1,1-trifluoro-2-propanol;

(2R)-3-[[3-(3-methylphenoxy)phenyl][[3-(pentafluoroethyl)phenyl]methyl]amino]-1,1,1-trifluoro-2-propanol;

(2R)-3-[[3-(5,6,7,8-tetrahydro-2-naphthoxy)phenyl][[3-(pentafluoroethyl)phenyl]-methyl]amino]-1,1,1-trifluoro-2-propanol;

(2R)-3-[[3-(phenoxy)phenyl][[3(pentafluoroethyl)phenyl]methyl]amino]-1,1,1-trifluoro-2-propanol;

(2R)-3-[[3-[3-(N,N-dimethylamino)phenoxy]phenyl][[3-(pentafluoroethyl)phenyl]-methyl]amino]-1,1,1-trifluoro-2-propanol;

(2R)-3-[[[3-(pentafluoroethyl)phenyl]methyl][3-[[3-(trifluoromethoxy)phenyl]-methoxy]phenyl]amino]-1,1,1-trifluoro-2-propanol;

(2R)-3-[[[3-(pentafluoroethyl)phenyl]methyl][3-[[3-(trifluoromethyl)-phenyl]-methoxy]phenyl]amino]-1,1,1-trifluoro-2-propanol;

(2R)-3-[[[3-(pentafluoroethyl)phenyl]methyl][3-[[3,5-dimethylphenyl]methoxy]-phenyl]amino]-1,1,1-trifluoro-2-propanol;

(2R)-3-[[[3-(pentafluoroethyl)phenyl]methyl][3-[[3-(trifluoromethylthio)phenyl]-methoxy]-phenyl]amino]-1,1,1-trifluoro-2-propanol;

(2R)-3-[[[3-(pentafluoroethyl)phenyl]methyl][3-[[3,5-difluorophenyl]methoxy]-phenyl]amino]-1,11-trifluoro-2-propanol;

(2R)-3-[[[3-(pentafluoroethyl)phenyl]methyl][3-[cyclohexylmethoxy]phenyl]-amino]-1,1,1-trifluoro-2-propanol;

(2R)-3-[[3-(2-difluoromethoxy-4-pyridyloxy)phenyl][[3-(pentafluoroethyl)phenyl]-methyl]amino]-1,1,1-trifluoro-2-propanol;

(2R)-3-[[3-(2-trifluoromethyl-4-pyridyloxy)phenyl][[3-(pentafluoroethyl)phenyl]-methyl]amino]-1,1,1-trifluoro-2-propanol;

(2R)-3-[[3-(3-difluoromethoxyphenoxy)phenyl][[3-(pentafluoroethyl)phenyl]-methyl]amino]-1,1,1-trifluoro-2-propanol;

(2R)-3-[[[3-(3-trifluoromethylthio)phenoxy]phenyl][[3-(pentafluoroethyl)phenyl]-methyl]amino]-1,1,1-trifluoro-2-propanol;

(2R)-3-[[3-(4-chloro-3-trifluoromethylphenoxy)phenyl][[3-(pentafluoroethyl)-phenyl]methyl]amino]-1,1,1-trifluoro-2-propanol;

(2R)-3-[[3-(3-trifluoromethbxyphenoxy)phenyl][[3-(heptafluoropropyl)phenyl]-methyl]amino]-1,1,1-trifluoro-2-propanol;

(2R)-3-[[3-(3-isopropylphenoxy)phenyl][[3-(heptafluoropropyl)phenyl]methyl]-amino]-1,1,1-trifluoro-2-propanol;

(2R)-3-[[3-(3-cyclopropylphenoxy)phenyl][[3-(heptafluoropropyl)phenyl]methyl]-amino]-1,1,1-trifluoro-2-propanol;

(2R)-3-[[3-(3-(2-furyl)phenoxy)phenyl][[3-(heptafluoropropyl)phenyl]methyl]-amino]-1,1,1-trifluoro-2-propanol;

(2R)-3-[[3-(2,3-dichlorophenoxy)phenyl][[3-(heptafluoropropyl)phenyl]methyl]-amino]-1,1,1-trifluoro-2-propanol;

(2R)-3-[[3-(4-fluorophenoxy)phenyl][[3-(heptafluoropropyl) phenyl]methyl]amino]-1,1,1-trifluoro-2-propanol;

(2R)-3-[[3-(4-methylphenoxy)phenyl][[3-(heptafluoropropyl) phenyl]methyl]amino]-1,1,1,-trifluoro-2-propanol;

(2R)-3-[[3-(2-fluoro-5-bromophenoxy)phenyl][[3-(heptafluoropropyl)phenyl]-methyl]amino]-1,1,1-trifluoro-2-propanol;

(2R)-3-[[3-(4-chloro-3-ethylphenoxy)phenyl][[3-(heptafluoropropyl)phenyl]methyl]-amino]-1,1,1-trifluoro-2-propanol;

(2R)-3-[[3-[3-(1,1,2,2-tetrafluoroethoxy)phenoxy]phenyl][[3-(heptafluoropropyl)-phenyl]methyl]amino]-1,1,1-trifluoro-2-propanol;

(2R)-3-[[3-[3-(pentafluoroethyl)phenoxy]phenyl][[3-(heptafluoropropyl)phenyl]-methyl]amino]-1,1,1-trifluoro-2-propanol;

(2R)-3-[[3-(3,5-dimethylphenoxy)phenyl][[3-(heptafluoropropyl) phenyl]methyl]-amino]-1,1,1-trifluoro-2-propanol;
(2R)-3-[[3-(3-ethylphenoxy)phenyl][[3-(heptafluoropropyl)phenyl]methyl]amino]-1,1,1-trifluoro-2-propanol;
(2R)-3-[[3-(3-t-butylphenoxy)phenyl][[3-(heptafluoropropyl) phenyl]methyl]amino]-1,1,1-trifluoro-2-propanol;
(2R)-3-[[3-(3-methylphenoxy)phenyl][[3-(heptafluoropropyl) phenyl]methyl]amino]-1,1,1-trifluoro-2-propanol;
(2R)-3-[[3-(5,6,7,8-tetrahydro-2-naphthoxy)phenyl][[3-(heptafluoropropyl)phenyl]-methyl]amino]-1,1,1-trifluoro-2-propanol;
(2R)-3-[[3-(phenoxy)phenyl][[3-(heptafluoropropyl)phenyl]methyl]amino]-1,1,1-4trifluoro-2-propanol;
(2R)-3-[[3-[3-(N,N-dimethylamino)phenoxy]phenyl][[3-(heptafluoropropyl)phenyl]-methyl]amino]-1,1,1-trifluoro-2-propanol;
(2R)-3-[[[3-(heptafluoropropyl)phenyl]methyl][3-[[3-(trifluoromethoxy)phenyl]-methoxy]phenyl]amino]-1,1,1-trifluoro-2-propanol;
(2R)-3-[[[3-(heptafluoropropyl)phenyl]methyl][3-[[3-(trifluoromethyl)phenyl]-methoxy]phenyl]amino]-1,1,1-trifluoro-2-propanol;
(2R)-3-[[[3-(heptafluoropropyl)phenyl]methyl][3-[[3,5-dimethylphenyl]methoxy]-phenyl]amino]-1,1,1-trifluoro-2-propanol;
(2R)-3-[[[3-(heptafluoropropyl)phenyl]methyl][3-[[3-(trifluoromethylthio)phenyl]-methoxy]phenyl]amino]-1,1,1-trifluoro-2-propanol;
(2R)-3-[[[3-(heptafluoropropyl)phenyl]methyl][3-[[3,5-difluorophenyl]methoxy]-phenyl]amino]-1,1,1-trifluoro-2-propanol;
(2R)-3-[[[3-(heptafluoropropyl)phenyl]methyl][3-[cyclohexylmethoxy]phenyl]-amino]-1,1,1-trifluoro-2-propanol;
(2R)-3-[[3-(2-difluoromethoxy-4-pyridyloxy)phenyl][[3-(heptafluoropropyl)phenyl]-methyl]amino]-1,1,1-trifluoro-2-propanol;
(2R)-3-[[3-(2-trifluoromethyl-4-pyridyloxy)phenyl][[3-(heptafluoropropyl)phenyl]-methyl]amino]-1,1,1-trifluoro-2-propanol;
(2R)-3-[[3-(3-difluoromethoxyphenoxy)phenyl][[3-(heptafluoropropyl)phenyl]-methyl]amino]-1,1,1-trifluoro-2-propanol;
(2R)-3-[[[3-(3-trifluoromethylthio)phenoxy]phenyl][[3-(heptafluoropropyl)phenyl]-methyl]amino]-1,1,1-trifluoro-2-propanol;
(2R)-3-[[3-(4-chloro-3-trifluoromethylphenoxy)phenyl][[3-(heptafluoropropyl)-phenyl]methyl]amino]-1,1,1-trifluoro-2-propanol;
(2R)-3-[[3-(3-trifluoromethoxyphenoxy)phenyl][[2-fluoro-5-(trifluoromethyl)-phenyl]methyl]amino]-1,1,1-trifluoro-2-propanol;
(2R)-3-[[3-(3-isopropylphenoxy)phenyl][[2-fluoro-5-(trifluoromethyl)phenyl]-methyl]amino]-1,1,1-trifluoro-2-propanol;
(2R)-3-[[3-(3-cyclopropylphenoxy)phenyl][[2-fluoro-5-(trifluoromethyl)phenyl]-methyl]amino]-1,1,1-trifluoro-2-propanol;
(2R)-3-[[3-(3-(2-furyl)phenoxy)phenyl][[2-fluoro-5-(trifluoromethyl)phenyl]-methyl]amino]-1,1,1-trifluoro-2-propanol;
(2R)-3-[[3-(2,3-dichlorophenoxy)phenyl][[2-fluoro-5-(trifluoromethyl)phenyl]-methyl]amino]-1,1,1-trifluoro-2-propanol;
(2R)-3-[[3-(4-fluorophenoxy)phenyl][[2-fluoro-5-(trifluoromethyl)phenyl]-methyl]amino]-1,1,1-trifluoro-3-propanol;
(2R)-3-[[3-(4-methylphenoxy)phenyl][[2-fluoro-5-(trifluoromethyl)phenyl]-methyl]amino]-1,1,1-trifluoro-2-propanol;
(2R)-3-[[3-(2-fluoro-5-bromophenoxy)phenyl][[2-fluoro-5-(trifluoromethyl)-phenyl]methyl]amino]-1,1,1-trifluoro-2-propanol;
(2R)-3[[3-(4-chloro-3-ethylphenoxy)phenyl][[2-fluoro-5-(trifluoromethyl)-phenyl]methyl]amino]-1,1,1-trifluoro-2-propanol;
(2R)-3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;
(2R)-3-[[3-[3-(pentafluoroethyl)phenoxy]phenyl][[2-fluoro-5-(trifluoromethyl)-phenyl]methyl]amino]-1,1-trifluoro-2-propanol;
(2R)-3-[[3-(3,5-dimethylphenoxy)phenyl][[2-fluoro-5-(trifluoromethyl)phenyl]-methyl]amino]-1,1,1-trifluoro-2-propanol;
(2R)-3-[[3-(3-ethylphenoxy)phenyl][[2-fluoro-5-(trifluoromethyl)phenyl]methyl]-amino]-1,1,1-trifluoro-2-propanol;
(2R)-3-[[3-(3-t-butylphenoxy)phenyl][[2-fluoro-5-(trifluoromethyl)phenyl]methyl]-amino]-1,1,1-trifluoro-2-propanol;
(2R)-3-[[3-(3-methylphenoxy)phenyl][[2-fluoro-5-(trifluoromethyl)phenyl]methyl]-amino]-1,1,1-trifluoro-2-propanol;
(2R)-3-[[3-(5,6,7,8-tetrahydro-2-naphthoxy)phenyl][[2-fluoro-5-(trifluoromethyl)-phenyl]methyl]amino]-1,1,1-trifluoro-2-propanol;
(2R)-3-[[3-(phenoxy)phenyl][[2-fluoro-5-(trifluoromethyl)phenyl]methyl]amino]-1,1,1-trifluoro-2-propanol;
(2R)-3-[[3-[3-(N,N-dimethylamino,phenoxy]phenyl][[2-fluoro-5-(trifluoromethyl)-phenyl]methyl]amino]-1,1,1-trifluoro-2-propanol;
(2R)-3-[[[2-fluoro-5-(trifluoromethyl)phenyl]methyl][3-[[3-(trifluoromethoxy)-phenyl]methoxy]phenyl]amino]-1,1,1-trifluoro-3-propanol;
(2R)-3-[[[2-fluoro-5-(trifluoromethyl)phenyl]methyl][3-[[3-(trifluoromethyl)-phenyl]methoxy]phenyl]amino]-1,1,1-trifluoro-2-propanol;
(2R)-3-[[[2-fluoro-5-(trifluoromethyl)phenyl]methyl][3-[[3,5-dimethylphenyl]-methoxy]phenyl]amino]-1,1,1-trifluoro-2-propanol;
(2R)-3-[[[2-fluoro-5-(trifluoromethyl)phenyl]methyl][3-[[3-(trifluoromethylthio)-phenyl]methoxy]phenyl]amino]-1,1,1-trifluoro-2-propanol;
(2R)-3-[[[2-fluoro-5-(trifluoromethyl)phenyl]methyl][3-[[3,5-difluorophenyl]-methoxy]phenyl]amino]-1,1,1-trifluoro-2-propanol;
(2R)-3-[[[2-fluoro-5-(trifluoromethyl)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[2-fluoro-5-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-5-(trifluoromethyl)-phenyl]methyl]amino]-1,1,1-trifluoro-2-propanol;
(2R)-3-[[3-(3-difluoromethoxyphenoxy)phenyl][[2-fluoro-5-(trifluoromethyl)-phenyl]methyl]amino]-1,1,1-trifluoro-2-propanol;

(2R)-3-[[[3-(3-trifluoromethylthio)phenoxy]phenyl][[2-fluoro-5-(trifluoromethyl)-phenyl]methyl]amino]-1,1,1-trifluoro-2-propanol;

(2R)-3-[[3-(4-chloro-3-trifluoromethylphenoxy)phenyl][[2-fluoro-5-(trifluoro-methyl)phenyl]methyl]amino]-1,1,1-trifluoro-2-propanol;

(2R)-3-[[3-(3-trifluoromethoxyphenoxy)phenyl][[2-fluoro-4-(trifluoromethyl)-phenyl]methyl]amino]-1,1,1-trifluoro-2-propanol;

(2R)-3-[[3-(3-isopropylphenoxy)phenyl][[2-fluoro-4-(trifluoromethyl)phenyl]-methyl]amino]-1,1,1-trifluoro-2-propanol;

(2R)-3-[[3-(3-cyclopropylphenoxy)phenyl][[2-flouro-4-(trifluoromethyl)phenyl]-methyl]amino]-1,1,1-trifluoro-2-propanol;

(2R)-3-[[3-(3-(2-furyl)phenoxy)phenyl][[2-fluoro-4-(trifluoromethyl)phenyl]-methyl]amino]-1,1,1-trifluoro-2-propanol;

(2R)-3-[[3-(2,3-dichlorophenoxy)phenyl][[2-fluoro-4-(trifluoromethyl)phenyl]-methyl]amino]-1,1,1-trifluoro-2-propanol;

(2R)-3-[[3-(4-fluorophenoxy)phenyl][[2-fluoro-4-(trifluoromethyl)phenyl]-methyl]amino]-1,1,1-trifluoro-2-propanol;

(2R)-3-[[3-(4-methylphenoxy)phenyl][[2-fluoro-4-(trifluoromethyl)phenyl]-methyl]amino]-1,1,1-trifluoro-2-propanol;

(2R)-3-[[3-(2-fluoro-5-bromophenoxy)phenyl][[2-fluoro-4-(trifluoromethyl)-phenyl]methyl]amino]-1,1,1-trifluoro-2-propanol;

(2R)-3-[[3-(4-chloro-3-ethylphenoxy)phenyl][[2-fluoro-4-(trifluoromethyl)-phenyl]methyl]amino]-1,1,1-trifluoro-2-propanol;

(2R)-3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;

(2R)-3-[[3-[3-(pentafluoroethyl)phenoxy]phenyl][[2-fluoro-4-(trifluoromethyl)-phenyl]methyl]amino]-1,1,1-trifluoro-2-propanol;

(2R)-3-[[3-(3,5-dimethylphenoxy)phenyl][[2-fluoro-4-(trifluoromethyl)phenyl]-methyl]amino]-1,1,1-trifluoro-2-propanol;

(2R)-3-[[3-(3-ethylphenoxy)phenyl][[2-fluoro-4-(trifluoromethyl)phenyl]methyl]-amino]-1,1, 1-trifluoro-2-propanol;

(2R)-3-[[3-(3-t-butylphenoxy)phenyl][[2-fluoro-4-(trifluoromethyl)phenyl]methyl]-amino]-1,1,1-trifluoro-2-propanol;

(2R)-3-[[3-(3-methylphenoxy)phenyl][[2-fluoro-4-(trifluoromethyl)phenyl]methyl]-amino]-1,1,1-trifluoro-2-propanol;

(2R)-3-[[3-(5,6,7,8-tetrahydro-2-naphthoxy)phenyl][[2-fluoro-4-(trifluoromethyl)-phenyl]methyl]amino]-1,1,1-trifluoro-2-propanol;

(2R)-3-[[3-(phenoxy)phenyl][[2-fluoro-4-(trifluoromethyl)phenyl]methyl]amino]-1,1,1-trifluoro-2-propanol;

(2R)-3-[[3-[3-(N,N-dimethylamino)phenoxy]phenyl][[2-fluoro -4-(trifluoromethyl)-phenyl]methyl]amino]-1,1,1-trifluoro-2-propanol;

(2R)-3-[[[2-fluoro-4-(trifluoromethyl)phenyl]methyl][3-[[3-(trifluoromethoxy)phenyl]methoxy]phenyl]amino]-1,1,1-trifluoro -2-propanol;

(3R)-3-[[[2-fluoro-4-(trifluoromethyl)phenyl]methyl][3-[[3-(trifluoromethyl)phenyl]methoxy]phenyl]amino]-1,1,1-trifluoro-2-propanol;

(2R)-3-[[[2-fluoro-4-(trifluoromethyl)phenyl]methyl][3-[[3,5-dimethylphenyl]-methoxy]phenyl]amino]-1,1,1-trifluoro-2-propanol;

(2R)-3-[[[2-fluoro-4-(trifluoromethyl)phenyl]methyl][3-[[3-(trifluoromethylthio)-phenyl]methoxy]phenyl]amino]-1,1,1-trifluoro-2-propanol;

(2R)-3-[[[2-fluoro-4-(trifluoromethyl)phenyl]methyl][3-[[3,5-difluorophenyl]-methoxy]phenyl]amino]-1,1,1-trifluoro-2-propanol;

(2R)-3-[[[2-fluoro-4-(trifluoromethyl)phenyl]methyl][3-[cyclohexylmethoxy]-phenyl]amino]-1,1,1-trifluoro-2-propanol;

(2R)-3-[[3-(2-difluoromethoxy-4-pyridyloxy)phenyl][[2-fluoro-4-(trifluoromethyl)-phenyl]methyl]amino]-1,1,1-trifluoro-2-propanol;

(2R)-3-[[3-(2-trifluoromethyl-4-pyridyloxy)phenyl][[2-fluoro-4-(trifluoromethyl)-phenyl]methyl]amino]-1,1,1-trifluoro-2-propanol;

(2R)-3-[[3-(3-difluoromethoxyphenoxy)phenyl][[2-fluoro-4-(trifluoromethyl)-phenyl]methyl]amino]-1,1,1-trifluoro-2-propanol;

(2R)-3-[[[3-(3-trifluoromethylthio)phenoxy]phenyl][[2-fluoro-4-(trifluoromethyl)-phenyl]methyl]amino]-1,1,1-trifluoro-2-propanol; and (2R)-3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of quinolines of Formula XVII

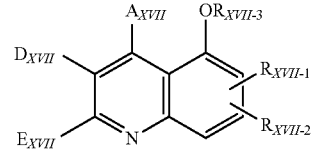

Formula XVII and pharmaceutically acceptable forms thereof, wherein:

$A_{XVII}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$NR_{XVII-4}R_{XVII-5}$, wherein $R_{XVII-4}$ and $R_{XVII-5}$ are identical or different and denote a hydrogen, phenyl or a straight-chain or branched alkyl containing up to 6 carbon atoms, $D_{XVII}$ denotes an aryl containing 6 to 10 carbon atoms, which is optionally substituted with a phenyl, nitro, halogen, trifluoromethyl or trifluoromethoxy, or a radical according to the formula

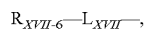

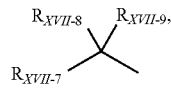

or $R_{XVII-10}$—$T_{XVII}$—$V_{XVII}$—$X_{XVII}$— wherein $R_{XVII-6}$, $R_{XVII-7}$, $R_{XVII-10}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5to 7-membered heterocycle containing up to 3 heteoatoms from the series of S, N and/or O, and/or in the form of a group according to the formula —$OR_{XVII-11}$, —$SR_{XVII-12}$, —$SO_2R_{XVII-13}$, or —$NR_{XVII-14}R_{XVII-15}$;

$R_{XVII-11}$, $R_{XVII-12}$, and $R_{XVII-13}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{XVII-14}$ and $R_{XVII-15}$ are identical or different and have the meaning of $R_{XVII-4}$ and $R_{XVII-5}$ given above, or $R_{XVII-6}$ and/or $R_{XVII-7}$ denote a radical according to the formula

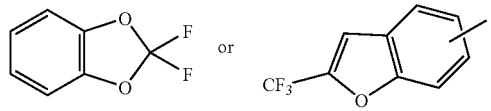

$R_{XVII-8}$ denotes a hydrogen or halogen, and $R_{XVII-9}$ denotes a hydrogen, halogen, azido, trifluoromethyl, hydroxyl, trifluoromethoxy, a straight-chain or branched alkoxy or alkyl containing up to 6 carbon atoms each, or a radical according to the formula $NR_{XVII-16}R_{XVII-17}$;

$R_{XVII-16}$ and $R_{XV-17}$ are identical or different and have the meaning of $R_{XVI-4}$ and $R_{XVII-5}$ above; or $R_{XVII-8}$ and $R_{XVII-9}$ together form a radical according to the formula =O or =$NR_{XVII-18}$;

$R_{XVII-18}$ denotes a hydrogen or a straight-chain or branched alkyl, alkoxy or acyl containing up to 6 carbon atoms each;

$L_{XVII}$ denotes a straight-chain or branched alkylene or alkenylene chain containing up to 8 carbon atoms each, which are optionally substituted with up to two hydroxyl groups;

$T_{XVII}$ and $X_{XVII}$ are identical or different and denote a straight-chain or branched alkylene chain containing up to 8 carbon atoms; or $T_{XVII}$ and $X_{XVII}$ denotes a bond;

$V_{XVII}$ denotes an oxygen or sulfur atom or —$NR_{XVII-19}$;

$R_{XVII-19}$ denotes a hydrogen or a straight-chain or branched alkyl containing up to 6 carbon atoms or a phenyl;

$E_{XVII}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl;

$R_{XVII-1}$ and $R_{XVII-2}$ are identical or different and denote a cycloalkyl containing 3 to 8 carbon atoms, hydrogen, nitro, halogen, trifluoromethyl, trifluoromethoxy, carboxy, hydroxy, cyano, a straight-chain or branched acyl, alkoxycarbonyl or alkoxy with up to 6 carbon atoms, or $NR_{XVII-20}R_{XVII-21}$;

$R_{XVII-20}$ and $R_{XVII-21}$ are identical or different and denote hydrogen, phenyl, or a straight-chain or branched alkyl with up to 6 carbon atoms; and or $R_{XVII-1}$ and/or $R_{XVII-2}$ are straight-chain or branched alkyl with up to 6 carbon atoms, optionally substituted with halogen, trifluoromethoxy, hydroxy, or a straight-chain or branched alkoxy with up to 4 carbon atoms, aryl containing 6-10 carbon atoms optionally substituted with up to five of the same or different substituents selected from halogen, cyano, hydroxy, trifluoromethyl, trifluoromethoxy, nitro, straight-chain or branched alkyl, acyl, hydroxyalkyl, alkoxy with up to 7 carbon atoms and $NR_{XVII-22}R_{XVII-23}$;

$R_{XVII-22}$ and $R_{XVII-23}$ are identical or different and denote hydrogen, phenyl or a straight-chain or branched akyl up to 6 carbon atoms; and/or $R_{XVII-1}$ and $R_{XVII-2}$ taken together form a straight-chain or branched alkene or alkane with up to 6 carbon atoms optionally substituted with halogen, trifluoromethyl, hydroxy or straight-chain or branched alkoxy with up to 5 carbon atoms;

$R_{XVII-3}$ denotes hydrogen, a straight-chain or branched acyl with up to 20 carbon atoms, a benzoyl optionally substituted with halogen, trifluoromethyl, nitro or trifluoromethoxy, a straight-chained or branched fluoroacyl with up to 8 carbon atoms and 7 fluoro atoms, a cycloalkyl with 3 to 7 carbon atoms, a straight chained or branched alkyl with up to 8 carbon atoms optionally substituted with hydroxyl, a straight-chained or branched alkoxy with up to 6 carbon atoms optionally substituted with phenyl which may in turn be substituted with halogen, nitro, trifluoromethyl, trifluoromethoxy, or phenyl or a tetrazol substitued phenyl, and/or an alkyl that is optionally substituted with a group according to the formula —$OR_{XVII-24}$;

$R_{XVII-24}$ is a straight-chained or branched acyl with up to 4 carbon atoms or benzyl.

Compounds of Formula XVII are disclosed in WO 98/39299, the entire disclosure is incorporated by reference.

Another class of CETP inhibitors that finds utility with the present invention consists of 4-Phenyltetrahydroquinolines of Formula XVIII

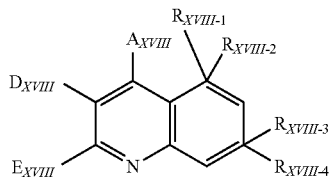

Formula XVIII

N oxides thereof, and pharmaceutically acceptable forms thereof, wherein:

$A_{XVII}$ denotes a phenyl optionally substituted with up to two identical or different substituents in the form of halogen, trifluoromethyl or a straight-chain or branched alkyl or alkoxy containing up to three carbon atoms;

$D_{XVII}$ denotes the formula

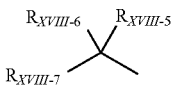

or $R_{XVIII\text{-}8}$—CH$_2$—O—CH$_2$—;

$R_{XVII\text{-}5}$ and $R_{XVII\text{-}6}$ are taken together to form =O; or $R_{XVII\text{-}5}$ denotes hydrogen and $R_{XVII\text{-}6}$ denotes halogen or hydrogen; or $R_{XVIII\text{-}5}$ and $R_{XVII\text{-}6}$ denote hydrogen;

$R_{XVII\text{-}7}$ and $R_{XVII\text{-}8}$ are identical or different and denote phenyl, naphthyl, benzothiazolyl, quinolinyl, pyrimidyl or pyridyl with up to four identical or different substituents in the form of halogen, trifluoromethyl, nitro, cyano, trifluoromethoxy, —SO$_2$—CH$_3$ or NR$_{XVII\text{-}9}$R$_{XVII\text{-}10}$;

$R_{XVII\text{-}9}$ and $R_{XVII\text{-}10}$ are identical or different and denote hydrogen or a straight-chained or branched alkyl of up to three carbon atoms;

$E_{XVII}$ denotes a cycloalkyl of from three to six carbon atoms or a straight-chained or branched alkyl of up to eight carbon atoms;

$R_{XVII\text{-}1}$ denotes hydroxy;

$R_{XVII\text{-}2}$ denotes hydrogen or methyl;

$R_{XVII\text{-}3}$ and $R_{XVII\text{-}4}$ are identical or different and denote straight-chained or branched alkyl of up to three carbon atoms; or $R_{XVII\text{-}3}$ and $R_{XVII\text{-}4}$ taken together form an alkenylene made up of between two and four carbon atoms.

Compounds of Formula XVIII are disclosed in WO 99/15504, the entire disclosure of which is incorporated by reference.

Another class of CETP inhibitors that finds utility with the present invention consists of aminoethanol derivatives of Formula XIX

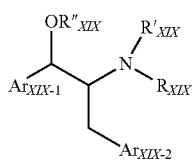

Formula XIX and pharmaceutically acceptable forms thereof, wherein:

Ar$_{XIX\text{-}1}$ denotes an aromatic ring group that may contain a substituting group;

Ar$_{XIX\text{-}2}$ denotes an aromatic ring group that may contain a substituting group;

R$_{XIX}$ denotes an acyl group;

R'$_{XIX}$ denotes a hydrogen atom or hydrocarbon group that may contain a substituting group; and OR"$_{XIX}$ denotes a hydroxyl group that may be protected.

Compounds of Formula XIX are disclosed in WO 2002/059077, the entire disclosure of which is incorporated by reference.

In a preferred embodiment, the CETP inhibitor is selected from the following compounds of Formula XIX or their salts:

N-[(1RS,2SR)-2-(4-fluorophenyl)-2-hydroxy-1-[4-(trifluoromethyl)benzyl]ethyl]-6,7-dihydro-5H-benzo[a]cyclopentene-1-carboxamide, 4-fluoro-N-((1R,2S)-2-(4-fluorophenyl)-2-hydroxy-1-((4-(trifluoromethyl)phenyl)methyl)ethyl)-1-naphthalene carboxamide;

N-[(1R,2S)-2-(4-fluorophenyl)-2-hydroxy-1-[3-(1,1,2,2-tetrafluoroethoxy)benzyl]ethyl]-6,7-dihydro-5H-benzo[a]cyclopentene-1-carboxamide;

N-[(1RS,2SR)-2-(4-fluorophenyl)-2-hydroxy-1-[3-(1,1,2,2-tetrafluoroethoxy)benzyl]ethyl]-5,6-dihydronaphthalene-1-carboxamide;

N-[(1 RS,2SR)-2-(4-fluorophenyl)-2-hydroxy-1-[3-(1,1,2,2-tetrafluoroethoxy)benzyl]ethyl]-6,7,8,9-tetrahydro-5H-benzo[a]cycloheptene -1-carboxamide;

4-fluoro-N-[(1R,2S)-2-(4-fluorophenyl)-2-hydroxy-1-[3-(1,1,2,2-tetrafluoroethoxy)benzyl]ethyl]naphthalene-1-carboxamide;

N-[(1RS,2SR)-2-(4-fluorophenyl)-2-hydroxy-1-[3-(1,1,2,2-tetrafluoroethoxy)benzyl]ethyl]-5,6,7,8-tetrahydrobenzo[a]cyclooctene-1-carboxamide;

N-[(1RS,2SR)-2-(4-fluorophenyl)-2-hydroxy-1-(4-isopropylbenzyl)ethyl]-6,7-dihydro-5H-benzo[a]cycloheptene-1-carboxamide;

N-((1RS,2SR)-2-(3-fluorophenyl)-2-hydroxy-1-((4-(trifluoromethyl)phenyl)methyl)ethyl)-6,7-dihydro-5H-benzo[a]cycloheptene-1-carboxamide;

N-((1RS,2SR)-2-hydroxy-2-(4-phenoxyphenyl)-1-((4-(trifluoromethyl)phenyl)methyl)ethyl)-6,7-dihydro-5H-benzo[a]cycloheptene-1-carboxamide;

N-[(1RS,2SR)-2-(4-chlorophenyl)-2-hydroxy-1-[3-(1,1,2,2-tetrafluoroethoxy)benzyl]ethyl]-6,7-dihydro-5H-benzo[a]cycloheptene-1-carboxamide;

N-((1RS,2SR)-2-hydroxy-2-(4-phenyloxy)phenyl)-1-((3-((1,1,2,2-tetrafluoroethyl)oxy)phenyl)methyl)ethyl)-6,7-dihydro-5H-benzo[a]cyclohepte ne -1-carboxamide;

N-((1RS,2SR)-2-(4-((4-chloro-3-ethylphenyl)oxy)phenyl)-2-hydroxy-1-((3-((1,1,2,2-tetrafluoroethyl)oxy)phenyl)methyl)ethyl)-6,7-dihydro-5H-benzo[a]cycloheptene-1-carboxamide;

N-((1RS,2SR)-2-(2-fluoropyridine-4-yl)-2-hydroxy-1-((3-((1,1,2,2-tetrafluoroethoxy)phenyl)methyl)ethyl)-6,7-dihydro-5H-benzo[a]cycloheptene -1-carboxamide;

N-((1RS,2RS)-2-(6-fluoropyridine-2-yl)-2-hydroxy-1-((3-((1,1,2,2-tetrafluoroethoxy)phenyl)methyl)ethyl)-6,7-dihydro-5H-benzo[a]cycloheptene-1-carboxamide;

N-[(1RS,2SR)-1-(4-tert-butylbenzyl)-2-(3-chlorophenyl) -2-hydroxyethyl]-5-chloro-1-napthoamide;

4-fluoro-N-{(1RS,2SR)-2-(4-fluorophenyl)-2-hydroxy1-[(2,2,3,3-tetrafluoro-2,3-dihydro-1,4-benzodioxin-6-yl) methyl]ethyl}-1-naphthoamide.

In a preferred embodiment, the CETP inhibitor is [2R,4S]-4-[(3,5-bis-trifluoromethyl-benzyl)-methoxycarbonyl-amino]-2-ethyl-6-trifluoromethyl-3,4-dihydro -2H-quinoline-1-carboxylic acid ethyl ester also known as torcetrapib. Torcetrapib is shown by the following Formula

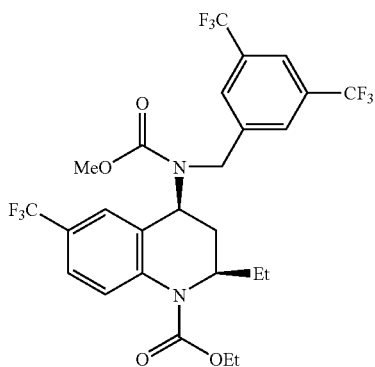

CETP inhibitors, in particular torcetrapib, and methods for preparing such compounds are disclosed in detail in U.S. Pat. Nos. 6,197,786 and 6,313,142, in PCT Application Nos. WO 01/40190A1, WO 02/088085A2, and WO 02/088069A2, the disclosures of which are herein incorporated by reference. Torcetrapib has an unusually low solubility in aqueous environments such as the lumenal fluid of the human GI tract. The aqueous solubility of torceptrapib is less than about 0.04 μg/ml. Torcetrapib must be presented to the GI tract in a solubility-enhanced form in order to achieve a sufficient drug concentration in the GI tract in order to achieve sufficient absorption into the blood to elicit the desired therapeutic effect.

Solid Amorphous Dispersions of CETP Inhibitors

The CETP inhibitor and concentration-enhancing polymer are combined and formed into a solid amorphous dispersion. By solid amorphous dispersion is meant a solid material in which at least a portion of the CETP inhibitor is in the amorphous form and dispersed in the polymer. Preferably, at least a major portion of the CETP inhibitor in the solid amorphous dispersion is amorphous. By "amorphous" is meant simply that the CETP inhibitor is in a non-crystalline state. As used herein, the term "a major portion" of the CETP inhibitor means that at least 60 wt % of the drug in the solid amorphous dispersion is in the amorphous form, rather than the crystalline form. Preferably, the CETP inhibitor in the solid amorphous dispersion is substantially amorphous. As used herein, "substantially amorphous" means that the amount of the CETP inhibitor in crystalline form does not exceed about 25 wt %. More preferably, the CETP inhibitor in the solid amorphous dispersion is "almost completely amorphous," meaning that the amount of CETP inhibitor in the crystalline form does not exceed about 10 wt %. Amounts of crystalline CETP inhibitor may be measured by Powder X-Ray Diffraction (PXRD), Scanning Electron Microscope (SEM) analysis, differential scanning calorimetry (DSC), or any other standard quantitative measurement.

The solid dispersions may contain from about 1 to about 80 wt % CETP inhibitor, depending on the dose of the CETP inhibitor and the effectiveness of the concentration-enhancing polymer. Enhancement of aqueous CETP inhibitor concentrations and relative bioavailability are typically best at low CETP inhibitor levels, typically less than about 25 to about 40 wt %. However, due to the practical limit of the dosage form size, higher CETP inhibitor levels may be preferred and in many cases perform well.

The amorphous CETP inhibitor can exist within the solid amorphous dispersion in relatively pure amorphous drug domains or regions, as a solid solution of drug homogeneously distributed throughout the polymer or any combination of these states or those states that lie intermediate between them. The solid amorphous dispersion is preferably substantially homogeneous so that the amorphous CETP inhibitor is dispersed as homogeneously as possible throughout the polymer. As used herein, "substantially homogeneous" means that the fraction of CETP inhibitor that is present in relatively pure amorphous drug domains or regions within the solid amorphous dispersion is relatively small, on the order of less than 20 wt %, and preferably less than 10 wt % of the total amount of drug. Solid amorphous dispersions that are substantially homogeneous generally are more physically stable and have improved concentration-enhancing properties and, in turn, improved bioavailability, relative to nonhomogeneous dispersions.

In cases where the CETP inhibitor and the polymer have glass transition temperatures sufficiently far apart (greater than about 20° C.), the fraction of drug that is present in relatively pure amorphous drug domains or regions within the solid amorphous dispersion can be determined by examining the glass transition temperature ($T_g$) of the solid amorphous dispersion. $T_g$ as used herein is the characteristic temperature where a glassy material, upon gradual heating, undergoes a relatively rapid (e.g., in 10 to 100 seconds) physical change from a glassy state to a rubbery state. The $T_g$ of an amorphous material such as a polymer, drug, or dispersion can be measured by several techniques, including by a dynamic mechanical analyzer (DMA), a dilatometer, a dielectric analyzer, and by DSC. The exact values measured by each technique can vary somewhat, but usually fall within 10 to 30° C. of each other. When the solid amorphous dispersion exhibits a single $T_g$, the amount of CETP inhibitor in pure amorphous drug domains or regions in the solid amorphous dispersion is generally has less than about 10 wt %, confirming that the solid amorphous dispersion is substantially homogeneous. This is in contrast to a simple physical mixture of pure amorphous drug particles and pure amorphous polymer particles which generally display two distinct $T_g$s, one being that of the drug and one that of the polymer. For a solid amorphous dispersion that exhibits two distinct $T_g$s, one in the proximity of the drug $T_g$ and one of the remaining drug/polymer dispersion, at least a portion of the drug is present in relatively pure amorphous domains. The amount of CETP inhibitor present in relatively pure amorphous drug domains or regions may be determined by first preparing calibration standards of substantially homogeneous dispersions to determine $T_g$ of the solid amorphous dispersion versus drug loading in the dispersion. From these calibration data and the $T_g$ of the drug/polymer dispersion, the fraction of CETP inhibitor in relatively pure amorphous drug domains or regions can be determined. Alternatively, the amount of CETP inhibitor present in relatively pure amorphous drug domains or regions may be determined by comparing the magnitude of the heat capacity for the transition in the proximity of the drug $T_g$ with calibration standards consisting essentially of a physical mixture of amorphous drug and polymer. In either case, a solid amorphous dispersion is considered to be substantially homogeneous if the fraction of CETP inhibitor that is present in relatively pure amorphous drug domains or regions within the solid amorphous dispersion is less than 20 wt %, and preferably less than 10 wt % of the total amount of CETP inhibitor.

Acidic Concentration-Enhancing Polymers

The solid amorphous dispersions of the present invention comprise a CETP inhibitor and an acidic concentration-enhancing polymer. The acidic concentration-enhancing polymers suitable for use in the solid amorphous dispersions should be inert, in the sense that they do not chemically react with the CETP inhibitor in an adverse manner. The polymer should have an aqueous solubility of at least 0.1 mg/mL over at least a portion of the pH range of 1-8.

By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a $pK_a$ of less than about 10. Here, the term $pK_a$ is used in its traditional form, the $pK_a$ being the negative logarithm of the acid ionization constant. The $pK_a$ will be influenced by such factors as solvent, temperature, water content, and ionic strength of the media or matrix in which the acid resides. Unless otherwise noted, the $pK_a$ is assumed to be measured in distilled water at 25° C. Since in general, the more acidic the polymer the more useful the invention, the invention is preferred for polymers with functional groups with $pK_a$s of less than about 7, and even more preferred with $pK_a$s of less than about 6. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents."

It is preferred that the concentration-enhancing polymer be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion-pairing or hydrogen bonds, with ionic or polar groups of the drug. In the case of ionizable polymers, the hydrophilic regions of the polymer would include the ionized functional groups. In addition, the repulsion of the like charges of the ionized groups of such polymers (where the polymer is ionizable) may serve to limit the size of the polymer/drug assemblies to the nanometer or submicron scale. Such drug/concentration-enhancing polymer assemblies in solution may well resemble charged polymeric micellar-like structures. In any case, regardless of the mechanism of action, the inventors have observed that such amphiphilic polymers, particularly ionizable cellulosic polymers such as those listed below, have been shown to interact with drug so as to maintain a higher concentration of drug in an aqueous use environment.

One class of acidic concentration-enhancing polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGIT® series manufactured by Rohm Tech Inc., of Maiden, Mass.; proteins such as gelatin and albumin; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGIT® series, which are copolymers of methacrylates and acrylates.

A preferred class of polymers comprises acidic ionizable cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate-substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulosic polymer has both hydrophilic and hydrophobic substituents. Hydrophobic substituents may be essentially any substituent that, if substituted to a high enough level or degree of substitution, can render the cellulosic polymer essentially aqueous-insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked non-ionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

A preferred class of acidic cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; phosphates, such as phosphate ethoxy; and sulfonates, such as sulphonate ethoxy. Exemplary ester-linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

The polymer may also contain neutral, or non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, ethyl carboxymethyl cellulose, carboxymethyl ethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary acidic cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic acidic polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of amphiphilic cellulosic acidic polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, hydroxyethyl cellulose acetate succinate and carboxymethyl ethyl cellulose.

Of these cellulosic polymers that are at least partially ionized at physiologically relevant pHs, the inventors have found the following to be most preferred: hydroxypropyl methyl cellulose acetate succinate, hydroxypropyl methyl cellulose phthalate, cellulose acetate phthalate, cellulose acetate trimellitate and carboxymethyl ethyl cellulose. The most preferred is hydroxypropyl methyl cellulose acetate succinate (HPMCAS).

While specific polymers have been discussed as being suitable for use in the dosage forms of the present invention, blends of such polymers may also be suitable. Thus, the term "concentration-enhancing polymer" is intended to include blends of polymers in addition to a single species of polymer.

The amount of concentration-enhancing polymer relative to the amount of CETP inhibitor present in the solid drug dispersions depends on the drug and concentration-enhancing polymer and may vary widely from a drug-to-polymer weight ratio of 0.01 to 5, or from about 1 to about 80 wt % drug. However, in most cases, except when the CETP inhibitor dose is quite low, e.g., 25 mg or less, it is preferred that the drug-to-polymer ratio is greater than 0.05 and less than 2.5 (from about 5 to about 70 wt % drug) and often the enhancement in drug concentration or relative bioavailability is observed at drug-to-polymer ratios of 1 (about 50 wt % drug) or less or for some drugs even 0.2 (about 17 wt % drug) or less. In cases where the drug dose is about 25 mg or less, the drug-to-polymer weight ratio may be significantly less than 0.05. In general, regardless of the dose, enhancements in drug concentration or relative bioavailability increase with decreasing drug-to-polymer weight ratio. However, due to the practical limits of keeping the total mass of a dosage form low, it is often desirable to use a relatively high drug-to-polymer ratio as long as satisfactory results are obtained. The maximum drug:polymer ratio that yields satisfactory results varies from drug to drug and is best determined in the in vitro and/or in vivo dissolution tests described below.

Concentration Enhancement

The polymer used in the solid amorphous dispersion is a "concentration-enhancing polymer," meaning that it meets at least one, and preferably both, of the following conditions. The first condition is that the concentration-enhancing polymer increases the maximum drug concentration (MDC) of the CETP inhibitor in the environment of use relative to a control composition consisting of an equivalent amount of the undispersed CETP inhibitor but no polymer. That is, once the composition is introduced into an environment of use, the polymer increases the aqueous concentration of CETP inhibitor relative to the control composition. It is to be understood that the control composition is free from solubilizers or other components that would materially affect the solubility of the CETP inhibitor, and that the CETP inhibitor is in solid form in the control composition. The control composition is conventionally the undispersed, or crystalline form, of the CETP inhibitor alone. Preferably, the polymer increases the MDC of the CETP inhibitor in aqueous solution by at least 1.25-fold relative to a control composition, more preferably by at least 2-fold, and most preferably by at least 3-fold. Surprisingly, the polymer may achieve extremely large enhancements in aqueous concentration. In some cases, the MDC of CETP inhibitor provided by the test composition is at least 10-fold, at least 50-fold, at least 200-fold, at least 500-fold, to more than 1000-fold the equilibrium concentration provided by the control.

The second condition is that the concentration-enhancing polymer increases the area under the concentration in the use environment versus time curve (AUC) of the CETP inhibitor in the environment of use relative to a control composition consisting of the undispersed CETP inhibitor but no polymer. (The calculation of an AUC is a well-known procedure in the pharmaceutical arts and is described, for example, in Welling, "Pharmacokinetics Processes and Mathematics," ACS Monograph 185 (1986).) More specifically, in the environment of use, the composition comprising the CETP inhibitor and the concentration-enhancing polymer provides an AUC in the use environment for any 90-minute period of from about 0 to about 270 minutes following introduction to the use environment that is at least 1.25-fold that of the control composition described above. Preferably, the AUC in the use environment provided by the composition is at least 2-fold, more preferably at least 3-fold that of the control composition. For some CETP inhibitors, the compositions of the present invention may provide an AUC value that is at least 5-fold, at least 25-fold, at least 100—fold, and even more than 250-fold that of a control composition as described above.

As previously mentioned, a "use environment" can be either the in vivo environment, such as the GI tract of an animal, particularly a human, or the in vitro environment of a test solution, such as phosphate buffered saline (PBS) solution or Model Fasted Duodenal (MFD) solution.

Concentration enhancement may be determined through either in vivo tests or through in vitro dissolution tests. A composition of the present invention meets the concentration enhancement criteria in at least one of the above test environments.

Where the use environment is the GI tract of an animal, dissolved drug concentration may be determined by a conventional method known in the art. One method is a deconvolution method. In this method, the serum or plasma drug concentration is plotted along the ordinate (y-axis) against the blood sample time along the abscissa (x-axis). The data may then be analyzed to determine drug release rates in the GI tract using any conventional analysis, such as the Wagner-Nelson or Loo-Riegelman analysis. See also Welling, "Pharmacokinetics: Processes and Mathematics" (ACS Monograph 185, Amer. Chem. Soc., Washington, D.C., 1986). Treatment of the data in this manner yields an apparent in vivo drug release profile. Another method is to intubate the patient and periodically sample the GI tract directly.

The solid amorphous dispersions of CETP inhibitor and concentration-enhancing polymer used in the inventive dosage forms provide enhanced concentration of the dissolved CETP inhibitor in vitro dissolution tests. It has been determined that enhanced drug concentration in vitro dissolution tests in MFD solution or in PBS solution is a good indicator of in vivo performance and bioavailability. An appropriate PBS solution is an aqueous solution comprising 20 mM $Na_2HPO_4$, 47 mM $KH_2PO_4$, 87 mM NaCl, and 0.2 mM KCl, adjusted to pH 6.5 with NaOH. An appropriate MFD solution is the same PBS solution wherein there is also present 7.3 mM sodium taurocholic acid and 1.4 mM of 1-palmitoyl-2-oleyl-sn-glycero-3-phosphocholine. In particular, a composition formed by the inventive method can be dissolution-tested by adding it to MFD or PBS solution and agitating to promote dissolution.

An in vitro test to evaluate enhanced CETP inhibitor concentration in aqueous solution can be conducted by (1) adding with agitation a sufficient quantity of control composition, typically the undispersed CETP inhibitor alone, to the in vitro test medium, such as an MFD or a PBS solution, to achieve equilibrium concentration of the CETP inhibitor; (2) in a separate vessel, adding with agitation a sufficient quantity of test composition (e.g., the solid amorphous dispersion of CETP inhibitor and polymer) in the same test medium, such that if all the CETP inhibitor dissolved, the theoretical concentration of CETP inhibitor would exceed the equilibrium concentration of the CETP inhibitor by a factor of at least 2, and preferably by a factor of at least 10; and (3) comparing the measured MDC and/or aqueous AUC of the test composition in the test medium with the equilibrium concentration, and/or with the aqueous AUC of the control composition. In conducting such a dissolution test, the amount of test composition or control composition used is an amount such that if all of the CETP inhibitor dissolved the CETP inhibitor concentration would be at least 2-fold, preferably at least 10-fold, and most preferably at least 100-fold that of the equilibrium concentration. Indeed, for some extremely insoluble CETP inhibitors, in order to identify the MDC achieved it may be necessary to use an amount of test composition such that if all of the CETP inhibitor dissolved, the CETP inhibitor concentration would be 1000-fold or even more, that of the equilibrium concentration of the CETP inhibitor.

The concentration of dissolved CETP inhibitor is typically measured as a function of time by sampling the test medium and plotting CETP inhibitor concentration in the test medium vs. time so that the MDC can be ascertained. The MDC is taken to be the maximum value of dissolved CETP inhibitor measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets the criterion of this invention, then the composition formed is considered to be within the scope of this invention.

To avoid large drug particulates that would give an erroneous determination, the test solution is either filtered or centrifuged. "Dissolved drug" is typically taken as that material that either passes a 0.45 µm syringe filter or, alternatively, the material that remains in the supernatant following centrifugation. Filtration can be conducted using a 13 mm, 0.45 µm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It should be recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

In another separate aspect, the solid amorphous dispersions, when dosed orally to a human or other animal in a fasted state, provides improved concentration of dissolved CETP inhibitor in the blood relative to the control composition. The solid amorphous dispersion achieves a higher maximum drug concentration ($C_{max}$) of the CETP inhibitor in the blood (serum or plasma) relative to a control composition consisting of an equivalent amount of crystalline drug in its lowest energy form, or amorphous form if the crystalline form is unknown. It is to be understood that the control composition is free from solubilizers or other components that would materially affect the solubility of the CETP inhibitor. Preferably, the solid amorphous dispersion provides a $C_{max}$ of CETP inhibitor in the blood that is at least 1.25-fold that provided by the control composition, more preferably by at least 2-fold, and most preferably by at least 3-fold.

Alternatively, the solid amorphous dispersions, when dosed orally to a human or other animal, provide an AUC in CETP inhibitor concentration in the blood that is at least about 1.25-fold, preferably at least about 2-fold, preferably at least about 3-fold, preferably at least about 4-fold, preferably at least about 6-fold, preferably at least 10-fold, and even more preferably at least about 20-fold that observed when a control composition consisting of an equivalent quantity of undispersed CETP inhibitor is dosed. It is noted that such compositions can also be said to have a relative bioavailability of from about 1.25-fold to about 20-fold that of the control composition.

Relative bioavailability of CETP inhibitors in the solid amorphous dispersions can be tested in vivo in animals or humans using conventional methods for making such a determination. An in vivo test, such as a crossover study, may be used to determine whether a composition of CETP inhibitor and concentration-enhancing polymer provides an enhanced relative bioavailability compared with a control composition as described above. In an in vivo crossover study a test composition of a solid amorphous dispersion of a CETP inhibitor and polymer is dosed to half a group of test subjects and, after an appropriate washout period (e.g., one week) the same subjects are dosed with a control composition that consists of an equivalent quantity of undispersed CETP inhibitor as the test composition (but with no polymer present). The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the drug solubility in vivo.

Preparation of Dispersions

The solid amorphous dispersions of CETP inhibitor and acidic concentration-enhancing polymer may be made according to any conventional process for forming solid amorphous dispersions that results in at least a major portion (at least 60%) of the CETP inhibitor being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray-coating and spray-drying. See, for example, the following U.S. patents, the pertinent disclosures of which are incorporated herein by reference: Nos. 5,456,923 and 5,939,099, which describe forming dispersions by extrusion processes; Nos. 5,340,591 and 4,673,564, which describe forming dispersions by milling processes; and Nos. 5,707,646 and 4,894,235, which describe forming dispersions by melt congeal processes.

When the CETP inhibitor has a relatively low melting point, typically less than about 200° C. and preferably less than about 150° C., the use of a melt-congeal or melt-extrusion process is advantageous. In such processes, a molten mixture comprising the CETP inhibitor and concentration-enhancing polymer is rapidly cooled to solidify the molten mixture to form a solid amorphous dispersion. By "molten mixture" is meant that the mixture comprising the CETP inhibitor and concentration-enhancing polymer is heated sufficiently that it becomes sufficiently fluid that the CETP inhibitor substantially disperses in one or more of the concentration-enhancing polymers and other excipients. Generally, this requires that the mixture be heated to about 10C or more above the melting point of the lowest melting excipient or CETP inhibitor in the composition. The CETP inhibitor may exist in the molten mixture as a pure phase, as a solution of CETP inhibitor homogeneously distributed throughout the molten mixture, or any combination of these states or those states that lie intermediate between them. The molten mixture is preferably substantially homogeneous so that the CETP inhibitor is dispersed as homogeneously as possible throughout the molten mixture. When the temperature of the molten mixture is below the melting point of both the CETP inhibitor and the concentration-enhancing polymer, the molten excipients, concentration-enhancing polymer, and CETP inhibitor are preferably sufficiently soluble in each other that a substantial portion of the CETP inhibitor disperses in the concentration-enhancing polymer or excipients. It is often preferred that the mixture be heated above the lower of the melting points of the concentration-enhancing polymer and the CETP inhibitor. It should be noted that many concentration-enhancing polymers are amorphous. In such cases, melting point refers to the softening point of the polymer. Thus, although the term "melting point" generally refers specifically to the temperature at which a crystalline material transitions from its crystalline to its liquid state, as used herein, the term is used more broadly, referring to the heating of any material or mixture of materials sufficiently that it becomes fluid in a manner similar to a crystalline material in the fluid state.

Generally, the processing temperature may vary from 50° C. up to about 200° C. or higher, depending on the melting point of the CETP inhibitor and polymer, the latter being a function of the polymer grade selected. However, the processing temperature should not be so high that an unacceptable level of degradation of the CETP inhibitor or polymer occurs. In some cases, the molten mixture should be formed under an inert atmosphere to prevent degradation of the CETP inhibitor and/or polymer at the processing temperature. When relatively high temperatures are used, it is often preferable to minimize the time that the mixture is at the elevated temperature to minimize degradation.

The molten mixture may also include an excipient that will reduce the melting temperature of the molten mixture, thereby allowing processing at a lower temperature. When such excipients have low volatility and substantially remain in the mixture upon solidification, they generally can comprise up to 30 wt % of the molten mixture. For example, a plasticizer may be added to the mixture to reduce the melting temperature of the polymer. Examples of plasticizers include water, triethylcitrate, triacetin, and dibutyl sebacate. Volatile agents that dissolve or swell the polymer, such as acetone, water, methanol and ethyl acetate, may also be added to reduce the melting point of the molten mixture. When such volatile excipients are added, at least a portion, up to essentially all of such excipients may evaporate in the process of or following conversion of the molten mixture to a solid mixture. In such cases, the processing may be considered to be a combination of solvent processing and melt-congealing or melt-extrusion. Removal of such volatile excipients from the molten mixture can be accomplished by breaking up or atomizing the molten mixture into small droplets and contacting the droplets with a fluid so that the droplets both cool and lose all or part of the volatile excipient. Examples of other excipients that can be added to the mixture to reduce the processing temperature include low molecular weight polymers or oligomers, such as polyethylene glycol, polyvinylpyrrolidone, and poloxamers; fats and oils, including mono-, di-, and triglycerides; natural and synthetic waxes, such as Carnauba wax, beeswax, microcrystalline wax, castor wax, and paraffin wax; long chain alcohols, such as cetyl alcohol and stearyl alcohol; and long chain fatty acids, such as stearic acid. As mentioned above, when the excipient added is volatile, it may be removed from the mixture while still molten or following solidification to form the solid amorphous dispersion.

Virtually any process may be used to form the molten mixture. One method involves melting the concentration-enhancing polymer in a vessel and then adding the CETP inhibitor to the molten polymer. Another method involves melting the CETP inhibitor in a vessel and then adding the concentration-enhancing polymer. In yet another method, a solid blend of the CETP inhibitor and concentration-enhancing polymer may be added to a vessel and the blend heated to form the molten mixture.

Once the molten mixture is formed, it may be mixed to ensure the CETP inhibitor is homogeneously distributed throughout the molten mixture. Such mixing may be done using mechanical means, such as overhead mixers, magnetically driven mixers and stir bars, planetary mixers, and homogenizers. Optionally, when the molten mixture is formed in a vessel, the contents of the vessel can be pumped out of the vessel and through an in-line or static mixer and then returned to the vessel. The amount of shear used to mix the molten mixture should be sufficiently high to ensure uniform distribution of the CETP inhibitor in the molten mixture. The molten mixture can be mixed from a few minutes to several hours, the mixing time depending on the viscosity of the mixture and the solubility of the CETP inhibitor and the presence of optional excipients in the concentration-enhancing polymer.

Yet another method of preparing the molten mixture is to use two vessels, melting the CETP inhibitor in the first vessel and the concentration-enhancing polymer in a second vessel. The two melts are then pumped through an in-line static mixer or extruder to produce the molten mixture that is then rapidly solidified.

Still another method of preparing the molten mixture is by the use of an extruder, such as a single-screw or twin-screw extruder, both well known in the art. In such devices, a solid feed of the composition is fed to the extruder, whereby the combination of heat and shear forces produce a uniformly mixed molten mixture, which can then be rapidly solidified to form the solid amorphous dispersion. The solid feed can be prepared using methods well known in the art for obtaining solid mixtures with high content uniformity. Alternatively, the extruder may be equipped with two feeders, allowing the CETP inhibitor to be fed to the extruder through one feeder and the polymer through the other. Other excipients to reduce the processing temperature as described above may be included in the solid feed, or in the case of liquid excipients, such as water, may be injected into the extruder using methods well known in the art.

The extruder should be designed so that it produces a molten mixture with the CETP inhibitor uniformly distributed throughout the composition. Various zones in the extruder should be heated to appropriate temperatures to obtain the desired extrudate temperature as well as the desired degree of mixing or shear, using procedures well known in the art.

When the CETP inhibitor has a high solubility in the concentration-enhancing polymer, a lower amount of mechanical energy will be required to form the solid amorphous dispersion. In the case where the melting point of the undispersed CETP inhibitor is greater than the melting point of the undispersed concentration-enhancing polymer, the processing temperature may be below the melting temperature of the undispersed CETP inhibitor but greater than the melting point of the polymer, since the CETP inhibitor will dissolve into the molten polymer. When the melting point of the undispersed CETP inhibitor is less than the melting point of the undispersed concentration-enhancing polymer, the processing temperature may be above the melting point of the undispersed CETP inhibitor but below the melting point of the undispersed concentration-enhancing polymer since the molten CETP inhibitor will dissolve in or be absorbed into the polymer.

When the CETP inhibitor has a low solubility in the polymer, a higher amount of mechanical energy may be required to form the solid amorphous dispersion. Here, the processing temperature may need to be above the melting point of the CETP inhibitor and the polymer. As mentioned above, alternatively, a liquid or low-melting point excipient may be added that promotes melting or the mutual solubility of the concentration-enhancing polymer and a CETP inhibitor. A high amount of mechanical energy may also be needed to mix the CETP inhibitor and the polymer to form a dispersion. Typically, the lowest processing temperature and an extruder design that imparts the lowest amount of mechanical energy, i.e., shear, that produces a satisfactory dispersion (substantially amorphous and substantially homogeneous) is chosen in order to minimize the exposure of the CETP inhibitor to harsh conditions.

Once the molten mixture of CETP inhibitor and concentration-enhancing polymer is formed, the mixture should be rapidly solidified to form the solid amorphous dispersion. By "rapidly solidified" is meant that the molten mixture is solidified sufficiently fast that substantial phase separation of the CETP inhibitor and polymer does not occur. Typically, this means that the mixture should be solidified in less than about 10 minutes, preferably less than about 5 minutes and more preferably less than about 1 minute. If the mixture is not rapidly solidified, phase separation can occur, resulting in the formation of CETP inhibitor-rich and polymer-rich phases.

Solidification often takes place primarily by cooling the molten mixture to at least about 100 and preferably at least about 30° C. below it's melting point. As mentioned above, solidification can be additionally promoted by evaporation of all or part of one or more volatile excipients or solvents. To promote rapid cooling and evaporation of volatile excipients, the molten mixture is often formed into a high surface area shape such as a rod or fiber or droplets. For example, the molten mixture can be forced through one or more small holes to form long thin fibers or rods or may be fed to a device, such as an atomizer such as a rotating disk, that breaks the molten mixture up into droplets from 1 µm to 1 cm in diameter. The droplets are then contacted with a relatively cool fluid such as air or nitrogen to promote cooling and evaporation.

A useful tool for evaluating and selecting conditions for forming substantially homogeneous, substantially amorphous dispersions via a melt-congeal or melt-extrusion process is the differential scanning calorimeter (DSC). While the rate at which samples can be heated and cooled in a DSC is limited, it does allow for precise control of the thermal history of a sample. For example, the CETP inhibitor and concentration-enhancing polymer may be dry-blended and then placed into the DSC sample pan. The DSC can then be programmed to heat the sample at the desired rate, hold the sample at the desired temperature for a desired time, and then rapidly cool the sample to ambient or lower temperature. The sample can then be re-analyzed on the DSC to verify that it was transformed into a substantially homogeneous, substantially amorphous dispersion (i.e., the sample has a single Tg). Using this procedure, the temperature and time required to achieve a substantially homogeneous, substantially amorphous dispersion for a given CETP inhibitor and concentration-enhancing polymer can be determined.

Another method for forming solid amorphous dispersions is by "solvent processing," which consists of dissolution of the CETP inhibitor and one or more polymers in a common solvent. "Common" here means that the solvent, which can be a mixture of compounds, will dissolve both the CETP inhibitor and the polymer(s). After both the CETP inhibitor and the polymer have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and CETP inhibitor solution with $CO_2$, water, or some other non-solvent. Preferably, removal of the solvent results in the formation of a substantially homogeneous, solid amorphous dispersion. In such dispersions, the CETP inhibitor is dispersed as homogeneously as possible throughout the polymer and can be thought of as a solid solution of CETP inhibitor dispersed in the polymer(s), wherein the solid amorphous dispersion is thermodynamically stable, meaning that the concentration of CETP inhibitor in the polymer is at or below its equilibrium value, or it may be considered to be a supersaturated solid solution where the CETP inhibitor concentration in the concentration-enhancing polymer(s) is above its equilibrium value.

The solvent may be removed by spray-drying. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's *Chemical Engineers'* Handbook, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, at least a portion of the heat required for evaporation of solvent may be provided by heating the spray solution.

Solvents suitable for spray-drying can be any organic compound in which the CETP inhibitor and polymer are mutually soluble. Preferably, the solvent is also volatile with a boiling point of 150° C. or less. In addition, the solvent should have relatively low toxicity and be removed from the solid amorphous dispersion to a level that is acceptable according to The International Committee on Harmonization (ICH) guidelines. Removal of solvent to this level may require a subsequent processing step such as tray-drying. Preferred solvents include alcohols such as methanol, ethanol, n-propanol, isopropanol, and butanol; ketones such as acetone, methyl ethyl ketone and methyl iso-butyl ketone; esters such as ethyl acetate and propylacetate; and various other solvents such as acetonitrile, methylene chloride, toluene, tetrahydrofuran, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water, so long as the polymer and CETP inhibitor are sufficiently soluble to make the spray-drying process practicable. Generally, due to the hydrophobic nature of low-solubility CETP inhibitors, non-aqueous solvents are preferred, meaning that the solvent comprises less than about 10 wt % water.

The solvent-bearing feed, comprising the CETP inhibitor and the concentration-enhancing polymer, can be spray-dried under a wide variety of conditions and yet still yield dispersions with acceptable properties. For example, various types of nozzles can be used to atomize the spray solution, thereby introducing the spray solution into the spray-dry chamber as a collection of small droplets. Essentially any type of nozzle may be used to spray the solution as long as the droplets that are formed are sufficiently small that they dry sufficiently (due to evaporation of solvent) that they do not stick to or coat the spray-drying chamber wall.

Although the maximum droplet size varies widely as a function of the size, shape and flow pattern within the spray-dryer, generally droplets should be less than about 500 μm in diameter when they exit the nozzle. Examples of types of nozzles that may be used to form the solid amorpohous dispersions include the two-fluid nozzle, the fountain-type nozzle, the flat fan-type nozzle, the pressure nozzle and the rotary atomizer. In a preferred embodiment, a pressure nozzle is used, as disclosed in detail in commonly assigned copending U.S. Provisional Application No. 60/353,986, the disclosure of which is incorporated herein by reference.

The spray solution can be delivered to the spray nozzle or nozzles at a wide range of temperatures and flow rates. Generally, the spray solution temperature can range anywhere from just above the solvent's freezing point to about 20° C. above its ambient pressure boiling point (by pressurizing the solution) and in some cases even higher. Spray solution flow rates to the spray nozzle can vary over a wide range depending on the type of nozzle, spray-dryer size and spray-dry conditions such as the inlet temperature and flow rate of the drying gas. Generally, the energy for evaporation of solvent from the spray solution in a spray-drying process comes primarily from the drying gas.

The drying gas can, in principle, be essentially any gas, but for safety reasons and to minimize undesirable oxidation of the CETP inhibitor or other materials in the solid amorphous dispersion, an inert gas such as nitrogen, nitrogen-enriched air or argon is utilized. The drying gas is typically introduced into the drying chamber at a temperature between about 60° and about 300° C. and preferably between about 80° and about 240° C.

The large surface-to-volume ratio of the droplets and the large driving force for evaporation of solvent leads to rapid solidification times for the droplets. Solidification times should be less than about 20 seconds, preferably less than about 10 seconds, and more preferably less than 1 second. This rapid solidification is often critical to the particles maintaining a uniform, homogeneous dispersion instead of separating into CETP inhibitor-rich and polymer-rich phases. In a preferred embodiment, the height and volume of the spray-dryer are adjusted to provide sufficient time for the droplets to dry prior to impinging on an internal surface of the spray-dryer, as described in detail in commonly assigned, copending U.S. Provisional Application No. 60/354,080, now published U.S. Patent Application 20030163931, incorporated herein by reference. As noted above, to get large enhancements in concentration and bioavailability it is often necessary to obtain as homogeneous a dispersion as possible.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of the CETP inhibitor molecules in the solid amorphous dispersion, thereby improving its stability. Generally, the solvent content of the solid amorphous dispersion as it leaves the spray-drying chamber should be less than 10 wt % and preferably less than 2 wt %. Following formation, the solid amorphous dispersion can be dried to remove residual solvent using suitable drying processes, such as tray drying, fluid bed drying, microwave drying, belt drying, rotary drying, and other drying processes known in the art.

The solid amorphous dispersion is usually in the form of small particles. The mean size of the particles may be less than 500 μm in diameter, or less than 100 μm in diameter, less than 50 μm in diameter or less than 25 μm in diameter. When the solid amorphous dispersion is formed by spray-drying, the resulting dispersion is in the form of such small particles. When the solid amorphous dispersion is formed by other methods such by melt-congeal or extrusion processes, the resulting dispersion may be sieved, ground, or otherwise processed to yield a plurality of small particles.

Once the solid amorphous dispersion comprising the CETP inhibitor and concentration-enhancing polymer has been formed, several processing operations can be used to facilitate incorporation of the dispersion into a dosage form. These processing operations include drying, granulation, and milling.

The solid amorphous dispersion may be granulated to increase particle size and improve handling of the dispersion while forming a suitable dosage form. Preferably, the average size of the granules will range from 50 to 1000 μm. Such granulation processes may be performed before or after the composition is dried, as described above. Dry or wet granulation processes can be used for this purpose. An example of a dry granulation process is roller compaction. Wet granulation processes can include so-called low shear and high shear granulation, as well as fluid bed granulation. In these processes, a granulation fluid is mixed with the composition after the dry components have been blended to aid in the formation of the granulated composition. Examples of granulation fluids include water, ethanol, isopropyl alcohol, n-propanol, the various isomers of butanol, and mixtures thereof.

If a wet granulation process is used, the granulated composition is often dried prior to further processing. Examples of suitable drying processes to be used in connection with wet granulation are the same as those described above. Where the solid amorphous dispersion is made by a solvent process, the composition can be granulated prior to removal of residual solvent. During the drying process, residual solvent and granulation fluid are concurrently removed from the composition.

Once the composition has been granulated, it may then be milled to achieve the desired particle size. Examples of suitable processes for milling the composition include hammer milling, ball milling, fluid-energy milling, roller milling, cutting milling, and other milling processes known in the art.

Processes for forming solid amorphous dispersions of CETP inhibitors and concentration-enhancing polymers are described in detail in commonly assigned, copending U.S. patent application Ser. Nos. 09/918,127 and 10/066,091, incorporated herein by reference.

HMG-CoA Reductase Inhibitors

The HMG-CoA reductase inhibitor may be any HMG-CoA reductase inhibitor capable of lower plasma concentrations of low-density lipoprotein, total cholesterol, or both. The HMG-CoA reductase inhibitor is acid-sensitive, meaning that the drug either chemically reacts with or otherwise degrades in the presence of acidic species. Examples of chemical reactions include hydrolysis, lactonization, or transesterification in the presence of acidic species.

In one aspect, the HMG-CoA reductase inhibitor is from a class of therapeutics commonly called statins. Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,450,171, 4,820,850; 4,916, 239), pravastatin (PRAVACHOL®; see U.S. Pat. Nos. 4,346, 227; 4,537,859; 4,410,629; 5,030,447 and 5,180,589), lactones of pravastatin (see U.S. Pat. No. 4,448,979), fluvastatin (LESCOL®; see U.S. Pat. Nos. 5,354,772; 4,911,165; 4,739, 073; 4,929,437; 5,189,164; 5,118,853; 5,290,946; 5,356,896), lactones of fluvastatin, atorvastatin (LIPITOR®; see U.S. Pat. Nos. 5,273,995; 4,681,893; 5,489,691; 5,342, 952), lactones of atorvastatin, cerivastatin (also known as rivastatin and BAYCHOL®; see U.S. Pat. No. 5,177,080, and European Application No. EP-491226A), lactones of cerivastatin, rosuvastatin (Crestor®; see U.S. Pat. Nos. 5,260,440 and RE37314, and European Patent No. EP521471), lactones of rosuvastatin, itavastatin, nisvastatin, visastatin, atavastatin, bervastatin, compactin, dihydrocompactin, dalvastatin, fluindostatin, pitivastatin, mevastatin (see U.S. Pat. No. 3,983, 140), and velostatin (also referred to as synvinolin). Other examples of HMG-CoA reductase inhibitors are described in U.S. Pat. Nos. 5,217,992; 5,196,440; 5,189,180; 5,166,364; 5,157,134; 5,110,940; 5,106,992; 5,099,035; 5,081,136; 5,049,696; 5,049,577; 5,025,017; 5,011,947; 5,010,105; 4,970,221; 4,940,800; 4,866,058; 4,686,237; 4,647,576; European Application Nos. 0142146A2 and 0221025A1; and PCT Application Nos. WO 86/03488 and WO 86/07054. Also included are pharmaceutically acceptable forms of the above. All of the above references are incorporated herein by reference. Preferably the HMG-CoA reductase inhibitor is selected from the group consisting of fluvastatin, lovastatin, pravastatin, atorvastatin, simvastatin, cerivastatin, rivastatin, mevastatin, velostatin, compactin, dalvastatin, fluindostatin, rosuvastatin, pitivastatin, dihydrocompactin, and pharmaceutically acceptable forms thereof. By "pharmaceutically acceptable forms" is meant any pharmaceutically acceptable derivative or variation, including stereoisomers, stereoisomer mixtures, enantiomers, solvates, hydrates, isomorphs, polymorphs, salt forms and prodrugs.

A test to determine whether an HMG-CoA reductase inhibitor is acid sensitive is to administer the drug to an acidic aqueous solution and plot drug concentration versus time. The acidic solution should have a pH of from 1-4. HMG-CoA reductase inhibitors that are acid sensitive are those for which the drug concentration decreases by at least 1% within 24 hours of administration of the drug to the acidic solution. If the drug concentration changes by 1% in the 6-24 hour time period, then the drug is "slightly acid-sensitive." If the drug concentration changes by 1% in the 1-6 hour time period, then the drug is "moderately acid-sensitive." If the drug concentration changes by 1% in less than 1 hour, then the drug is "highly acid-sensitive." The present invention finds increasing utility for HMG-CoA reductase inhibitors that are slightly acid-sensitive, moderately acid-sensitive and highly acid-sensitive.

In one embodiment, the HMG-CoA reductase inhibitor is selected from the group consisting of trans-6-[2-(3 or 4-carboxamido-substituted pyrrol-1-yl)alkyl]-4-hydroxypyran-2-ones and corresponding pyran ring-opened hydroxy acids derived therefrom. These compounds have been described in U.S. Pat. No. 4,681,893, which is herewith incorporated by reference in the present specification. The pyran ring-opened hydroxy acids which are intermediates in the synthesis of the lactone compounds can be used as free acids or as pharmaceutically acceptable metal or amine salts. In particular, these compounds can be represented by the following structure:

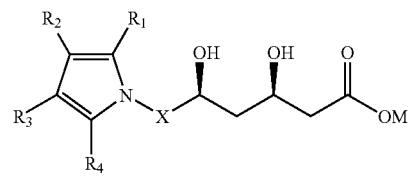

wherein X is —CH$_2$—, —CH$_2$CH$_2$—, —CH$_2$CH$_2$CH$_2$— or —CH$_2$CH(CH$_3$)—;

R$_1$ is 1-naphthyl; 2-naphthyl; cyclohexyl, norbornenyl; 2-,3-, or 4-pyridinyl; phenyl; phenyl substituted with fluorine, chlorine, bromine, hydroxyl, trifluoromethyl, alkyl of from one to four carbon atoms, alkoxy of from one to four carbon atoms, or alkanoylalkoxy of from two to eight carbon atoms; either R$_2$ or R$_3$ is —CONR$_5$R$_6$ where R$_5$ and R$_6$ are independently hydrogen; alkyl of from one to six carbon atoms; 2-,3-, or 4-pyridinyl; phenyl; phenyl substituted with fluorine, chlorine, bromine, cyano, trifluoromethyl, or carboalkoxy of from three to eight carbon atoms; and the other of R$_2$ or R$_3$ is hydrogen; alkyl of from one to six carbon atoms; cyclopropyl; cyclobutyl; cyclopentyl; cyclohexyl; phenyl; or phenyl substituted with fluorine, chlorine, bromine, hydroxyl, trifluoromethyl, alkyl of from one to four carbon atoms, alkoxy of from one to four carbon atoms, or alkanoyloxy of from two to eight carbon atoms; R$_4$ is alkyl of from one to six carbon atoms; cyclopropyl; cyclobutyl; cyclopentyl; cyclohexyl; or trifluoromethyl; and M is a pharmaceutically acceptable salt (e.g., counter ion), which includes a pharmaceutically acceptable metal salt or a pharmaceutically acceptable amine salt.

Among the stereo-specific isomers, one preferred HMG-CoA reductase inhibitor is atorvastatin trihydrate hemi-calcium salt. This preferred compound is the ring-opened form of (2R-trans)-5-(4-fluorophenyl)-2-(1 methylethyl)—N,4-diphenyl-1-[2-(tetrahydro-4-hydroxy-6-oxo-2H-pyran -2-yl) ethyl]-1H-pyrrole-3-carboxamide, namely, the enantiomer [R-(R*,R*)]-2-(4-fluorophenyl-β, δ-dihydroxy-5-(1-methylethyl)-3-phenyl-4-[(phenylamino)carbonyl)]-1H-pyrrole -1-heptanoic acid hemicalcium salt. Its chemical structure may be represented by the following structure:

Formula A

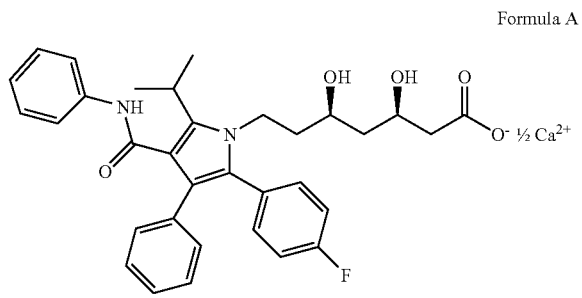

The specific isomer has been described in U.S. Pat. No. 5,273, 995, herein incorporated by reference. In a preferred embodiment, the HMG-CoA reductase inhibitor is selected from the group consisting of atorvastatin, the cyclized lactone form of atorvastatin, a 2-hydroxy, 3-hydroxy or 4-hydroxy derivative of such compounds, and pharmaceutically acceptable forms thereof.

In practice, use of the salt form amounts to use of the acid or lactone form. Appropriate pharmaceutically acceptable salts within the scope of the invention are those derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine and the like. Preferably, the lithium, calcium, magnesium, aluminum and ferrous or ferric salts are prepared from the sodium or potassium salt by adding the appropriate reagent to a solution of the sodium or potassium salt, i.e., addition of calcium chloride to a solution of the sodium or potassium salt of the compound of the formula A will give the calcium salt thereof.

Preparation of Unitary Dosage Forms

The unitary dosage form is formed by combining a CETP inhibitor composition with an HMG-CoA reductase inhibitor composition such that the solid amorphous dispersion and the HMG-CoA reductase inhibitor are substantially separate from one another in the dosage form. As described above, by substantially separate is meant that a sufficient amount of the HMG-CoA reductase inhibitor is physically separated from the solid amorphous dispersion so that the acidic concentration-enhancing polymer does not cause an unacceptable level of chemical degradation of the HMG-CoA reductase inhibitor. This improved chemical stability of the HMG-CoA reductase inhibitor is believed to be related primarily to reducing the fraction of HMG-CoA reductase inhibitor molecules that are in contact with the CETP inhibitor/acidic concentration-enhancing polymer solid amorphous dispersion.

For some unitary dosage forms, the separation is macroscopic in nature; that is, the HMG-CoA reductase inhibitor and the solid amorphous dispersion are physically separated. This may be accomplished by, for example, placing the HMG-CoA reductase inhibitor and the solid amorphous dispersion in separate layers of the dosage form so that only those HMG-CoA reductase inhibitor molecules present at the interface of the two layers may be in contact with the solid amorphous dispersion. Further separation between the HMG-CoA reductase inhibitor and the solid amorphous dispersion may be obtained by providing a third layer that separates the two compositions. Alternatively, the unitary dosage form may be in the form of a kit wherein the HMG-CoA reductase inhibitor and solid amorphous dispersion are within separate compartments in the dosage form. Further details of unitary dosage forms where the separation is macroscopic in nature are described below.

For other unitary dosage forms, the separation is microscopic in nature; that is, the separation may be due to only one or more intervening molecules. This is the case when the dosage form comprises a mixture of particles or granules. For example, the unitary dosage form may comprise the solid amorphous dispersion of the CETP inhibitor and a plurality of relatively large particles or granules comprising the HMG-CoA reductase inhibitor. The HMG-CoA reductase inhibitor molecules located in the interior of the particles or granules are separated from the solid amorphous dispersion of the CETP inhibitor by those molecules on the surface of the particles or granules. Furthermore, inclusion of excipients in the particles or granules containing the HMG-CoA reductase inhibitor will reduce the number of molecules of HMG-CoA reductase inhibitor on the surface of the particles or granules, resulting in further separation of the HMG-CoA reductase inhibitor from the solid amorphous dispersion.

Alternatively, the solid amorphous dispersion of CETP inhibitor may be in the form of relatively large particles or granules, with molecules of the acidic concentration-enhancing polymer in the solid amorphous dispersion on the interior of the particles of granules being separated from the HMG-CoA reductase inhibitor by those molecules on the surface of the particles or granules. Inclusion of granulation excipients in the particles or granules further reduces the fraction of solid amorphous dispersion on the surface of the particles or granules.

Alternatively, particles or granules of the HMG-CoA reductase inhibitor, particles or granules of the solid amorphous dispersion, or both may be coated with a protective coating, thus separating the HMG-CoA reductase inhibitor and the solid amorphous dispersion. In any case, the HMG-CoA reductase inhibitor and the solid amorphous dispersion are substantially separated from one another so that the acidic concentration-enhancing polymer does not cause an unacceptable level of chemical degradation of the HMG-CoA reductase inhibitor.

The amount of CETP inhibitor and HMG-CoA reductase inhibitor present in the dosage form will vary depending on the desired dose for each compound, which in turn, depends on the potency of the compound and the condition being treated. For example, the desired dose for the CETP inhibitor torcetrapib, also known as [2R,4S]-4-[(3,5-bis-trifluoromethyl-benzyl) -methdxycarbonyl-amino]-2-ethyl-6-trifluoromethyl-3,4-dihydro-2H-quinoline-1-carboxylic acid ethyl ester, ranges from 1 mg/day to 1000 mg/day, preferably 10 to 250 mg/day, more preferably 30 to 90 mg/day. For the HMG-CoA reductase inhibitor atorvastatin calcium, the dose ranges from 1 to 160 mg/day, preferably 2 to 80 mg/day. For the HMG-CoA reductase inhibitors lovastatin, pravastatin sodium, simvastatin, rosuvastatin calcium, and fluvastatin sodium, the dose ranges from 2 to 160 mg/day, preferably 10 to 80 mg/day. For the HMG-CoA reductase inhibitor cerivastatin sodium, the dose ranges from 0.05 to 1.2 mg/day, preferably 0.1 to 1.0 mg/day.

The CETP inhibitor composition comprises the solid amorphous dispersion and optional excipients, depending on the type of dosage form being prepared. The amount of solid amorphous dispersion present in the CETP inhibitor composition may vary according to the desired dose of CETP inhibitor. In one aspect, the CETP inhibitor composition has a high loading of the solid amorphous dispersion. High loadings of dispersion in the composition minimize the size of the dosage form, making the dosage form easier to swallow and improving patient compliance. Depending on the CETP inhibitor dose, the solid amorphous dispersion may comprise at least 30 wt % of the CETP inhibitor composition. More preferably, the solid amorphous dispersion comprises at least 40 wt %, and most preferably at least 50 wt % of the CETP inhibitor composition.

In addition to the solid amorphous dispersion, the CETP inhibitor composition may also comprise a disintegrant. The inclusion of a disintegrant into the CETP inhibitor composition promotes rapid dissolution of the dosage form when introduced into an aqueous use environment. Examples of disintegrants include sodium starch glycolate, sodium carboxymethyl cellulose, calcium carboxymethyl cellulose, croscarmellose sodium, crospovidone, polyvinylpolypyrrolidone, methyl cellulose, microcrystalline cellulose, powdered cellulose, lower alkyl-substituted hydroxypropyl cellulose, polacrilin potassium, starch, pregelatinized starch, sodium alginate, and mixtures thereof. Of these, crospovidone, croscarmellose sodium, lower alkyl-substituted hydroxypropyl cellulose, methyl cellulose, polacrilin potassium, and mixtures thereof are preferred, with crospovidone and croscarmellose sodium being most preferred. The amount of disintegrant included in the dosage form will depend on several factors, including the properties of the solid amorphous dispersion, other excipients present in the composition, and the desired rate of release of CETP inhibitor from the dosage form. Generally, the disintegrant will comprise from 1 wt % to 25 wt %, preferably from 5 wt % to 20 wt % of the CETP inhibitor composition.

The CETP inhibitor composition may also include a porosigen. A "porosigen" is a material that, when present in the formulation containing the solid amorphous dispersion, leads to a high porosity and high strength following compression of the blend into a tablet. In addition, preferred porosigens are soluble in an acidic environment with aqueous solubilities typically greater than 1 mg/mL at a pH less than about 4. Generally, the predominant deformation mechanism for porosigens under compression is brittle fracture rather than plastic flow. Examples of porosigens include acacia, calcium carbonate, calcium sulfate, calcium sulfate dihydrate, compressible sugar, dibasic calcium phosphate (anhydrous and dihydrate), tribasic calcium phosphate, monobasic sodium phosphate, dibasic sodium phosphate, lactose, magnesium oxide, magnesium carbonate, silicon dioxide, magnesium aluminum silicate, maltodextrin, mannitol, methyl cellulose, microcrystalline cellulose, sorbitol, sucrose and xylitol. Of these, microcrystalline cellulose and both forms of dibasic calcium phosphate (anhydrous and dihydrate) are preferred. As with the disintegrant selection, the amount of porosigen included in the dosage form will depend on the properties of the solid amorphous dispersion, the disintegrant and the porosigen selected. Generally, the porosigen will comprise from 5 to 70 wt %, and preferably from 10 to 50 wt % of the dosage form.

Other conventional formulation excipients may be employed in the CETP inhibitor composition, including those excipients well known in the art, e.g., as described in *Remington's Pharmaceutical Sciences* (18th ed. 1990). Generally, excipients such as surfactants, pH modifiers, fillers, matrix materials, complexing agents, solubilizers, pigments, lubricants, glidants, flavorants, and so forth may be used for customary purposes and in typical amounts without adversely affecting the properties of the compositions.

One very useful class of excipients is surfactants, preferably present from 0 to 10 wt %. Suitable surfactants include fatty acid and alkyl sulfonates; commercial surfactants such as benzalkonium chloride (HYAMINE® 1622 from Lonza, Inc. of Fairlawn, N.J.); dioctyl sodium sulfosuccinate (DOCUSATE SODIUM from Mallinckrodt Specialty Chemicals of St. Louis, Mo.); polyoxyethylene sorbitan fatty acid esters (TWEENO® from ICI Americas Inc. of Wilmington, Del.; LIPOSORB® 0-20 from Lipochem Inc. of Patterson N.J.; CAPMUL® POE-0 from Abitec Corp. of Janesville, Wis.); natural surfactants such as sodium taurocholic acid, 1-palmitoyl-2-oleoyl-sn-glycero-3-phosphocholine, lecithin, and other phospholipids and mono- and diglycerides; and polyoxyethylene-polyoxypropylene. Such materials can advantageously be employed to increase the rate of dissolution by, for example, facilitating wetting, or otherwise increase the rate of CETP inhibitor release from the dosage form.

Inclusion of pH modifiers such as acids, bases, or buffers may also be beneficial in an amount of from 0 to 10 wt %. Acidic pH modifiers (e.g., acids such as citric acid or succinic acid) retard the dissolution of the solid amorphous dispersion comprising the CETP inhibitor and acidic concentration-enhancing polymer.

In a preferred embodiment, the CETP inhibitor composition also includes a base. The inclusion of a base can locally raise the pH in the vicinity of the acidic concentration-enhancing polymer, leading to an improvement in chemical stability of the HMG-CoA reductase inhibitor. The term "base" is used broadly to include not only strong bases such as sodium hydroxide, but also weak bases and buffers that are capable of achieving the desired increase chemical stability. Examples of bases include hydroxides, such as sodium hydroxide, calcium hydroxide, ammonium hydroxide, and choline hydroxide; bicarbonates, such as sodium bicarbonate, potassium bicarbonate, and ammonium bicarbonate; carbonates, such as ammonium carbonate, calcium carbonate, and sodium carbonate; amines, such as tris(hydroxymethyl) amino methane, ethanolamine, diethanolamine, N-methyl glucamine, glucosamine, ethylenediamine, N,N'-dibenzyl-ethylenediamine, N-benzyl-2-phenethylamine, cyclohexylamine, cyclopentylamine, diethylamine, isopropylamine, diisopropylamine, dodecylamine, and triethylamine; proteins, such as gelatin; amino acids such as lysine, arginine, guanine, glycine, and adenine; polymeric amines, such as polyamino methacrylates, such as Eudragit E; conjugate bases of various acids, such as sodium acetate, sodium benzoate, ammonium acetate, disodium phosphate, trisodium phosphate, calcium hydrogen phosphate, sodium phenolate, sodium sulfate, ammonium chloride, and ammonium sulfate; salts of EDTA, such as tetra sodium EDTA; and salts of various acidic polymers such as sodium starch glycolate, sodium carboxymethyl cellulose and sodium polyacrylic acid. In one embodiment, the base partially neutralizes the acidic concentration-enhancing polymer. By "partially neutralizes" is meant that the base causes at least a portion of the acidic moieties or acidic substituents on the acidic concentration-enhancing polymer to exist in their deprotonated form. Such neutralized acidic polymers are described in more detail in copending, commonly assigned Provisional Patent Application entitled "Dosage Forms Comprising a CETP Inhibitor and an HMG-CoA Reductase Inhibitor" U.S. provisional patent application No. 60/435,298 filed Dec. 20, 2002, the disclosure of which is herein incorporated by reference. In a preferred embodiment, the base is present in an amount that is in molar excess relative to the acidic substituents on the dispersion polymer.

Examples of other matrix materials, fillers, or diluents include dextrose, compressible sugar, hydrous lactose, corn starch, silicic anhydride, polysaccharides, dextrates, dextran, dextrin, dextrose, calcium carbonate, calcium sulfate, poloxamers, and polyethylene oxide.

Another optional excipient is a binder such as methyl cellulose, carboxy methyl cellulose, hydroxypropyl cellulose, hydroxypropyl methyl cellulose, polyvinylpyrrolidone, polyvinylalcohol or starch.

Examples of drug-complexing agents or solubilizers include polyethylene glycols, caffeine, xanthene, gentisic acid and cylodextrins.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc and zinc stearate.

Examples of glidants include silicon dioxide, talc and cornstarch.

The CETP inhibitor composition may be formed according to any conventional method. In one embodiment, the composition is formed by blending the solid amorphous dispersion and optional excipients using procedures well-known in the art (see, for example, Remington's *Pharmaceutical Sciences* (18th ed. 1990)). Examples of blending equipment include twin-shell blenders, fluidized beds, and V blenders.

In another embodiment, the composition is granulated. Exemplary methods are wet-granulation and dry-granulation. The solid amorphous dispersion may be granulated, with or without the addition of other optional excipients. For example, the solid amorphous dispersion, a disintegrant, and a porosigen may be granulated by mechanical means by, for example, roller compaction or "slugging," followed by milling to form granules. The granules typically have improved flow, handling, blending, and compression properties relative to the ungranulated materials. Wet granulation techniques may also be employed, provided the solvents and process selected do not alter the properties of the solid amorphous dispersion. When wet granulation is used, the granulation liquid is typically removed from the granules during or after the granulation process. The so-formed granules typically have an average diameter ranging from 50 μm to 1000 μm, preferably 50 μm to about 800 μm, although granules outside this range can be used. Improved wetting, disintegrating, dispersing and dissolution properties may be obtained by the inclusion of other excipients described above.

In another embodiment, the CETP inhibitor composition comprises the solid amorphous dispersion coated with a protective coating. The coating is not acidic and substantially separates the solid amorphous dispersion from the HMG-CoA reductase inhibitor. Preferably, the coating material is aqueous soluble or dispersable in the use environment. Examples of coating materials include sugars, such as glucose, sucrose, xylitol, fructose, lactose, mannitol, sorbitol, and maltitol; cellulosic polymers, such as ethyl cellulose, methyl cellulose, hydroxyethyl cellulose, hydroxypropyl cellulose, and hydroxypropylmethyl cellulose; non-cellulosic polymers such as polyethylene glycol, polyethylene oxide, polypropylene glycol, polyethylene-polypropylene glycol copolymers (poloxamers), polyvinyl pyrrolidinone, starch, dextran, dextrin, polydextrose, polyalkenes, polyethers, polyvinyl alcohols, polyvinyl halides, polyvinyl ethers; waxes, such as synthetic wax, microcrystalline wax, paraffin wax, Carnauba wax, and beeswax; and glycerides, such as glyceryl monooleate, glyceryl monostearate, glyceryl palmitostearate, polyethoxylated castor oil derivatives, glyceryl mono-, di- and tribehenates, hydrogenated vegetable oils, glyceryl tripalmitate, glyceryl tristearate. Mixtures of coating materials may also be used. Preferred coating materials include cellulosic polymers such as hydroxylethyl cellulose, hydroxypropyl cellulose, and hydroxypropyl methylcellulose; non-cellulose polymers such as polyethylene glycol, polyethylene oxide, poloxamers, and polyvinyl pyrrolidinone; and mixtures thereof.

The solid amorphous dispersion may be coated using any method known in the art, including solution coating and hot-melt coating processes. In solution coating processes, the coating is made by first forming a solution or suspension comprising the coating excipient, a liquid (e.g., a solvent), and optional coating additives. The coating materials may be completely dissolved in the liquid, or only dispersed in the liquid as an emulsion or suspension or anywhere in between. Latex dispersions are a specific example of an emulsion or suspension that may be useful as a coating solution. The liquid used for the solution should be inert in the sense that it does not react with or degrade the drug, and be pharmaceutically acceptable. Preferably, the liquid is volatile. By "volatile" is meant that the material has a boiling point of less than about 150° C. at ambient pressure, although small amounts of liquids with higher boiling points can be used and acceptable results still obtained.

Examples of liquids suitable for use in coating the solid amorphous dispersion include alcohols, such as methanol, ethanol, isomers of propanol and isomers of butanol; ketones, such as acetone, methylethyl ketone and methyl isobutyl ketone; hydrocarbons, such as pentane, hexane, heptane, cyclohexane, methylcyclohexane, octane and mineral oil; ethers, such as methyl tert-butyl ether, ethyl ether and ethylene glycol monoethyl ether; chlorocarbons, such as chloroform, methylene dichloride and ethylene dichloride; tetrahydrofuran; dimethylsulfoxide; N-methylpyrrolidinone; acetonitrile; water; and mixtures thereof.

The coating formulation often includes additives to ease application or improve the durability or stability of the coating. Preferably, any coating additive used is non-acidic. Examples of coating additives include plasticizers, such as mineral oils, petrolatum, lanolin alcohols, polyethylene glycol, polypropylene glycol, sorbitol and triethanol amine; pore formers, such as polyethylene glycol, polyvinyl pyrrolidone, polyethylene oxide, hydroxyethyl cellulose and hydroxypropylmethyl cellulose; and glidants, such as colloidal silicon dioxide, talc and cornstarch.

The coating may be formed on the solid amorphous dispersion by contacting the dispersion with the coating formulation using standard coating equipment, such as fluidized bed coaters (e.g., Würster coaters or top-spray coaters, available from Glalt Air Technologies, Inc. of Ramsey, N.J. and from Niro Pharma Systems of Bubendorf, Switzerland) and rotary granulators (e.g., CF-Granulator, available from Freund Corp). In some cases, the solid amorphous dispersion is granulated prior to coating with the non-acidic coating.

In one method, a Würster fluidized-bed system is used. In this system, a cylindrical partition (the Würster column) is placed inside a conical product container in the apparatus. Air passes through a distribution plate located at the bottom of the product container to fluidize the solid amorphous dispersion, with the majority of the upward moving air passing through the Würster column. The solid amorphous dispersion particles are drawn into the Würster column, which is equipped with an atomizing nozzle that sprays the coating formulation upward. The solid amorphous dispersion particles are coated as they pass through the Wurster column, with the liquid being removed as the dispersion particles exit the column.

Alternatively, a top-spray method can be used to apply the coating. In this method, the coating formulation is sprayed down onto the fluidized dispersion particles. The liquid evaporates from the coated dispersion particles and the coated dispersion particles are re-fluidized in the apparatus. Coating continues until the desired coating thickness is achieved. Generally, it is preferred that the coating be at least 1 μm thick, preferably at least 5 μm thick, and more preferably at least 10 μm thick.

In another method, the coating is applied to the solid amorphous dispersion using a wet-granulation technique. In this method, the coating material is first dissolved or suspended in a granulation fluid. This granulation mixture is then sprayed onto or mixed with the solid amorphous dispersion, resulting in a thin layer of the coating material on the outside surface of the resulting granules. The granulation fluid is removed from the granules in a subsequent drying step.

The coating may also be applied using a hot-melt coating technique. In this method, the coating excipients and additives are first melted and then sprayed onto the dispersion particles. Typically, the hot-melt coating is applied in a fluidized bed equipped with a top-spray arrangement.

Another method for applying a hot-melt coating to the solid amorphous dispersion particles is to use a modified melt-congeal method. In this method, the dispersion particles are suspended in the molten coating excipients, the melting point of the dispersion being greater than the melting point of the coating excipients. This suspension is then formed into droplets comprising dispersion particles substantially surrounded by the coating excipients. The droplets are typically formed through the use of an atomizer, such as a rotary or spinning-disk atomizer. The droplets are then cooled to congeal the coating excipients, forming the coated dispersion.

The coating may also be applied in a rotary granulator. In such devices, horizontal discs rotate at high speed, forming a rotating "rope" of dispersion particles at the walls of the vessel. The coating is sprayed into this rope, coating the solid amorphous dispersion. This technique can be used with hot-melt and liquid-based coating solutions.

The HMG-CoA reductase inhibitor composition comprises the HMG-CoA reductase inhibitor and optional excipients, depending on the dosage form being prepared. The amount of the HMG-CoA reductase inhibitor may vary according to the desired dose of HMG-CoA reductase inhibitor. Preferably, the HMG-CoA reductase inhibitor is crystalline. The HMG-CoA reductase composition preferably stabilizes the HMG-CoA reductase inhibitor, particularly from degradation due to the presence of acidic materials in the dosage form or processing environment, as well as protects the HMG-CoA reductase inhibitor from photochemical decomposition during storage.

In a preferred embodiment, the HMG-CoA reductase inhibitor composition comprises a stabilizing agent. The stabilizing agent stabilizes the HMG-CoA reductase inhibitor by reducing acid catalyzed degradation. The stabilizing agent may be a basic inorganic pharmaceutically acceptable salt. Exemplary salts include: salts of calcium, such as calcium carbonate and calcium hydroxide; salts of magnesium, such as magnesium carbonate, magnesium hydroxide, magnesium oxide, magnesium silicate, magnesium aluminate, and aluminum magnesium hydroxide; salts of lithium, such as lithium hydroxide and similar lithium compounds; or, other similarly suitable salts of alkaline earth metals. The basic inorganic salts of calcium, lithium or magnesium can be utilized in a weight ratio ranging between about 0.1 to 1 and about 50 to 1 of salt compound to active ingredient.

A preferred stabilizing agent is calcium carbonate. The inventors have observed that the size of the calcium carbonate particles is relative to the effectiveness of calcium carbonate as a stabilizing agent, with smaller particles size resulting in better performance as a stabilizing agent. Preferred grades of calcium carbonate are precipitated grades of calcium carbonate having a particle size of less than about ten microns (μm). Exemplary grades of precipitated calcium carbonate include Vicality Medium PCC and Vicality Heavy PCC available from Specialty Minerals, Pre-carb 15 available from Mutchler, and PCC-250 available from Particle Dynamics.

The HMG-CoA reductase composition may also include, in addition to a stabilizing metal or alkaline earth metal salt, additional excipients which are known as suitable agents in the art comprising combinations and concentrations as further described below. In a preferred embodiment, the HMG-CoA reductase composition contains conventional additional materials suitable for forming a tablet. Such excipients include a diluent, binder, and disintegrant. Antioxidants can also be incorporated into the HMG-CoA reductase inhibitor composition to prevent any oxidation of the drug compound. For example, antioxidants that could be used are butylated hydroxyanisole, sodium ascorbate, butylated hydroxytoluene, sodium metabisulfate, malic acid, citric acid and ascorbic acid.

In one HMG-CoA reductase inhibitor composition, the composition comprises a stabilizing agent, diluents, disintegrant, and surfactant. The basic excipient, calcium carbonate, has been found to chemically stabilize HMG-CoA reductase inhibitors, such as atorvastatin calcium. Microcrystalline cellulose and hydrous lactose are applied as suitable diluents. Croscarmellose sodium is present as a disintegrant. The nonionic detergent Tween 80 is used as a surfactant. The composition also contains hydroxypropyl cellulose as binder selected from among several applicable substances such as, i.e., polyethylene glycol, polyvinylpyrrolidone, polyvinyl alcohol, hydroxymethylcellulose or hydroxypropylmethylcellulose. As anti-oxidants, reagents such as butylated hydroxyanisole, sodium ascorbate, ascorbic acid or others may optionally be incorporated in the composition. Magnesium stearate can be selected from a group including other substances such as stearic acid, palmitic acid, talc or similar lubricating compounds.

Other possible and supplemental ingredients such as preservatives, dryers, glidants, or colorants known as conventional by those skilled in the art may be included optionally in the HMG-CoA reductase inhibitor composition.

In one aspect, the HMG-CoA reductase inhibitor composition comprises the following concentration ranges of ingredients by weight: the HMG-CoA reductase inhibitor is in the range from about 1% to about 50%; calcium carbonate from about 5% to about 75%; microcrystalline cellulose from about 5% to about 75%; hydrous lactose from about 1% to about 80%; croscarmellose sodium from about 1% to about 15%; hydroxypropylcellulose from about 0.5% to about 6%; Tween 80 from about 0.1% to about 4%; magnesium stearate from about 0.25% to about 2%; and sodium ascorbate from about 0.0% to about 3%.

A more preferred HMG-CoA reductase inhibitor composition comprises the following approximate concentrations of ingredients by weight: about 13.9 wt % of the HMG-CoA reductase inhibitor atorvastatin hemicacium trihydrate; about 42.4 wt % of calcium carbonate; about 17.7 wt % microcrystalline cellulose; about 19.2 wt % pregelatanized starch; about 2.5 wt % hydroxypropyl cellulose; and about 0.5 wt % Tween 80.

The HMG-CoA reductase inhibitor composition may be formed by any conventional method for combining the HMG-CoA reductase inhibitor and excipients. Exemplary methods include wet and dry granulation. If wet granulation is used, a stabilizing agent such as calcium carbonate is preferably included to keep chemical degradation of the HMG-CoA reductase inhibitor at an acceptable level.

One exemplary method for forming the HMG-CoA reductase inhibitor composition comprises (a) milling an excess of the drug, (b) dissolving at least one binder additive in aqueous surfactant solution; (c) blending the milled drug with at least one drug-stabilizing additive and at least one diluent additive with the drug-stabilizing additive and one half of a disintegrant additive in a rotary mixing vessel equipped with a chopping device; (d) granulating the blended drug ingredient mixture of step (c) with the surfactantibinder solution of step (b) in gradual increments in the chopper equipped mixing vessel; (e) drying the granulated drug mixture overnight at about 500C; (f) sieving the dried granulated drug mixture; (g) tumble blending the sieved drug mixture with the remaining amount of the disintegrant additive; (h) mixing separately an aliquot of the drug mixture of step (g) with magnesium stearate, sieving same, and returning same to the drug mixture of step (g) and tumble blending the entire drug mixture.

In another embodiment, the HMG-CoA reductase inhibitor composition comprises the HMG-CoA reductase inhibitor coated with a protective coating. In this embodiment, crystals of the HMG-CoA reductase inhibitor or granules comprising the HMG-CoA reductase inhibitor and optional excipients are coated with a protective coating. The same protective coatings and coating methods described above for applying a protective coating to the solid amorphous dispersion may be used to coat the HMG-CoA reductase inhibitor.

The unitary dosage form is formed by combining the CETP inhibitor composition with the HMG-CoA reductase inhibitor composition such that the solid amorphous dispersion and HMG-CoA reductase inhibitor are substantially separate in the dosage form.

In one embodiment, the CETP inhibitor composition and HMG-CoA reductase inhibitor composition are blended together and then compressed to form the dosage form, such as tablets, caplets, or pills. Virtually any process can be used to blend the compositions, provided the solid amorphous dispersion and the HMG-CoA reductase inhibitor remain substantially separate in the dosage form. For example, the compositions can be blended in rotating shell mixers, fixed-shell mixers, planetary paddle mixers, and twin-shell mixers, all known in the art.

The compressed dosage forms may be formed using any of a wide variety of presses used in the fabrication of pharmaceutical dosage forms. Examples include single-punch presses, rotary tablet presses, and multilayer rotary tablet presses, all well-known in the art. See *Remington's Pharmaceutical Sciences* (18$^{th}$ Edition, 1990). The compressed dosage form may be of any shape, including round, oval, oblong, cylindrical, or triangular. The upper and lower surfaces of the compressed dosage form may be flat, round, concave, or convex.

When formed by compression, the dosage form preferably has a "strength" of at least 5 Kiloponds (Kp)/cm$^2$, and more preferably at least 7 Kp/cm$^2$. Here, "strength" is the fracture force, also known as the tablet "hardness," required to fracture a tablet formed from the materials, divided by the maximum cross-sectional area of the tablet normal to that force. The fracture force may be measured using a Schleuniger Tablet Hardness Tester, model 6D. To achieve the desired strength, the blend of the CETP inhibitor composition and HMG-CoA reductase inhibitor composition should be compressed with sufficient force while forming the dosage form while ensuring the solid amorphous dispersion and HMG-CoA reductase inhibitor remain substantially separate in the dosage form. The compression force required to achieve this strength will depend on the size of the tablet, but generally will be greater than about 5 kP/cm$^2$. Friability is a well-known measure of a dosage form's resistance to surface abrasion that measures weight loss in percentage after subjecting the dosage form to a standardized agitation procedure. Friability values of from 0.8 to 1.0% are regarded as constituting the upper limit of acceptability. Dosage forms having a strength of greater than 5 kP/cm$^2$ generally are very robust, having a friability of less than 0.5%, preferably less than 0.1%.

In some embodiments, the unitary dosage form also comprises a separating layer that physically separates the CETP inhibitor composition from the HMG-CoA reductase inhibitor composition. The separating layer is preferably non acidic. Examples of suitable materials for use in the separating layer include those listed above as being suitable for use in forming a protective coating around the solid amorphous dispersion.

Figure 5:
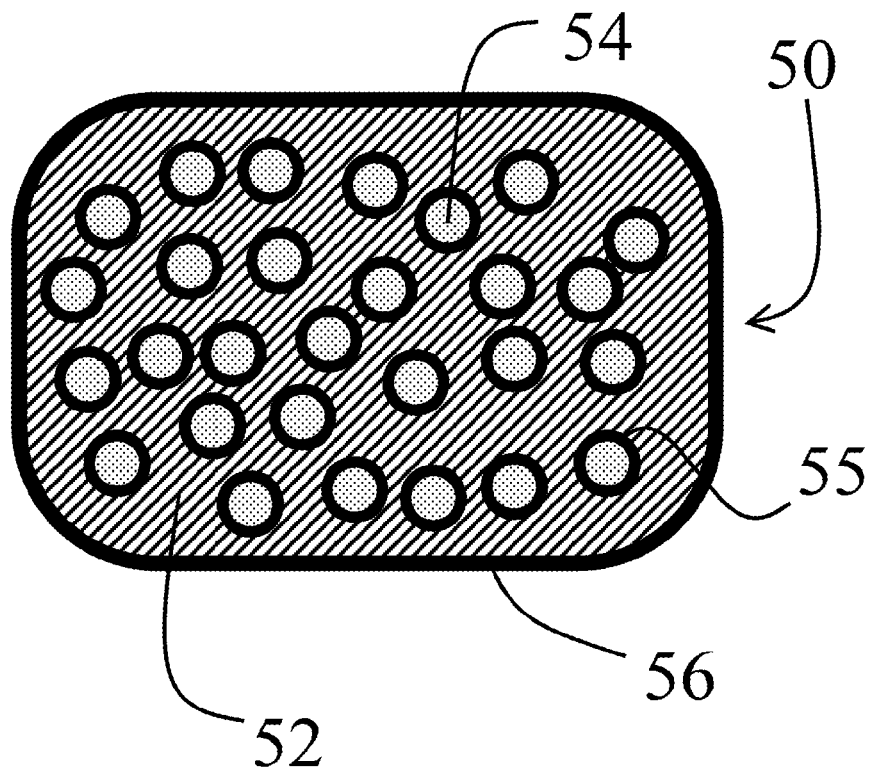

In one embodiment, the unitary dosage form comprises a first granulation comprising the solid amorphous dispersion of the CETP inhibitor and the acidic concentration-enhancing polymer mixed with a second granulation comprising the HMG-CoA reductase inhibitor, shown schematically as dosage form 50 in FIG. 5. Here, the CETP inhibitor granulation 52 is mixed with the HMG-CoA reductase inhibitor granulation 54 and then compressed into the unitary dosage form.

The following process may be used to form such a compressed unitary dosage form. First, the granules of the CETP inhibitor composition are prepared. For example, a solid amorphous dispersion containing about 25 wt % of the CETP inhibitor [2R,4S]4-[(3,5-bis-trifluoromethyl-benzyl) -methoxycarbonyl-amino]-2-ethyl-6-trifluoromethyl-3,4-dihydro-2H-quinoline-1-carboxylic acid ethyl ester in a concentration-enhancing polymer, such as hydroxypropylmethyl cellulose acetate succinate (HPMCAS), may be prepared via a spray drying process. Next, about 60.15 wt % of the solid amorphous dispersion, about 14.79 wt % of microcrystalline cellulose, and about 10.03 wt % of crospovidone may be blended for 15 minutes in, for example, a twin-shell blender. Next, about 0.25 wt % magnesium stearate is added and the mixture blended for another 5 minutes. The blend may then be densified using a roller compactor. The size of the compacts may then be reduced by milling. Next, about 14.78 wt % dibasic calcium phosphate anhydrous is added and blended for about 5 minutes in a twin-shell blender, forming the granules of the CETP inhibitor composition with an average particle size of about 140 μm.

Next, the granules of the HMG-CoA reductase inhibitor composition are prepared. For example, about 13.9 wt % of the HMG-CoA reductase inhibitor atorvastatin hemicacium trihydrate; about 42.4 wt % of calcium carbonate; about 17.7 wt % microcrystalline cellulose; and about 19.2 wt % pregelatanized starch may be fluidized in a fluidized bed granulator. An aqueous solution containing about 2.5 wt % hydroxypropyl cellulose and about 0.5 wt % Tween 80 is then sprayed into the bed to form granules. The granules are then dried in the bed to remove the granulation water. The size of the granules may then be reduced by milling to form granules with a mean granule size of about 110 μm.

To form a unitary dosage form comprising 60 mgA of the CETP inhibitor and 40 mgA of the HMG-CoA reductase inhibitor, 399 mg of the CETP inhibitor granules and the 313 mg of the HMG-CoA reductase inhibitor granules are then blended in a twin shell blender for 10 minutes. Next, 1.8 mg of the lubricant magnesium stearate is added to the mixture and blended for and additional 5 minutes. Compressed tablets containing 713.78 mg of material are then formed using a 0.3301-inch (0.8385-cm) by 0.6603-inch (1.6772-cm) modified oval tooling. Compression to 20 kN results in a tablet with a hardness of 8.2 kP. Based on a tablet cross sectional area of 1.1 cm$^2$, this corresponds to a tablet strength of 7.5 kP/cm$^2$.

Alternatively, the mixture of the two compositions described above may be filled into a capsule, such as a hard- or soft-gelatin capsule or a capsule made from some other material, e.g., starch, to form the unitary dosage form.

In another embodiment, the unitary dosage form may be formed by the following process. First, the HMG-CoA reductase inhibitor may be mixed with excipients and granulated using a dry- or wet-granulation technique to form granules of the HMG-CoA reductase inhibitor composition. The HMG-CoA reductase inhibitor composition granules may then be mixed with the solid amorphous dispersion comprising the CETP inhibitor and the acidic concentration-enhancing polymer and optional excipients and the resulting mixture granulated using dry- or wet-granulation techniques. The resulting granules comprising the HMG-CoA reductase inhibitor composition and the CETP inhibitor composition may then be compressed into a tablet, caplet or pill, or the granules may be filled into a capsule, such as a hard- or soft-gelatin capsule.

In another embodiment, the unitary dosage form may be formed by the following process. First, the solid amorphous dispersion comprising the CETP inhibitor and the acidic concentration-enhancing polymer may be mixed with optional excipients and granulated using a dry- or wet-granulation technique to form granules of the CETP inhibitor composition. The CETP inhibitor composition granules may then be mixed with the HMG-CoA reductase inhibitor and optional excipients and the resulting mixture granulated using dry- or wet-granulation techniques. The resulting granules comprising the HMG-CoA reductase inhibitor composition and the CETP inhibitor composition may then be compressed into a tablet, caplet or pill, or the granules may be filled into a capsule, such as a hard- or soft-gelatin capsule.

In another embodiment, the unitary dosage form may be formed by the following process. First, the HMG-CoA reductase inhibitor composition may be compressed into a tablet, caplet, or pill. The resulting compressed tablet, caplet, or pill may then be placed into a capsule along with the CETP inhibitor composition. Alternatively, the CETP inhibitor composition may first be compressed into a tablet, caplet, or pill. The resulting compressed tablet, caplet, or pill may then be placed into a capsule along with the HMG-CoA reductase inhibitor composition.

In another embodiment, the unitary dosage form may be formed by the following process. First, the HMG-CoA reductase inhibitor composition may be formed into multiparticulates using processes well known in the art, such as by extrusion spheronization, cryogenic pelletization, spray drying, or melt congealing. See, for example, *Remington: The Science and Practice of Pharmacy*, $20^{th}$ Edition (2000). The resulting multiparticulates may then be placed into a capsule along with the CETP inhibitor composition. Alternatively, the CETP inhibitor composition may first be formed into multiparticulates and placed into a capsule along with the HMG-CoA reductase inhibitor composition. In another method, the HMG-CoA reductase inhibitor composition may be formed into multiparticulates and the CETP inhibitor composition may be formed into multiparticulates, which are then mixed and placed into a capsule.

In another embodiment, the unitary dosage form is in the form of a kit. The kit comprises two separate compositions: (1) one containing the solid amorphous dispersion comprising a CETP inhibitor and an acidic concentration-enhancing polymer, and (2) one containing the HMG-CoA reductase inhibitor. The kit is designed such that the HMG-CoA reductase inhibitor and the solid amorphous dispersion are substantially separate. The kit includes means for containing the separate compositions such as a divided container, such as a bottle, pouch, box, bag or other container known in the art, or a divided foil packet; however, the separate compositions may also be contained within a single, undivided container. An example of this type of kit is a blister pack wherein each individual blister contains two (or more) tablets, one (or more) tablet(s) comprising the CETP inhibitor composition, and the second (or more) tablet(s) comprising the HMG-CoA reductase inhibitor composition. In one embodiment, the HMG-CoA reductase inhibitor composition is in the form of a compressed tablet. In another embodiment, the CETP inhibitor composition is in the form of a compressed tablet. In another embodiment, the HMG-CoA reductase inhibitor composition is in the form of multiparticulates. In another embodiment, the CETP inhibitor composition is in the form of multiparticulates. Typically the kit includes directions for the administration of the separate components.

Thus, in one embodiment, the unitary dosage form comprises a kit, the kit comprising (1) a therapeutically effective amount of a CETP inhibitor in a CETP inhibitor composition; (2) a therapeutically effective amount of an HMG-CoA reductase inhibitor in an HMG-CoA reductase inhibitor composition; and (3) a container for containing the CETP inhibitor composition and the HMG-CoA reductase inhibitor composition.

An example of such a kit, alluded to above, is a so-called blister pack. Blister packs are well known in the packaging industry and are widely used for the packaging of pharmaceutical unit dosage forms such as tablets, capsules, and the like. Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. Tablet(s) or capsule(s) can then be removed via said opening.

It may be desirable to provide a memory aid on the kit, e.g., in the form of numbers next to the tablets or capsules whereby the numbers correspond with the days of the regimen during which the tablets or capsules so specified should be ingested. Another example of such a memory aid is a calendar printed on the card, e.g., as follows "First Week, Monday, Tuesday, . . . etc. . . . . . Second Week, Monday, Tuesday, . . . ", etc. Other variations of memory aids will be readily apparent.

Coatings

The unitary dosage form may optionally be coated with a conventional coating well known in the art. The coatings may be used to mask taste, improve appearance, facilitate swallowing of the dosage form, or to delay, sustain or otherwise control the release of the drug from the dosage form. Such coatings may be fabricated by any conventional means including fluidized bed coating, spray-coating, pan-coating and powder-coating using aqueous or organic solvents. Examples of suitable coating materials include sucrose, maltitol, cellulose acetate, ethyl cellulose, methylcellulose, sodium carboxymethyl cellulose, hydroxyethyl cellulose, hydroxypropyl cellulose, hydroxypropyl methylcellulose, polymethacrylates, polyacrylates, polyvinyl alcohol, polyvinyl pyrrolidone, cetyl alcohol, gelatin, maltodextrin, paraffin wax, microcrystalline wax, and Carnauba wax. Mixtures of polymers may also be used. Preferred coatings include the commercial aqueous coating formulations Surelease® and Opadry® available from Colorcon Inc. (West Point, Pa.).

In some cases, to avoid poor toleration or to avoid degradation, it is desired that drugs in the unitary dosage form not be released in the stomach. In these instances, the dosage form may also be overcoated with one or more pH-sensitive coating compositions, commonly referred to in the pharmaceutical arts as "enteric" coatings, by conventional procedures in order to delay the release of drug until it reaches the duodenum or small intestine. pH-sensitive polymers suitable as enteric coatings include those which are relatively insoluble and impermeable at the pH of the stomach, but which are more soluble or disintegrable or permeable at the pH of the duodenum and small intestine. Such pH-sensitive polymers include polyacrylamides, phthalate derivatives such as acid phthalate of carbohydrates, amylose acetate phthalate, cellulose acetate phthalate (CAP), other cellulose ester phthalates, cellulose ether phthalates, hydroxypropylcellulose phthalate (HPCP), hydroxypropyl ethylcellulose phthalate (HPECP), hydroxypropyl methylcellulose phthalate (HPMCP), HPMCAS, methylcellulose phthalate (MCP), polyvinyl acetate phthalate (PVAcP), polyvinyl acetate hydrogen phthalate, sodium CAP, starch acid phthalate, cellulose acetate trimellitate (CAT), styrene-maleic acid dibutyl phthalate copolymer, styrene-maleic acid/polyvinylacetate phthalate copolymer, styrene and maleic acid copolymers, polyacrylic acid derivatives such as acrylic acid and acrylic ester copolymers, polymethacrylic acid and esters thereof, polyacrylic and methacrylic acid copolymers, shellac and copolymers of vinyl acetate and crotonic acid.

A preferred group of pH-sensitive polymers includes CAP, PVAcP, HPMCP, HPMCAS, anionic acrylic copolymers of methacrylic acid and methylmethacrylate, and copolymers of acrylic acid and at least one acrylic acid ester.

To apply the pH-sensitive coating to the dosage form, the pH-sensitive polymer is first dissolved or suspended in a suitable solvent to form a coating solution. Useful solvents for this purpose include ketones, such as acetone; alcohols, such as methanol, ethanol, isopropyl alcohol, n-propyl alcohol, and the various isomers of butanol; chlorinated hydrocarbons, such as methylene chloride; water; and mixtures of these solvents. The polymer may also be suspended in the solvent. The coating solution may also comprise a latex of the pH-sensitive polymer suspended in an aqueous solution.

The coating solution may also contain one or more plasticizers, such as polyethylene glycols, triethyl citrate, propylene glycols, diethyl phthalate, dibutyl phthalate, castor oil, triacetin and others known in the art. The coating solution may also contain one or more emulsifiers, such as polysorbate-80. Coating is conducted in conventional fashion, typically by dipping, spray-coating, or pan-coating.

The coating solution may also contain a base or buffer, such as those discussed above. Use of a base or buffer will ensure the pH of the coating solution is not so low as to increase chemical degradation of the HMG-CoA reductase inhibitor. Use of a base or buffer may also be used to minimize reaction of the coating formulation with other excipients in the dosage form.

The unitary dosage forms of the present invention may be used to treat any condition, which is subject to treatment by administering a CETP inhibitor and an HMG-CoA reductase inhibitor, as disclosed in commonly assigned, copending U.S. Patent Application No. 2002/0035125A1. The disclosure of which is herein incorporated by reference.

In one aspect, the unitary dosage forms of the present invention are used for antiatherosclerotic treatment.

In another aspect, the unitary dosage forms of the present invention are used for slowing and/or arresting the progression of atherosclerotic plaques.

In another aspect, the unitary dosage forms of the present invention are used for slowing the progression of atherosclerotic plaques in coronary arteries.

In another aspect, the unitary dosage forms of the present invention are used for slowing the progression of atherosclerotic plaques in carotid arteries.

In another aspect, the unitary dosage forms of the present invention are used for slowing the progression of atherosclerotic plaques in the peripheral arterial system.

In another aspect, the unitary dosage forms of the present invention, when used for treatment of atherosclerosis, causes the regression of atherosclerotic plaques.

In another aspect, the unitary dosage forms of the present invention are used for regression of atherosclerotic plaques in coronary arteries.

In another aspect, the unitary dosage forms of the present invention are used for regression of atherosclerotic plaques in carotid arteries.

In another aspect, the unitary dosage forms of the present invention are used for regression of atherosclerotic plaques in the peripheral arterial system.

In another aspect, the unitary dosage forms of the present invention are used for HDL elevation treatment and antihyperlipidemic treatment (including LDL lowering).

In another aspect, the unitary dosage forms of the present invention are used for antianginal treatment.

In another aspect, the unitary dosage forms of the present invention are used for cardiac risk management.

Other features and embodiments of the invention will become apparent from the following examples, which are given for illustration of the invention, rather than for limiting its intended scope.

EXAMPLES

Example 1

A granulation of the HMG-CoA reductase inhibitor atorvastatin and a granulation of a solid amorphous dispersion containing a CETP inhibitor and a concentration-enhancing polymer were each formed separately. The two granulations were combined and stored at 50° C. and 75% relative humidity for 3 weeks. The stability of atorvastatin was measured and found to be improved relative to a control composition.

The following process was used to form a spray-dried dispersion containing 25 wt % [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib) and 75 wt % hydroxypropylmethyl cellulose acetate succinate (medium granular grade available from Shin Etsu, located in Japan) (referred to herein as "HPMCAS-MG"). First, a spray solution was formed containing 25 g torcetrapib, 75 g HPMCAS-MG, and 900 g acetone. The spray solution was pumped using a high-pressure pump (Zenith Z-Drive 2000 High-Pressure Gear Pump) to a spray drier (Niro type XP Portable Spray-Dryer with a Liquid-Feed Process Vessel [PSD-1]) equipped with a pressure atomizer (Spraying Systems Pressure Nozzle and Body (SK 79-16)). The PSD-1 was equipped with a 9-inch chamber extension. The spray drier was also equipped with a diffuser plate having a 1% open area. The nozzle sat flush with the diffuser plate during operation. The spray solution was pumped to the spray drier at about 185 gm/min, with an atomization pressure of about 280 psi. Drying gas (nitrogen) was circulated through the diffuser plate at an inlet temperature of about 98° C. The evaporated solvent and wet drying gas exited the spray drier at a temperature of 31±4° C. The spray-dried dispersion formed by this process was collected in a cyclone, and had a bulk specific volume of about 5 cm$^3$/gm. The solid amorphous dispersion was post-dried using a Gruenberg single-pass convection tray dryer operating at 40° C. for about 16 hours.

The spray-dried solid amorphous dispersion was evaluated in an in vitro dissolution test using a microcentrifuge method. In this test, 7.2 mg of the spray-dried solid amorphous dispersion was placed into a microcentrifuge tube. The tube was placed in a 37° C. sonicating bath, and 1.8 mL phosphate buffered saline (PBS) at pH 6.5 and 290 mOsm/kg was added, resulting in a torcetrapib concentration of 1000 µg/mL if all of the drug had dissolved. The sample was quickly mixed using a vortex mixer for about 60 seconds. The sample was centrifuged at 13,000 G at 37° C. for 1 minute. The resulting supernatant solution was then sampled and diluted 1:6 (by volume) with methanol and then analyzed by high-performance liquid chromatography (HPLC). The contents of the tube was mixed on the vortex mixer and allowed to stand undisturbed at 37° C. until the next sample was taken. Samples were collected at 4, 10, 20, 40, 90, and 1200 minutes. The concentrations of drug obtained in these samples are shown in Table 1, which represent the average of duplicate tests.

As a control, an in vitro dissolution test was performed using the procedures described above except that 1.8 mg of crystalline drug was used. The concentrations of drug obtained in vitro dissolution tests are shown in Table 1.

TABLE 1

| Sample | Time (min) | Torcetrapib Concentration (µg/mL) | AUC (min-µg/mL) |
| --- | --- | --- | --- |
| Solid Amorphous Dispersion | 0 | 0 | 0 |
|  | 4 | 328 | 660 |
|  | 10 | 701 | 3,700 |
|  | 20 | 781 | 11,200 |
|  | 40 | 805 | 27,000 |
|  | 90 | 780 | 66,600 |
|  | 1200 | 439 | 743,200 |
| Crystalline Drug | 0 | 0 | 0 |
|  | 4 | <1 | <2 |
|  | 10 | <1 | <8 |
|  | 20 | <1 | <18 |
|  | 40 | <1 | <38 |
|  | 90 | <1 | <88 |
|  | 1200 | <1 | <1,200 |

The results of these dissolution tests are summarized in Table 2, which shows the maximum concentration of torcetrapib in solution during the first 90 minutes of the test ($MDC_{90}$), the area under the aqueous concentration versus time curve after 90 minutes ($AUC_{90}$), and the concentration at 1200 minutes ($C_{1200}$).

TABLE 2

| Sample | Aqueous-Soluble Polymer | Torcetrapib Conc. in the Dispersion (wt %) | Receptor Solution | $MDC_{90}$ (µg/mL) | $AUC_{90}$ (min-µg/mL) | $C_{1200}$ (µg/mL) |
| --- | --- | --- | --- | --- | --- | --- |
| Solid Amorphous Dispersion | HPMCAS-MF | 25 | PBS | 805 | 66,600 | 439 |
| Crystalline Drug | None | NA | PBS | <1 | <88 | <1 |

The results summarized in Table 2 show that the solid amorphous dispersion provided concentration enhancement relative to crystalline drug. The solid amorphous dispersion provided a $C_{max.90}$ value that was greater than 805-fold that of the crystilline drug, and the $AUC_{90}$ value that was greater than 756-fold that of the crystalline drug.

A granulation of the above torcetrapib dispersion was made with the following composition: 60 wt % solid amorphous dispersion; 14.8 wt %, microcrystalline cellulose (Avicel PH105, available from FMC Corp., Philadelphia, Pa.); 10.0 wt %, crospovidone (Polyplasdone, available from International Specialty Products, Wayne, N.J.); 14.8 wt %, dibasic calcium phosphate anhydrous (A-Tab, available from Rodia, Inc., Cranbury, N.J.); and 0.5 wt %, and magnesium stearate. First, the solid amorphous dispersion, microcrystalline cellulose, and crospovidone were added to an 8 quart twinshell blender and blended for 15 minutes. Half of the magnesium stearate was added, and the mixture was blended for 5 minutes. The mixture was roller-compacted using a TF-mini roller compactor with a roller pressure of 450 psi, a roller speed of 4 rpm, an auger speed of 25 rpm, and a target ribbon thickness of 0.07 to 0.08-inches. The mixture was then milled using an M5A mill with a 0.033 inch Conidur screen, at 500 rpm, with the bar head in the knife direction. Next, the granulation was added to an 8 quart twin shell blender and blended for 15 minutes. Dicalcium phosphate was added, and the mixture was blended for 15 minutes. The remaining half of the magnesium stearate was added, and the mixture was blended for 5 minutes. The resulting granulation formed the CETP inhibitor composition.

A granulation of atorvastatin calcium was made using the following process. The granulation contained 13.9 wt % atorvastatin trihydrate hemicalcium salt, 42.4 wt % calcium carbonate (Pre-carb 150, available from Mutchler Inc., Westwood, N.J.), 17.7 wt % microcrystalline cellulose (Avicel PH 101, FMC Corp.), 3.8 wt % croscarmellose sodium (AcDiSol, FMC Corp.), 0.5 wt % polysorbate 80 (Crillet 4HP, Croda, Parsippany, N.J.), 2.6 wt % hydroxypropyl cellulose (Klucel EF, Hercules, Wilmington, Del.), and 19.2 wt % pregelatanized starch (Starch 1500, available from Colorcon, Inc., West Point, Pa.). To form the granulation, the atorvastatin calcium, calcium carbonate, microcrystalline cellulose, and starch were charged into a fluidized bed granulation apparatus. A granulating fluid comprising the polysorbate 80 and hydroxypropyl cellulose dissolved in water was sprayed into the fluidized material to form the granules. The weight of water used was equal to half the weight of the granulation. The granulation was then dried in the fluidized bed using air with an inlet temperature of about 45° C. until an end point of less than 2% water loss on drying was achieved. The granules were then milled using a Fitzpatrick M5A mill. The mill was fitted with a ~0.03-inch rasping plate and a rasping bar operating at about 500 rpm in a knives forward direction (counter-clockwise). The average particle size of the granules was about 105 μm using screen analysis. This composition comprised the HMG-CoA reductase inhibitor composition.

To form Example 1, 86 wt % of the CETP inhibitor composition and 14 wt % of the HMG-CoA reductase inhibitor composition were mixed together in a twin-shell blender, screened, mixed again, and then compressed into slugs. The slugs were then milled using a mortar and pestle. The acidic concentration-enhancing polymer HPMCAS comprised 38.7 wt % of Example 1, and atorvastatin calcium comprised 1.96 wt % of Example 1 for an HPMCAS/atorvastatin ratio of 19.7 (w/w).

Control 1 consisted of a mixture of crystalline atorvastatin calcium (2 wt %) and the CETP inhibitor solid amorphous dispersion (98 wt %). The crystalline atorvastatin calcium and the solid amorphous dispersion were mixed together in a Turbula mixer, screened, mixed again, and then compressed into slugs. The slugs were then milled using a mortar and pestle. The acidic concentration-enhancing polymer HPMCAS comprised 73.5 wt % of Control 1, and atorvastatin calcium comprised 2 wt % of Control 1, for an HPMCAS/atorvastatin ratio of 36.8 (w/w).

Control 2 consisted of a mixture of crystalline atorvastatin (1.42 wt %), the CETP inhibitor dispersion (62.50 wt %), and all of the excipients used for both of the granulations (calcium carbonate—4.32 wt %, croscarmellose sodium—0.39 wt %, microcrystalline cellulose—3.07 wt %, pregelatinized starch—1.95, polysorbate 80—0.05 wt %, hydroxypropyl cellulose—0.26, crospovidone—10.42, magnesium Stearate—0.26, dicalcium phosphate—15.36 wt %). The materials were mixed in a Turbula mixer, screened, mixed again and then compressed into slugs. The slugs were then milled using a mortar and pestle. The acidic concentration-enhancing polymer HPMCAS comprised 46.9 wt % of Control 2, and atorvastatin comprised 1.42 wt % of Control 1, for an HPMCAS/atorvastatin ratio of 33.0 (w/w).

Example 1, and Controls 1 and 2, were stored at 50° C. and 75% relative humidity for 3 weeks to increase the rate of chemical and physical changes occurring in the materials in order to simulate a longer storage interval in a typical storage environment.

Following storage, the samples were analyzed for atorvastatin purity using HPLC. To analyze the samples by HPLC, a sample of the composition containing about 0.4 mgA atorvastatin was added to a dissolving solvent. The dissolving solvent was made by combining 150 mL 50 mM ammonium acetate (pH 7.0), 600 mL acetonitrile, and 250 mL methanol. Mobile phase A was made by adding 3 mL acetic acid to 530 mL water, adjusting to pH 4.0 with ammonium hydroxide, then adding 270 mL acetonitrile and 200 mL tetrahydrofuran. Mobile phase B was made by adding 1 mL acetic acid to 100 mL water, adding half of the amount of ammonium hydroxide used to adjust Mobile phase A, then adding 700 mL acetonitrile and 200 mL tetrahydrofuran. The samples were analyzed using a Waters Spherisorb ODS2 column, with a solvent flow rate of 1.5 mumin. Table 3 shows the solvent gradient used.

TABLE 3

| Time | % A | % B |
|---|---|---|
| 0 | 100 | 0 |
| 15 | 100 | 0 |
| 35 | 0 | 100 |
| 50 | 0 | 100 |
| 51 | 100 | 0 |
| 60 | 100 | 0 |

The UV absorbance of atorvastatin and atorvastatin impurities were measured at a wavelength of 244 nm. The atorvastatin lactone impurity eluting after about 10.4 minutes was chosen as the basis for comparison. All impurity peak areas were added and the lactone impurity as percent of total peak area was calculated to give the degree of degradation. Results are shown in Table 4.

TABLE 4

| Sample | Degree of Degradation (wt %) |
|---|---|
| Example 1 | 0.17 |
| Control 1 | 1.55 |
| Control 2 | 2.66 |

The results from Table 4 show that the atorvastatin in the sample of Control 1 (atorvastatin mixed with the CETP inhibitor solid amorphous dispersion) contained 1.55 wt % lactone impurity. Control 2 (a mixture containing crystalline atorvastatin, CETP inhibitor solid amorphous dispersion, and the excipients used in both granulations) contained 2.66 wt % lactone impurity. Example 1 showed that granulating the atorvastatin with excipients, then granulating the solid amorphous dispersion with excipients, followed by mixing the two granulations, provided improved atorvastatin stability. A relative degree of improvement in chemical stability was determined by taking the ratio of the degree of degradation of the drug in the control compositions and the degree of degradation of the drug in Example 1. When compared with Control 1, Example 1 had a relative degree of improvement of 9.12 (1.55 wt %/0.17 wt %). When compared with Control 2, Example 1 had a relative degree of improvement of 15.6.

Examples 2 and 3

To form Example 2, equal weights of the granulated CETP inhibitor composition of Example 1 and the granulated HMG-CoA reductase inhibitor composition of Example 1 were blended as described in Example 1 and 200 mg tablets were formed from the blend. The acidic polymer HPMCAS comprised 22.5 wt % of Example 2, and atorvastatin calcium comprised 6.95 wt % of Example 2, for a ratio of HPMCAS to atorvastatin of 3.24.

To form Example 3, tablets containing separate layers of the CETP inhibitor composition of Example 1 and the HMG-CoA reductase inhibitor composition of Example 1 were manufactured. Each of the tablets of Example 3 contained 400 mg of the dispersion granulation in one layer and 288 mg of the atorvastatin granulation in a second layer. The acidic concentration-enhancing polymer HPMCAS comprised 26.2 wt % of Example 3, and atorvastatin comprised 5.82 wt % of Example 3 for a HPMCAS to atorvastatin ratio of 4.5.

Examples 2 and 3 were stored at 50° C. and 75% relative humidity for 3 weeks, and analyzed using HPLC as described above. The results are shown in Table 5.

TABLE 5

| Sample | Degree of Degradation (wt %) |
|---|---|
| Example 2 | 0.09 |
| Example 3 | 0.04 |

Example 2 shows that tablets made by first forming separate granulations (one containing the solid amorphous dispersion and one containing the atorvastatin), and then blending the granulations to form a tablet, provide a dosage form with improved atorvastatin stability. Comparing Example 2 to Control 2 (a mixture containing crystalline atorvastatin CETP inhibitor dispersion, and the excipients used in both granulations), the relative degree of improvement was 29.6. Example 3 showed that tablets made by forming separate layers of the solid amorphous dispersion granulation and the atorvastatin granulation provided further improvement in atorvastatin stability. Comparing Example 3 to Control 2, the relative degree of improvement was 66.5.

Examples 4 to 11

Unitary dosage forms were made by the process described for Example 2 with the exceptions noted in Table 6. The properties of the tablets are given in Table 7.

TABLE 6

| Example | CETP Inhibitor Composition (wt %) | HMG-CoA Reductase Inhibitor Composition (wt %) | Tablet Weight (mg) | Tablet CETP Inhibitor Dose (mg) | Tablet Atorvastatin Calcium Dose (mg) | Acidic Polymer to HMG CoA Reductase Inhibitor Ratio (wt/wt) |
|---|---|---|---|---|---|---|
| Example 4* | 71.65 | 28.10 | 278.45 | 30 | 10 | 8.3 |
| Example 5* | 24.11 | 75.64 | 827.57 | 30 | 80 | 1.0 |
| Example 6* | 71.65 | 28.10 | 556.89 | 60 | 20 | 8.3 |
| Example 7* | 55.90 | 43.85 | 713.78 | 60 | 40 | 4.1 |
| Example 8* | 82.22 | 11.53 | 678.44 | 90 | 10 | 23.1 |
| Example 9* | 48.75 | 51.00 | 1227.57 | 90 | 80 | 3.1 |
| Example 10* | 90.84 | 8.91 | 878.45 | 120 | 10 | 33.0 |
| Example 11* | 83.40 | 16.36 | 956.89 | 120 | 20 | 16.5 |

*0.25 wt % Magnesium stearate was blended with the two compositions prior to forming the tablets.

TABLE 7

| Example | Modified Oval Tablet Size (cm x cm) | Tablet Cross Section Area (cm$^2$) | Tablet Hardness (kP) | Tablet Strength (kP/cm$^2$) |
|---|---|---|---|---|
| Example 4 | 0.6126 × 1.2253 | 0.6 | 13.2 | 22.0 |
| Example 5 | 0.8806 × 1.7615 | 1.2 | 31.9 | 26.6 |
| Example 6 | 0.7719 × 1.6492 | 1.0 | 14.2 | 14.2 |
| Example 7 | 0.8385 × 1.6772 | 1.1 | 8.2 | 7.5 |
| Example 8 | 0.8245 × 1.6492 | 1.1 | 23.4 | 21.3 |
| Example 9 | 1.0617 × 1.8999 | 1.6 | 45.7 | 28.6 |
| Example 10 | 0.8987 × 1.7976 | 1.3 | 8.6 | 6.6 |
| Example 11 | 0.9246 × 1.8491 | 1.3 | 9.4 | 7.2 |

Samples of the tablets of Examples 6, 7, 10, and 11 were stored for 6 weeks at 40° C. and 75% RH. Table 8 gives the concentration of the lactone degradant in the tablet before and after storage, as well as the degree of degradation of the atorvastatin calcium. These data show that formation of the tablets using the granulated compositions results in low degrees of degradation for atorvastatin calcium.

TABLE 8

| | Degradant Concentration (wt %) | | Degree of |
| Example | Before Storage | After Storage 6 weeks at 40° C./75% RH | Degradation (wt %) |
|---|---|---|---|
| Example 6 | 0.05 | 0.08 | 0.03 |
| Example 7 | 0.06 | 0.07 | 0.01 |

TABLE 8-continued

| | Degradant Concentration (wt %) | | Degree of |
| Example | Before Storage | After Storage 6 weeks at 40° C./75% RH | Degradation (wt %) |
|---|---|---|---|
| Example 10 | 0.09 | 0.12 | 0.03 |
| Example 11 | 0.03 | 0.10 | 0.07 |

Example 12

A granulation of the HMG-CoA reductase inhibitor atorvastatin and a solid amorphous dispersion containing a CETP inhibitor and a concentration-enhancing polymer were combined and stored at 40° C. and 75% relative humidity for 6 weeks. The composition showed acceptable amounts of chemical degradation of the HMG-CoA reductase inhibitor.

A spray-dried solid amorphous dispersion containing 40 wt % torcetrapib and 60 wt % hydroxypropyl methyl cellulose acetate succinate (high granular grade available from Shin Etsu, located in Japan) (referred to herein as "HPMCAS-HG") was formed using a process similar to the one described in Example 1 with the follow exceptions. The spray solution contained 20 g torcetrapib, 30 g HPMCAS-HG, and 450 g acetone. The spray solution was pumped into to the PSD-1 spray drier equipped with a pressure atomizer (Spraying Systems Pressure Nozzle and Body (SK 80-16)). The PSD-1 was equipped with a 9-inch chamber extension. The spray drier was also equipped with a diffuser plate having a 1% open area. The spray solution was pumped to the spray drier at about 145 gm/min, with an atomization pressure of about 250 psi. Drying gas (nitrogen) was circulated through the diffuser plate at an inlet temperature of about 97° C. The evaporated solvent and wet drying gas exited the spray drier at a temperature of 46° C. The solid amorphous dispersion was post-dried using a Gruenberg single-pass convection tray dryer operating at 40° C. for about 16 hours.

The spray-dried solid amorphous dispersion was evaluated in an in vitro dissolution test using a microcentrifuge method. In this test, 4.5 mg of the spray-dried solid amorphous dispersion was placed into a microcentrifuge tube. The tube was placed in a 37° C. sonicating bath, and 1.8 mL phosphate buffered saline (PBS) at ph 6.5 and 290 mOsm/kg was added, resulting in a torcetrapib concentration of 1000 μg/mL if all of the drug dissolved. The sample was quickly mixed using a vortex mixer for about 60 seconds. The sample was centrifuged at 13,000 G at 37° C. for 1 minute. The resiliting superatant solution was then sampled and diluted 1:6 (by volume) with methanol and then analyzed by high-performance liquid chromatography (HPLC). The contents of the tube was mixed on the vortex mixer and allowed to stand undisturbed at 37° C. until the next sample was taken. Samples were collected at 4, 10, 20, 40, 90, and 1200 minutes. The concentrations of drug obtained in these samples are shown in Table 9, which represent the average of duplicate tests. The results using crystalline drug are included in Table 9 for

TABLE 9

| Sample | Time (min) | Torcetrapib Concentration ($\mu$g/mL) | AUC (min-$\mu$g/mL) |
|---|---|---|---|
| Solid Amorphous Dispersion | 0 | 0 | 0 |
|  | 4 | 79 | 200 |
|  | 10 | 22 | 500 |
|  | 20 | 18 | 700 |
|  | 40 | 17 | 1,000 |
|  | 90 | 18 | 1,900 |
|  | 1200 | 210 | 129,000 |
| Crystalline Drug | 0 | 0 | 0 |
|  | 4 | <1 | <2 |
|  | 10 | <1 | <8 |
|  | 20 | <1 | <18 |
|  | 40 | <1 | <38 |
|  | 90 | <1 | <88 |
|  | 1200 | <1 | <1,200 |

The results of these dissolution tests are summarized in Table 10, which shows the maximum concentration of torcetrapib in solution during the first 90 minutes of the test ($MDC_{90}$), the area under the aqueous concentration versus time curve after 90 minutes ($AUC_{90}$), and the concentration at 1200 minutes ($Cl_{200}$).

TABLE 10

| Sample | Aqueous-Soluble Polymer | Torcetrapib Conc. in the Dispersion (wt %) | Receptor Solution | $MDC_{90}$ ($\mu$g/mL) | $AUC_{90}$ (min-$\mu$g/mL) | $C_{1200}$ ($\mu$g/mL) |
|---|---|---|---|---|---|---|
| Solid Amorphous Dispersion | HPMCAS-HG | 40 | PBS | 79 | 1,900 | 210 |
| Crystalline Drug | None | NA | PBS | <1 | <88 | <1 |

The results summarized in Table 10 show that the solid amorphous dispersion provided concentration enhancement relative to crystalline drug. The solid amorphous dispersion provided a $C_{max,90}$ value that was greater than 79-fold that of the crystalline drug, and an $AUC_{90}$ value that was greater than 21-fold that of the crystalline drug.

To form Example 12, 78 wt % of the CETP inhibitor solid amorphous dispersion and 22 wt % of the HMG-CoA reductase inhibitor composition of Example 1 were mixed together in a twin-shell blender, screened, mixed again, and then compressed into slugs. The acidic concentration-enhancing polymer HPMCAS-HG comprised 47 wt % of Example 12, and atorvastatin calcium comprised 0.93 wt % of Example 12 for an HPMCAS-HG/atorvastatin ratio of 15 (w/w).

Example 12 was stored at 40° C. and 75% relative humidity for 6 weeks to increase the rate of chemical and physical changes occurring in the materials in order to simulate a longer storage interval in a typical storage environment. Following storage, the sample was analyzed for atorvastatin purity using HPLC as described in Example 1. The results are summarized in Table 11 and show that the sample had a degree of degradation of 0.16 wt %, demonstrating that blending an HMG-CoA reductase inhibitor granulation with a solid amorphous dispersion results in acceptably low degrees of degradation of the HMG-CoA reductase inhibitor.

TABLE 11

| | Degradant Concentration (wt %) | | |
|---|---|---|---|
| Example | Before Storage | After Storage 6 weeks at 40° C./75% RH | Degree of Degradation (wt %) |
| Example 12 | 0.05 | 0.21 | 0.16 |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A unitary dosage form comprising:
   (a) a cholesteryl ester transfer protein inhibitor composition comprising a solid amorphous dispersion of a cholesteryl ester transfer protein inhibitor and an acidic concentration-enhancing polymer selected from the group consisting of hydroxypropyl methyl cellulose acetate succinate, hydroxypropyl methyl cellulose phthalate, cellulose acetate phthalate, cellulose acetate trimellitate and carboxymethyl ethyl cellulose; and
   (b) an HMG-CoA reductase inhibitor composition comprising an HMG-CoA reductase inhibitor;
   wherein said solid amorphous dispersion and said HMG-CoA reductase inhibitor are substantially separate from one another in said dosage form.

2. The unitary dosage form of claim 1 wherein said dosage form comprises a plurality of granules of said cholesteryl ester transfer protein inhibitor composition and a plurality of granules of said HMG-CoA reductase inhibitor composition.

3. The unitary dosage form of claim 1 wherein said dosage form comprises at least two layers, at least one of said layers comprising said cholesteryl ester transfer protein inhibitor composition and another of said layers comprising said HMG-CoA reductase inhibitor composition.

4. The unitary dosage form of claim 1 wherein at least one of said cholesteryl ester transfer protein inhibitor composition and said HMG-CoA reductase inhibitor composition has a non-acidic coating.

5. The unitary dosage form of claim 1 wherein said dosage form is selected from the group consisting of a tablet, caplet, pill, capsule, powder, and a kit comprising one or more tablets, caplets, pills, capsules, sachets, powders, or solutions to be taken together.

6. The unitary dosage form of claim 1 wherein said dosage form provides at least one of:
   (a) an improvement in the maximum concentration of said cholesteryl ester transfer protein inhibitor in a use environment of at least 1.25-fold relative to a control composition consisting essentially of said cholesteryl ester transfer protein inhibitor alone;
   (b) an area under the concentration of said cholesteryl ester transfer protein inhibitor versus time curve in the use environment for any period of at least 90 minutes between the time of introduction into the use environment and about 270 minutes following introduction to the use environment that is at least 2-fold that of said control composition consisting essentially of said cholesteryl ester transfer protein inhibitor alone;
   (c) a maximum concentration of said cholesteryl ester transfer protein inhibitor in the blood of at least 1.25-fold relative to a control composition consisting essentially of said cholesteryl ester transfer protein inhibitor alone; and
   (d) an improvement in the relative bioavailability of said cholesteryl ester transfer protein inhibitor in the use environment of at least 1.25-fold relative to said control composition consisting essentially of said cholesteryl ester transfer protein inhibitor alone.

7. The unitary dosage form of claim 1 wherein said composition provides an improvement in chemical stability of said HMG-CoA reductase inhibitor relative to a control composition consisting essentially of a blended mixture of the individual components of said cholesteryl ester transfer protein inhibitor composition and the individual components of said HMG-CoA reductase inhibitor composition.

8. The unitary dosage form of claim 1 wherein said HMG-CoA reductase inhibitor is selected from the group consisting of fluvastatin, lovastatin, pravastatin, atorvastatin, simvastatin, cerivastatin, rivastatin, mevastatin, velostatin, compactin, dalvastatin, fluindostatin, rosuvastatin, pitivastatin, dihydrocompactin, and pharmaceutically acceptable forms thereof.

9. The unitary dosage form of claim 1 wherein at least one of said cholesteryl ester transfer protein inhibitor composition and said HMG-CoA reductase inhibitor composition further comprises a base.

10. The unitary dosage form of any of claims 1-8 wherein said HMG-CoA reductase inhibitor is atorvastatin or pharmaceutically acceptable forms thereof.

11. A method for forming a unitary dosage form comprising:
   (a) forming a solid amorphous dispersion comprising a cholesteryl ester transfer protein inhibitor and a concentration-enhancing polymer selected from the group consisting of hydroxypropyl methyl cellulose acetate succinate, hydroxypropyl methyl cellulose phthalate, cellulose acetate phthalate, cellulose acetate trimellitate and carboxymethyl ethyl cellulose; and
   (b) combining said solid amorphous dispersion with an HMG-CoA reductase inhibitor to form said unitary dosage form;
wherein said solid amorphous dispersion and said HMG-CoA reductase inhibitor are combined so that said solid amorphous dispersion and said HMG-CoA reductase inhibitor are substantially separate from one another in said dosage form.

12. The method of claim 11 wherein said step (b) further comprises the step of forming a plurality of granules comprising said solid amorphous dispersion, and further comprising the step of forming an HMG-CoA reductase inhibitor composition, and then mixing said HMG-CoA reductase inhibitor composition with said plurality of granules.

13. The method of claim 11 wherein said step (b) further comprises forming at least two layers, at least one of said layers comprising said solid amorphous dispersion and another of said layers comprising said HMG-CoA reductase inhibitor.

* * * * *